(12) United States Patent
Jarosch et al.

(10) Patent No.: US 8,101,734 B2
(45) Date of Patent: Jan. 24, 2012

(54) GHRELIN BINDING NUCLEIC ACIDS

(75) Inventors: Florian Jarosch, Berlin (DE); Dirk Eulberg, Berlin (DE); Christian Maasch, Berlin (DE); Steffen Helmling, Boston-Jamaica Plain, MA (US); Sven Klussmann, Berlin (DE)

(73) Assignee: NOXXON Pharma AG, Berlin (DE)

( * ) Notice: Subject to any disclaimer, the term of this patent is extended or adjusted under 35 U.S.C. 154(b) by 348 days.

(21) Appl. No.: 11/400,459

(22) Filed: Apr. 7, 2006

(65) Prior Publication Data

US 2006/0258607 A1  Nov. 16, 2006

(30) Foreign Application Priority Data

Apr. 8, 2005  (EP) .................................. 05007795

(51) Int. Cl.
*C07H 21/04* (2006.01)
(52) U.S. Cl. ..................................................... 536/23.1
(58) Field of Classification Search .................. None
See application file for complete search history.

(56) References Cited

U.S. PATENT DOCUMENTS

| | | | |
|---|---|---|---|
| 5,847,258 A | 12/1998 | Ryals et al. | |
| 6,110,900 A | 8/2000 | Gold et al. | |
| 2003/0211967 A1 | 11/2003 | Bryant et al. | |
| 2006/0257867 A1 | 11/2006 | Helmling et al. | |
| 2006/0258607 A1 | 11/2006 | Jarosch et al. | |
| 2007/0031840 A1 | 2/2007 | Klussmann et al. | |

FOREIGN PATENT DOCUMENTS

| | | |
|---|---|---|
| DE | 19808591 | 9/1999 |
| WO | WO96/34879 | 11/1996 |
| WO | WO01/87335 | 11/2001 |
| WO | WO01/92292 | 12/2001 |
| WO | WO2004-013274 | 2/2004 |
| WO | WO 2004013274 A2 * | 2/2004 |
| WO | WO2005-049828 | 6/2005 |

OTHER PUBLICATIONS

Wood, "DNA-DNA hybridization . . . BIAcore" Microchem J 47:330-337, 1993.
Helmling et al., "Inhibition of . . . Spiegelmer" PNAS 101:13174-13179, 2004.
Raghavan et al., "BlAcore..complexes" Structure 3:331-333, 1995.
Bednarek et al., J Med Chem 43:4370-4376, 2000.
Nolte et al., Nat Biotech 14:1116-1119, 1996.
Klussmann et al., Nat Biotech 14:1112-1115, 1996.
Shuto et al., "Hypothalamic..adiposity" J Clin Inves 109:1429-1435, 2002.
Leva et al., "GnRH . . . antagonism" Chem Biol 9:351-359, 2002.
Eaton et al., Bioorg Med Chem 5:1087-1096, 1997.

* cited by examiner

*Primary Examiner* — Bradley L Sisson
(74) *Attorney, Agent, or Firm* — MDIP LLC

(57) ABSTRACT

The present invention is related to a nucleic acid, preferably binding to ghrelin, whereby the nucleic acid comprises
 a first stretch Box A, and
 a second stretch Box B,
whereby
 the first stretch Box A comprises about 25 consecutive nucleotides,
 the second stretch Box B comprises about six to eight consecutive nucleotides,
whereby
 a 3'-terminal stretch of nucleotides of the first stretch Box A hybridizes with the second stretch Box B, whereby upon hybridization a first double-stranded structure is formed, whereby such first double-stranded structure comprises a bulge.

11 Claims, 29 Drawing Sheets

Sequences of manual selection of truncated P2-RNA-pool

| Name | Sequence | F | C | $K_D$ [nM] | a.c. [%] | $IC_{50}$ [nM] |
|---|---|---|---|---|---|---|
| MS-P2-E3 | GGGUAAGCGUAAGACCGAAAGUAACCAAUCCUACCGUAUAUACGGUGAGGCAGCAC | 1/23 | = | n.t. | n.t | n.t. |
| MS-P2-G2 | GGGUAAGCGUAAGACCGAAAGUAACCAAUCCUACCGUAUCUACAGUGAGGCAGCAC | 1/23 | + | 102 | 61 | 12 |
| MS-P2-D2 | GGGUAAGCGUAAGACCGAAAGGUAACCAAUCCUACCGUAUCUACGGUGAGGCAGCAC | 4/23 | + | 31 | 60 | 4,5 |
| MS-P2-A3 | GGGUAAGCGUAAGACCGAAAGUAACCAAUCCUAUCGUAUCUAUGGUGAGGCAGCAC | 1/23 | = | n.t. | n.t. | n.t. |
| MS-P2-E1 | GGGUAUGCAUAAGACCGAAAGUAACCAAUCCUACCGUAUCUACGGUGAGGCAGCAC | 1/23 | ++ | n.t. | n.t. | n.t. |
| MS-P2-B1 | GGGUAUGCGUAAGACCGAAAGUAACCAAUCCUACCGUAUCUACGGUGAGGCAGCAC | 4/23 | ++ | 34 | 66 | 4,0 |
| MS-P2-F1 | GGGUGAGCGUAAGACCGAAGGUAACCAAUCCUACCGUAUCUACGGUGAGGCAGCAC | 2/23 | ++ | n.t. | n.t. | n.t. |
| MS-P2-C3 | GGGUAUGUGUAAGACCGAAAGUAACCAAUCCUACCAUAUCUACGGUGAGGCAGCAC | 1/23 | ++ | n.t. | n.t. | n.t. |
| MS-P2-C2 | GGGUGUGCGUAAGACCGAAAGUAACCAAUCCUACCAUAUCUACGGUGAGGCAGCAC | 1/23 | ++ | 26 | 58 | 4,5 |
| MS-P2-H2 | GGGUGUGCGUAAGACCGAAAGUAACCAAUCCUACCAUAUCUAUGGUGAGGCAGCAC | 1/23 | = | n.t. | n.t. | n.t. |
| MS-P2-A4 | GGGUGUGCGUAAGACCGAAAGUAACCAAUCCUACCUACUAACUGGUGAGGCAGCAC | 1/23 | ++ | 26 | 58 | 8,0 |
| MS-P2-B2 | GGGUGUGA-CGUAAGACCGAAAGUAACCAAUCCUACCUUUCCUGAGGUGAGGCAGCAC | 1/23 | ++ | 22 | 58 | 6,5 |
| MS-P2-A2 | GGGUGCUCAAAAAAGUAAGUCCGAAGGUAACCAAUCCUACAGCAC | 1/23 | + | 45 | 60 | 7,5 |
| MS-P2-H3 | GGGUGCUCAAUGC-GUAAGUCCGAAGGUAACCAAUCCUGAGCAC | 1/23 | + | 67 | 52 | 35 |
| MS-P2-D1 | GGGUGUUGUGAGGCAAUAA-GUAAGUCCGAAGGUAACCAAUCCUGCAGCAC | 2/23 | n.t. | n.t. | n.t. | n.t. |

F = Frequency; C. = competition experiments; a.c. = active conformation; n.t. = not tested;

Box A    Box B    Box C1 and C2    Box D    Box E

++ : much better than SOT-C;    + : better than SOT-C    = : equivalent to SOT-C

FIG. 1

ALIGNMENT OF IN VITRO SELECTED SPIEGELMERS FROM CONVENTIONAL LIBRARIES

```
SOT-C (B11trc)    CGUGU    GAGGCAAU                              AAAACUUAAGUCCGAAGGUAACCAAUCCUAC    ACG     47 nt
SOT-D-000 (#)     CGUGCGGUGAGGCAG                         ACGUAAGACCGAAGGUAACCAUUCCUACCCACG           48 nt
SOT-D (C12)       CGUGCGGUGAGGCA                          AAAACGUAAGACCGAAGGUAACCAUUCCUACCCACG        50 nt
F12               CGUGU    GAGGUAGUAAAAAAAAAAAACGUAAAAUCCGAAGGUAACCAAUCCUAC    ACG     56 nt
                  *****    ***  *++++++++++++++++++ ***  ***************  ******   ***
```

\*, identical positions in all sequences; underlined bases, probably involved in helix formation; +++, highly variable region \# = SOT-R04-DR14-F7 trc

FIG. 3

TRUNCATION AND FURTHER RATIONAL DESIGN OF SPIEGELMERS FROM CONVENTIONAL LIBRARIES

| Molecule | Sequence | Length | Activity |
|---|---|---|---|
| SOT-D-000 | CGUGCGGUGAGGCAGACGUAAGACCGAAGGUAACCAUUCCUACCCACG | 48 nt | ++ |
| SOT-D-100 | CGGUGAGGCAGACGUAAGACCGAAGGUAACCAUUCCUACCG | 41 nt | ++ |
| SOT-D-101 | CGGUGAGGCAGA   UAAGACCGAAGGUAACCAUUCCUACCG | 39 nt | ++ |
| SOT-D-102 | CGGUGAGGCA A   UAAGACCGAAGGUAACCAUUCCUACCG | 38 nt | − |
| SOT-D-104 | GGUGAGGCAGACGUAAGACCGAAGGUAACCAUUCCUACC | 39 nt | + |
| SOT-D-106 | GGU AGGCAGACGUAAGACCGAAGGUAACCAUUCCUACC | 38 nt | − |
| SOT-D-108 | CCGGUGAGGCAGACGUAAGACCGAAGGUAACCAUUCCUACCGG | 43 nt | ++ |
| SOT-D-109 | CCGGUGAGGCA---GUAAGACCGAAGGUAACCAUUCCUACCGG | 40 nt | ++ |
| SOT-D-110 | CCGGUGAGGCAG---UAAGACCGAAGGUAACCAUUCCUACCGG | 40 nt | ++ |
| SOT-D-111 | CCGGUGAGGC----CGUAAGACCGAAGGUAACCAUUCCUACCGG | 40 nt | − |

UNDERLINED BASES, PROBABLY INVOLVED IN HELIX FORMATION: ___, PEG SPACER. ACTIVITY SCORES: ++, GOOD; +, FAIR; −, WEAK;

FIG. 8

Variants of Spiegelmer SOT-E: Binding analysis

5': Truncation at the 5'-end; 3': Truncation at the 3'-end; Loop: Truncation at the „Loop" and the helix; nt: nucloetides
S: Hexaethyleneglycol-Spacer; i.c.: in comparison

| Variant | 5' [nt] | 3' [nt] | Loop [nt] | S | Remark | IC$_{50}$ [nM] | Increase of binding i.c. to NOX-B11 | Decrease of binding i.c. to SOT-E |
|---|---|---|---|---|---|---|---|---|
| SOT-C | | | | | | 20 | 1 | 5,0-5,7 |
| SOT-E | | | | | | 3,5-4,0 | 6,6-8,0 | 1 |
| SOT-E-14 | 6 | | | | | SOT-E | 5,0-5,7 | 1 |
| SOT-E-09 | 7 | | | | | 8,5 | 2,3 | 2,1-2,4 |
| SOT-E-12 | | 2 | | | | 4,5 | 4,4 | 1,1-1,3 |
| SOT-E-11 | | | 6 | 1 | | SOT-E | 5,0-5,7 | 1 |
| SOT-E-02 | | | 8 | 1 | | 4,5 | 4,4 | 1,1-1,3 |
| SOT-E-19 | 6 | | 6 | 1 | | SOT-E | 5,0-5,7 | 1 |
| SOT-E-21 | 6 | | 6 | 1 | The orignal 5'- and 3'-end are linked together. The loop is displaced by the new 5'- and 3'-end. | SOT-E | 5,0-5,7 | |
| SOT-E-33 | 6 | 2 | 6 | 1 | | 4,5 | 4,7 | 1,1-1,3 |
| SOT-E-25 | 6 | 2 | 6 | 1 | The orignal 5'- and 3'-end are linked together. The loop is displaced by the new 5'- and 3'-end. | 4,5 | 4,7 | 1,1-1,3 |

FIG. 13

SOT-E-25

```
5' CCG[GUGAGG]CA----S----[GUAAGACCGAAGGUAACCAUUCCUAC]CGG  SOT-D-109

5' GGGUGAGCG[UAAGACCGAAGGUAACCAUUCCUAC]CG[GUAUCUACG][GUGAGG]CAGCAC  SOT-E
5' ------GCG[UAAGACCGAAGGUAACCAUUCCUAC]CG---S---CG[GUGAGG]CAGCAC  SOT-E -19
5' ---S---GCG[UAAGACCGAAGGUAACCAUUCCUAC]CG  5' CG[GUGAGG]CAGCAC  SOT-E -21
5' ---S---GCG[UAAGACCGAAGGUAACCAUUCCUAC]CG  5' CG[GUGAGG]CAGC  SOT-E -33
5' ---S---GCG[UAAGACCGAAGGUAACCAUUCCUAC]CG     CG[GUGAGG]CAGC--  SOT-E -25
```

Box A    Box B    Box C1 and C2    Box D    Box E

S = Spacer

FIG. 21

| Sequence | Name | nt | IC$_{50}$ [nM] |
|---|---|---|---|
| GGGUGAGCGUAAGACCGAAGGUAACCAAUCCUACCGGUAUCUACGGUGAGGCAGCAC | SOT-E | 56 | 4-5 |
| ------GCGUAAGACCGAAGGUAACCAAUCCUACCG----L---CGGUGAGGCAGCAC | SOT-E-19 | 44 | 4-5 |
| ------GCGUAAGACCGAAGGUAACCAAUCCUACCGGUAUCUACGGUGAGGCAGCAC | SOT-E-19-L | 50 | 4-5 |
| ------GCGUAAGACCGAAGGUAACCAAUCCUACCG-AAA--CGGUGAGGCAGCAC | SOT-E-19-L1 | 47 | IC$_{50}$ > 5 |
| ------GCGUAAGACCGAAGGUAACCAAUCCUACCG-AUA--CGGUGAGGCAGCAC | SOT-E-19-L2 | 47 | IC$_{50}$ > 5 |
| ------GCGUAAGACCGAAGGUAACCAAUCCUACCG-ACA--CGGUGAGGCAGCAC | SOT-E-19-L3 | 47 | IC$_{50}$ < 5 |
| ------GCGUAAGACCGAAGGUAACCAAUCCUACCG-CAA--CGGUGAGGCAGCAC | SOT-E-19-L4 | 47 | IC$_{50}$ < 5 |
| ------GCGUAAGACCGAAGGUAACCAAUCCUACCG-AUCU-CGGUGAGGCAGCAC | SOT-E-19-L5 | 48 | IC$_{50}$ > 5 |
| ------GCGUAAGACCGAAGGUAACCAAUCCUACCG-UUU--CGGUGAGGCAGCAC | SOT-E-19-L6 | 47 | IC$_{50}$ > 5 |
| ------GCGUAAGACCGAAGGUAACCAAUCCUACCG-UAU--CGGUGAGGCAGCAC | SOT-E-19-L7 | 47 | IC$_{50}$ > 5 | nt:= nucleotides

FIG. 23

PLATE--- STREPTAVIDIN + BIOTIN-NOX-B11

PLATE--- STREPTAVIDIN---BIOTIN-NOX-B11

PLATE--- STREPTAVIDIN---BIOTIN-NOX-B11 + GHRELIN

PLATE--- STREPTAVIDIN---BIOTIN-NOX-B11---GHRELIN

PLATE--- STREPTAVIDIN---BIOTIN-NOX-B11---GHRELIN + 1° ab

PLATE--- STREPTAVIDIN---BIOTIN-NOX-B11---GHRELIN---1° ab

PLATE--- STREPTAVIDIN---BIOTIN-NOX-B11---GHRELIN---1° ab- + 2° ab-HRP

PLATE--- STREPTAVIDIN---BIOTIN-NOX-B11---GHRELIN---1° ab----2° ab-HRP

GHRELIN BINDING NUCLEIC ACIDS

FIELD OF THE INVENTION

The present invention is related to nucleic acids binding to ghrelin, and their use in the manufacture of a medicament, and their use in the manufacture of a diagnostic agent.

BACKGROUND OF THE INVENTION

Ghrelin was identified as the natural ligand of the growth hormone secretagogue receptor 1a (GHSR1a). The receptor is most abundant in the pituitary gland and in hypothalamic parts of the brain, but can also be detected in other tissues at low concentrations. Since the late 70ies synthetic peptides and other compounds, named secretagogues had been shown to stimulate the release of growth hormone. However, the natural ligand responsible for the release of growth hormone remained unknown until the discovery of ghrelin in 1999. Ghrelin is a highly basic 28 amino acid peptide hormone with an octanoyl acid side chain at the third amino acid of its N-terminus (serine 3). This unusual modification is required for the interaction at the GHS-receptor and its activity. However, in biological samples a mixture of both the octanoyl ghrelin which is a form of a bioactive ghrelin, and the unmodified or des-octanoyl ghrelin is present. The amino-acid sequence of the purified rat ghrelin was determined to be GSSFLSPEHQKAQQRKESKKPPAKLQPR (SEQ. ID. No. 2); the corresponding human sequence deviates in two positions only, carrying the same n-octanoyl-side chain at the amino acid position serine 3 and was determined to be GSSFLSPEHQRVQQRKESKKPPAKLQPR (SEQ. ID. No. 1).

Beside the naturally occurring n-octanoyl residue, unsaturated or branched octanoyl groups, and longer aliphatic chains introduced at position 3 of ghrelin mediate receptor recognition as well. The receptor interaction domain is located at the very N-terminus of ghrelin; deletion studies indicate, that the minimal motif of amino acids 1-5 (ghrelin (1-5) [GSSFL]) (SEQ ID NO: 1, amino acids 1-5) is sufficient for stimulation of GHSR1a, but a strong requirement for peptide modification with the n-octanoyl residue is observed.

Ghrelin has been shown to mediate physiological functions pertinent to an anabolic state. It directly stimulates the release of growth hormone (GH) from the pituitary gland, and may therefore be a suitable target in the treatment of acromegaly. Experiments in rodents also showed ghrelin to induce feeding in a GH-independent fashion by acting upon hypothalamic neurons. Interestingly, the primary site of ghrelin production is in oxyntic glands in the stomach, suggesting that it serves as a hormonal link between stomach, pituitary gland and hypothalamus. The observation that ghrelin administration in rats resulted in weight gain as a consequence of changes in energy intake and/or fuel utilization is in support of such a role. Moreover, systemic ghrelin administration in humans cause sensations of hunger in the test subjects and induce overeating. Based on these findings ghrelin is thought to have a crucial role in the regulation of appetite and body weight, serving as an acute as well as a chronic signal of an underfed state. Additional support for this hypothesis comes from observations that ghrelin levels as well as appetite are reduced in individuals following gastric bypass, contributing at least in part to the efficiency of the procedure in effecting weight loss. Clinical data from patients with Prader-Willi syndrome also suggest that the hyperphagia and obesity associated with the disease are a consequence of tremendous hyperghrelinemia. Moreover, ghrelin was found to induce hyperglycemia and inhibition of insulin release, indicating an involvement in glucose metabolism. Beside these functions in energy metabolism, ghrelin has also been implicated in a number of other processes in the field of gastrointestinal diseases, such as gastric emptying and regualtion of bowel movements. Moreover, ghrelin was also found to be expressed in a number of neuroendocrine tumors and to stimulate, besides GH release from the pituitary, the release of ACTH, PRL, and cortisol. Single injections of ghrelin into healthy individuals were found to increase cardiac output and decrease blood pressure. Thus, ghrelin action appears to be involved in a variety of different tasks. Additional background information related thereto can be found in M. Kojima, H. Hosoda, Y. Date, M. Nakazato, H. Matsu, K. Kangawa, "Ghrelin is a growth-hormone-releasing acylated peptide from stomach", Nature 402:656-60, 1999; M. Tschöp, D. L. Smiley, M. L. Heiman, "Ghrelin induces adiposity in rodents", Nature 407: 908-13, 2000; A. M. Wren et al., "Ghrelin enhances appetite and increases food intake in humans", Journal of Clinical Endocrinology Metabolism 86:5992-6, 2001; M. Nakazato et al., "A role for ghrelin in the central regulation of feeding", Nature 409: 194-8, 2001; N. Nagaya, et al., Am J Physiol Regul Integr Comp Physiol. May 2001; 280(5):R1483-7; Hemodynamic and hormonal effects of human ghrelin in healthy volunteers; Volante M, et al., J Clin Endocrinol Metab. March 2002; 87(3):1300-8. Expression of ghrelin and of the GH secretagogue receptor by pancreatic islet cells and related endocrine tumors; Jeffery P L, et al., J Endocrinol. March 2002; 172(3):R7-11 Expression and action of the growth hormone releasing peptide ghrelin and its receptor in prostate cancer cell lines; Egido E M, et al., Eur J Endocrinol. February 2002; 146(2):241-4 Inhibitory effect of ghrelin on insulin and pancreatic somatostatin secretion; Broglio F, et al., J Clin Endocrinol Metab. October 2001; 86(10):5083-6, Ghrelin, a natural GH secretagogue produced by the stomach, induces hyperglycemia and reduces insulin secretion in humans; Bednarek M A, et al., J Med Chem. October 2000; 43:4370-6 Structure-function studies on the new growth hormone-releasing peptide, ghrelin: minimal sequence of ghrelin necessary for activation of growth hormone secretagogue receptor 1a.

The problem underlying the present invention is to provide a specific antagonist to ghrelin. A further aspect of the problem underlying the present invention is to provide a specific antagonist to the growth hormone secretagogue receptor 1 a (GHSR 1a). Another aspect of the problem underlying the present invention is to provide a compound for the treatment of diseases and disorders involving ghrelin and the GHSR 1a receptor, respectively.

A further problem underlying the present invention is to provide means for the binding of bioactive ghrelin and more particularly to provide a method for the treatment of diseases and disorders mediated by bioactive ghrelin as well as methods for the specific detection of bioactive ghrelin.

SUMMARY OF THE INVENTION

The problem underlying the present invention is solved in a first aspect by a nucleic acid, preferably binding to ghrelin, whereby the nucleic acid comprises
   a first stretch Box A, and
   a second stretch Box B,
whereby
   the first stretch Box A comprises about 25 consecutive nucleotides,
   the second stretch Box B comprises about six to eight consecutive nucleotides, whereby
a 3'-terminal stretch of nucleotides of the first stretch Box A hybridises with the second stretch Box B, whereby upon hybridisation a first double-stranded structure is formed, whereby such first double-stranded structure comprises a bulge.

In an embodiment of each and any aspect of the present invention the ghrelin is a bioactive ghrelin, and more preferably octanoyl ghrlein and most preferably n-octanoyl ghrlein.

In an embodiment the double-stranded structure is formed by the five 3'-terminal consecutive nucleotides of the first stretch Box A and part or all of the nucleotides of the second stretch Box B, preferably the six to eight consecutive nucleotides of the second stretch Box B.

In an embodiment the bulge is formed by 1 to 3 nucleotides of the second stretch Box B, preferably by 1 nucleotide of the second stretch Box B, not base-pairing with the five 3'-terminal consecutive nucleotides of the first stretch Box A.

In an embodiment the bulge is formed by a non-base pairing purine, whereby the purine is preferably a guanosine.

In a preferred embodiment the non-base pairing purine is provided by the second stretch Box B.

In an embodiment the nucleic acid further comprises a third stretch Box C1 and a fourth stretch Box C2,
whereby the third stretch Box C1 comprises at least one nucleotide and
the fourth stretch Box C2 comprises at least one nucleotide, and
whereby the third stretch Box C1 is attached with its 3'-end to the 5'-end of the second stretch Box B, and the fourth stretch Box C2 is attached with its 5'-end to the 3'-end of the first stretch Box A.

In a preferred embodiment the third stretch Box C1 and the fourth stretch Box C2 are capable of hybridisation, whereby upon hybridisation a second double-stranded structure is formed.

In an embodiment the first double-stranded structure forms a first helical structure.

In a preferred embodiment the second double-stranded structure forms a second helical structure.

In a more preferred embodiment the second helical structure is a helix or a helix-like structure comprising from 1 to 10 base pairs, preferably from 1 to 3 base pairs and more preferably from 2 to 3 base pairs.

In a preferred embodiment the first helical structure is prolonged by the second helical structure.

In a preferred embodiment the third stretch Box C1 comprises from about 1 to 10 consecutive nucleotides, preferably 1 to 3 consecutive nucleotides and more preferably 2 or 3 consecutive nucleotides.

In a preferred embodiment the fourth stretch Box C2 comprises from about 1 to 10 consecutive nucleotides, preferably 1 to 3 consecutive nucleotides and more preferably 2 or 3 consecutive nucleotides.

In a preferred embodiment the nucleic acid further comprises a fifth stretch Box D, whereby the fifth stretch Box D comprises at least two consecutive nucleotides.

In a more preferred embodiment the fifth stretch Box D comprises the sequence 5'-CA.

In a more preferred embodiment the fifth stretch Box D comprises any length of consecutive nucleotides, whereby the length is selected from the group consisting of two, three, four, five and six consecutive nucleotides.

In a preferred embodiment the fifth stretch Box D comprises a sequence of

5'CA(X)$_n$3' whereby X is any nucleotide, preferably selected from the group comprising A, G, T, C, U and I and whereby n is any integer selected from the group consisting of 0, 1, 2, 3 and 4.

In a more preferred embodiment the fifth stretch Box D consists of the sequence

5'CA(X)$_n$3' whereby n=4.

In a preferred embodiment the fifth stretch Box D is attached with its 5'-end to the 3'-end of the second stretch Box B.

In a preferred embodiment the nucleic acid further comprises a sixth stretch Box E, whereby the sixth stretch Box E comprises at least one nucleotide.

In a more preferred embodiment the sixth stretch Box E comprises about from 1 to 10 consecutive nucleotides, preferably 1 to 4 consecutive nucleotides and more preferably 3 consecutive nucleotides.

In a further more preferred embodiment at least one of the nucleotides of the sixth stretch Box E is selected from the group consisting of U and G.

In a particularly preferred embodiment the U or G nucleotide is positioned immediately next to the 5' end of the first stretch Box A.

In a preferred embodiment the sixth stretch Box E is attached with its 3'-end to the 5'-end of the first stretch Box A.

In a preferred embodiment the 3'-end of the fifth stretch Box D is attached to the 5'-end of the sixth stretch Box E by a first spacer.

In a preferred embodiment the 3'-end of the fourth stretch Box C2 is attached to the 5'-end of the third stretch Box C1 by a second spacer.

In a preferred embodiment the first and the second spacer are each separately and independently selected from the group comprising hydrophilic spacers.

In a more preferred embodiment the hydrophilic spacer is selected from the group comprising a nucleic acid spacer and a non-nucleic acid spacer.

In a more preferred embodiment the first spacer is a nucleic acid spacer comprising about from 1 to 20 consecutive nucleotides, preferably 1 to 5 consecutive nucleotides and more preferably 2 consecutive nucleotides.

In an alternative more preferred embodiment the second spacer is a nucleic acid spacer comprising about from 3 to 20 consecutive nucleotides, preferably 3 to 5 consecutive nucleotides and more preferably 3 consecutive nucleotides. In an even more preferred embodiment, the second spacer consists of ACA or CAA.

In a further alternative more preferred embodiment the spacer is a non-nucleic acid. In a particularly preferred embodiment thereof the first spacer and/or the second spacer comprises at least one ethylene glycol moiety or a plurality of such ethylene glycol moieties.

In an embodiment the spacer has a molecular weight of about from 172 to 688 Da, preferably 344 Da.

In an embodiment the nucleic acid is a circular nucleic acid.

In an embodiment the nucleic acid has the structure of

5'──── Box C1 ──── Box B ──── Box D ──── Spacer ──── Box E ──── Box A ──── Box C2 or the structure of

5'──── Box E ──── Box A ──── Box C2 ──── Spacer ──── Box C1 ──── Box B ──── Box D In an embodiment the first stretch Box A comprises the sequence of UAAX$_1$X$_2$CCGAAX$_3$GUAX$_4$CCAUUCCUX$_5$C;   (SEQ ID No. 3)

whereby
X$_1$=G or A;
X$_2$=A or U;
X$_3$=G or A;
X$_4$=A or C or U; and
X$_5$=G or A
preferably 5'UAAGACCGAAGGUACCCAAUCCUAC3'.   (SEQ ID No. 4)

In an embodiment the second stretch Box B comprises the sequence of 5'GUGAGG3'.

In an embodiment the sequence of the nucleic acid is selected from the group comprising the sequences according to

| SEQ ID No. | internal reference |
|---|---|
| 5 | MS-P2-E3 |
| 6 | MS-P2-G2 |
| 7 | MS-P2-D2 |
| 8 | MS-P2-A3 |
| 9 | MS-P2-E1 |
| 10 | MS-P2-B1 |
| 11 | MS-P2-F1 |
| 12 | MS-P2-C3 |
| 13 | MS-P2-C2 |
| 14 | MS-P2-H2 |
| 15 | MS-P2-A4 |
| 16 | MS-P2-B2 |
| 17 | MS-P2-A2 |
| 18 | MS-P3-H3 |
| 19 | MS-P2-D1 |
| 20 | SOT-C |
| 21 | F12 |
| 22 | SOT-D (C12) |
| 23 | SOT-D-000 |
| 24 | SOT-D-100 |
| 25 | SOT-D-101 |
| 26 | SOT-D-102 |
| 27 | SOT-D-104 |
| 28 | SOT-D-106 |
| 29 | SOT-D-108 |
| 30 | SOT-D-109 |
| 31 | SOT-D-110 |
| 32 | SOT-D-111 |
| 33 | SOT-E or MS-P2-F1 |
| 73-S-80 | SOT-E-02 |
| 35 | SOT-E-09 |
| 74-S-81 | SOT-E-11 |
| 37 | SOT-E-12 |
| 38 | SOT-E-14 |
| 75-S-82 | SOT-E-19 |
| 76-S-83 | SOT-E-21 |
| 77-S-84 | SOT-E-25 |
| 78-S-85 | SOT-E-33 |
| 43 | SOT-E19-L |
| 44 | SOT-E19-L1 |
| 45 | SOT-E19-L2 |
| 46 | SOT-E19-L3 |
| 47 | SOT-E19-L4 |
| 48 | SOT-E19-L5 |
| 49 | SOT-E19-L6 |
| 50 | SOT-E19-L7 |
| 79-S-86 | SOT-E19-5'-PEG |
| 52 | SOT-D-109 (NOX-B11-2) |
| 72 | biotinylated NOX-B11 |

In the table above, S refers to the spacer.

In a preferred embodiment the sequence of the nucleic acid is selected from the group comprising the sequences according to SEQ ID NO:29; SEQ ID NO:30; SEQ ID NO:33; SEQ ID NO:36; SEQ ID NO:39; SEQ. ID NO:40; SEQ ID NO:41; SEQ ID NO:42; SEQ ID NO:74-S-SEQ ID NO:81; SEQ ID NO:38; SEQ ID NO:75-S-SEQ ID NO:82; SEQ ID NO:76-S-SEQ ID NO:83; SEQ ID NO:77-S-SEQ ID NO:84; SEQ ID NO:78-S-SEQ ID NO:85; SEQ ID NO:46; SEQ ID NO:47; SEQ ID NO:79-S-SEQ ID NO:86; SEQ ID NO:51 and SEQ ID NO:52.

In an embodiment the nucleic acid is capable of binding ghrelin, preferably human ghrelin.

In a preferred embodiment the ghrelin has an amino acid sequence according to SEQ ID No. 1.

In an embodiment the nucleic acid comprises a modification.

In a preferred embodiment the modification is selected from the group comprising a HES moiety and a PEG moiety.

In a more preferred embodiment the modification is a PEG moiety consisting of a straight or branched PEG, whereby the molecular weight of the PEG moiety is preferably from about 20 to 120 kD, more preferably from about 30 to 80 kD and most preferably about 40 kD.

In an alternative more preferred embodiment the modification is a HES moiety, whereby preferably the molecular weight of the HES moiety is from about 10 to 130 kD, more preferably from about 30 to 80 kD and most preferably about 50 kD.

In an embodiment the nucleotides of the nucleic acid are L-nucleotides.

In a further embodiment the nucleic acid consists completely of L-nucleotides.

The problem underlying the present invention is solved in a second aspect by a pharmaceutical composition comprising a nucleic acid according to the first aspect and optionally a further constituent, whereby the further constituent is selected from the group comprising pharmaceutically acceptable excipients and pharmaceutically active agents.

The problem underlying the present invention is solved in a third aspect by the use of a nucleic acid according to the first aspect for the manufacture of a medicament.

The problem underlying the present invention is solved in a fourth aspect by the use of a nucleic acid according to the first aspect for the manufacture of a diagnostic means.

In an embodiment of the third aspect the medicament is for the treatment and/or prevention of a disease or disorder selected from the group comprising obesity, eating disorders, diabetes, glucose metabolism disorders, tumor, blood pressure disorders, cardiovascular diseases, acromegaly and regulation of energy balance, appetite, body weight, and gastrointestinal diseases.

The problem underlying the present invention is solved in a fifth aspect by a complex comprising ghrelin and a nucleic acid according to the first aspect, whereby preferably the complex is a crystalline complex.

The problem underlying the present invention is solved in a sixth aspect by the use of a nucleic acid according to the first aspect for the detection of ghrelin.

The problem underlying the present invention is solved in a seventh aspect by a method for the screening of a ghrelin antagonist or a ghrelin agonist comprising the following steps:
  providing a candidate ghrelin antagonist and/or a candidate ghrelin agonist,
  providing a nucleic acid according to the first aspect,
  providing a test system which provides a signal in the presence of a ghrelin antagonist and/or a ghrelin agonist, and
  determining whether the candidate ghrelin antagonist is a ghrelin antagonist and/or whether the candidate ghrelin agonist is a ghrelin agonist.

The problem underlying the present invention is solved in an eighth aspect by a method for the screening of a ghrelin agonist and/or a ghrelin antagonist comprising the following steps:
  providing ghrelin immobilised to a phase, preferably a solid phase,
  providing a nucleic acid according to the first aspect, preferably a nucleic acid according to the first aspect which is labelled,
  adding a candidate ghrelin agonist and/or a candidate ghrelin antagonist, and
  determining whether the candidate ghrelin agonist is a ghrelin agonist and/or whether the candidate ghrelin antagonist is a ghrelin antagonist.

In an embodiment the determining is carried out such that it is assessed whether the nucleic acid is replaced by the candidate ghrelin agonist or by a candidate ghrelin antagonist.

The problem underlying the present invention is solved in a ninth aspect by a kit for the detection of ghrelin, comprising a nucleic acid according to the first aspect.

The problem underlying the present invention is solved in a tenth aspect by a ghrelin antagonist obtainable by the method according to the eighth aspect.

The problem underlying the present invention is solved in an eleventh aspect by a ghrelin agonist obtainable by the method according to the eighth aspect.

BRIEF DESCRIPTION OF THE DRAWINGS

The present invention is further illustrated by the figures, examples and the sequence listing from which further features, embodiments and advantages may be taken, wherein FIG. 1 shows an alignment of sequences of RNA ligands binding to human ghrelin. In FIG. 1 the sequences are shown in the Sequence Listing with the following sequence identifiers:

| SEQ ID NO. | Sequence |
| --- | --- |
| 5 | MS-P2-E3 |
| 6 | MS-P2-G2 |
| 7 | MS-P2-D2 |
| 8 | MS-P2-A3 |
| 9 | MS-P2-E1 |
| 10 | MS-P2-B1 |
| 11 | MS-P2-F1 |
| 12 | MS-P2-C3 |
| 13 | MS-P2-C2 |
| 14 | MS-P2-H2 |
| 15 | MS-P2-A4 |
| 16 | MS-P2-B2 |
| 17 | MS-P2-A2 |
| 18 | MS-P3-H3 |
| 19 | MS-P2-D1 |

Figure 2:
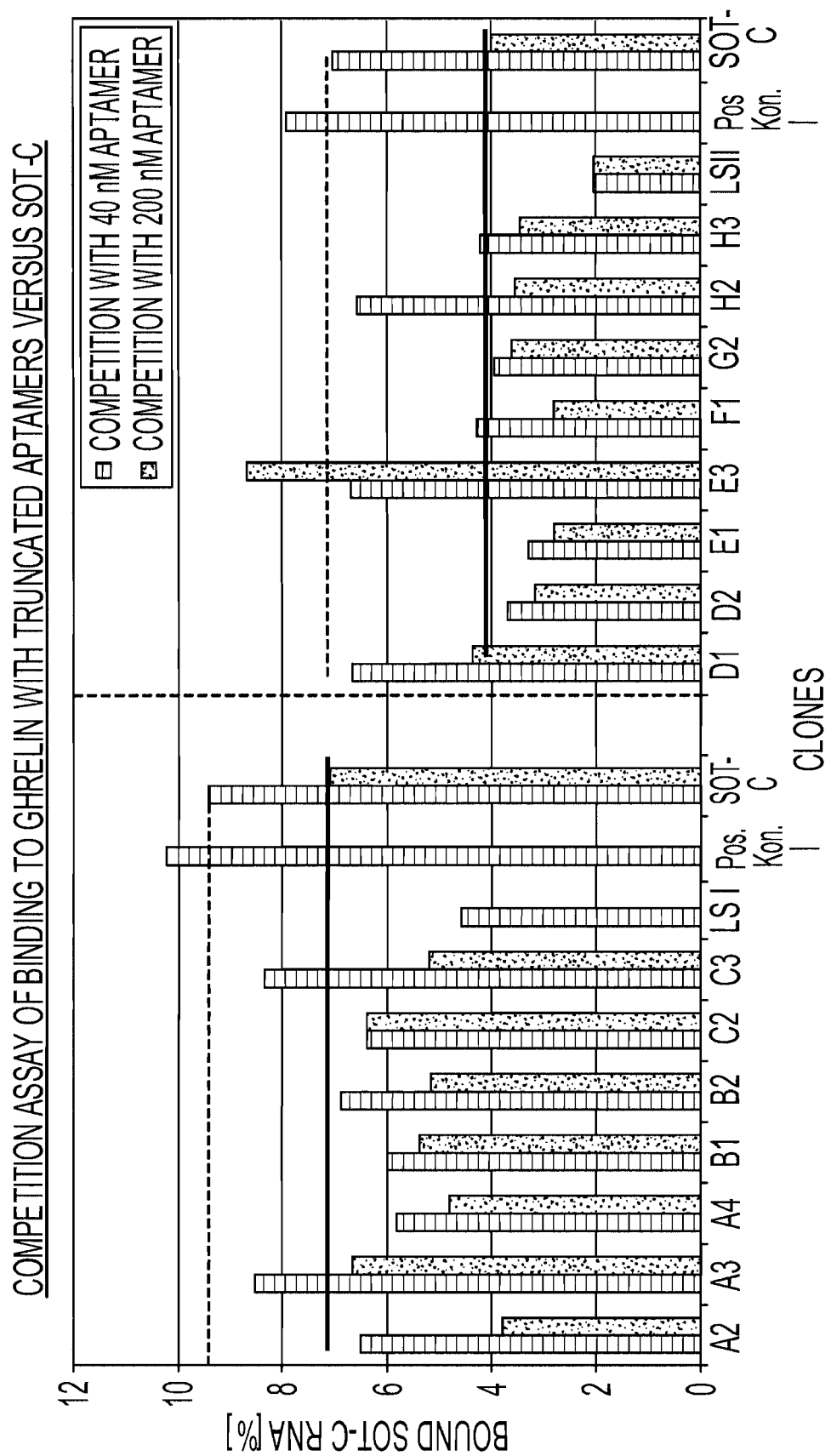

FIG. 2 shows a competition assay of binding to ghrelin with truncated aptamers versus the known sequence SOT-C (B11trc).

FIG. 3 shows an alignment of chosen sequences of RNA ligands, which were published in patent application WO 2004/013274 A2. In FIG. 3 the sequences are shown in the Sequence Listing with the following sequence identifiers:

| SEQ ID NO: | Sequence |
| --- | --- |
| 20 | SOT-C (B11trc) |
| 23 | SOT-D-000 |
| 22 | SOT-D (C12) |
| 21 | F12 |

Figure 4:
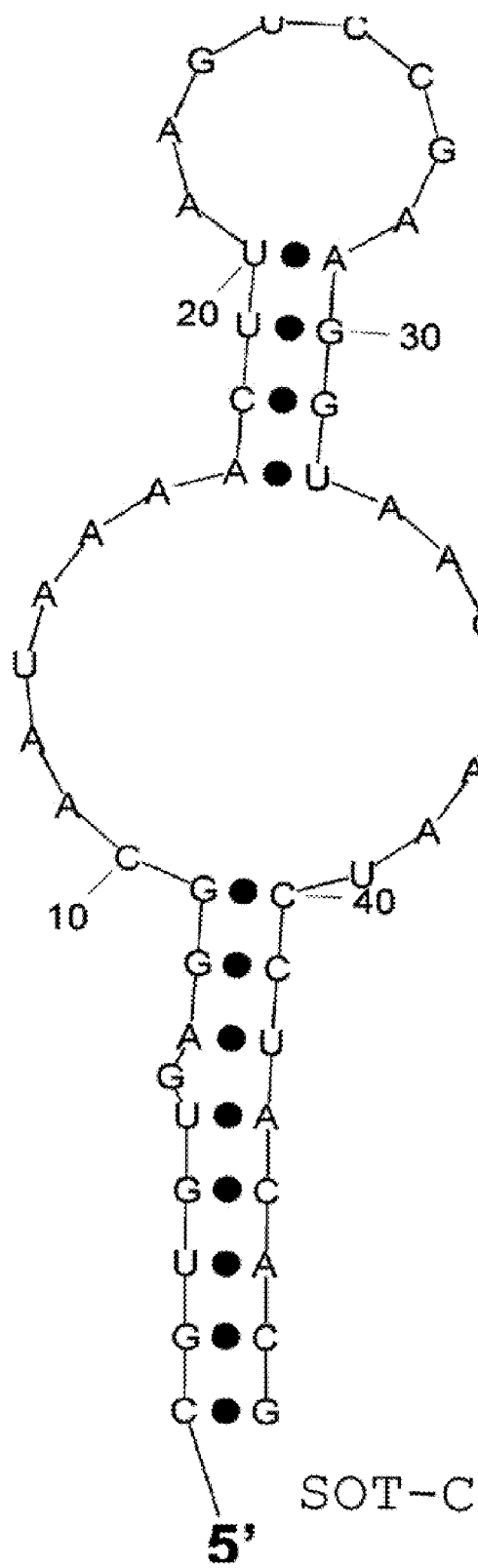

FIG. 4 shows calculated secondary structure of ghrelin binding RNA spiegelmer clone SOT-C, the secondary structure was calculated with the program "RNAfold" (Hofacker et al., 1994, Monatsh. Chem 124:167-188).

Figure 5:
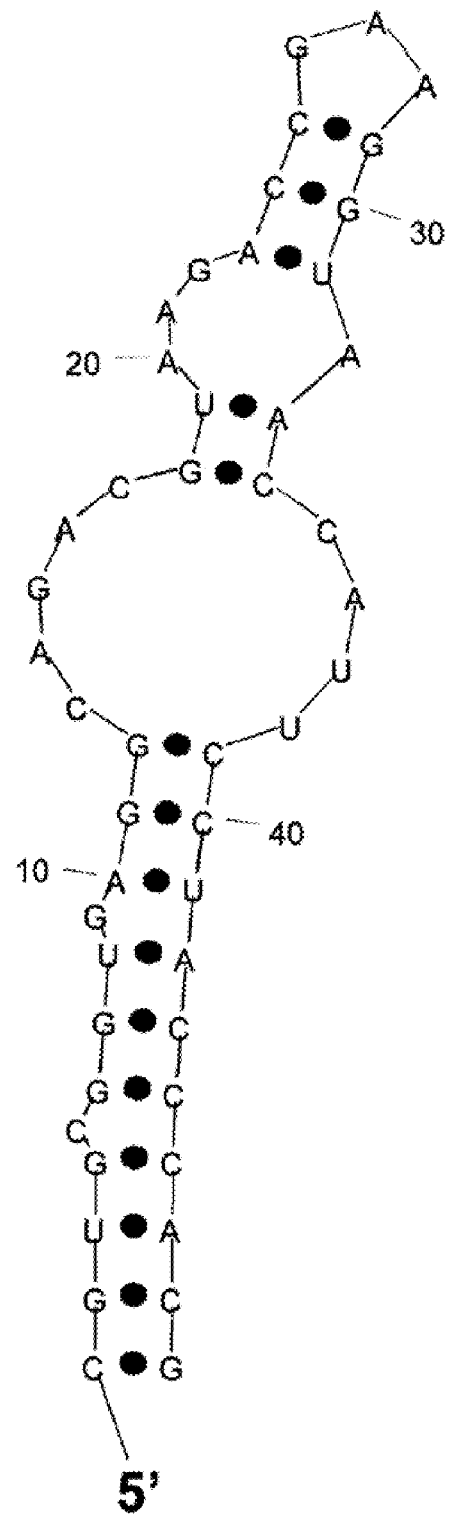

FIG. 5 shows calculated secondary structure of ghrelin binding RNA spiegelmer clone SOT-D-000 (SEQ ID NO: 23), the secondary structure was calculated with the program "RNAfold" (Hofacker et al., 1994, Monatsh. Chem 125:167-188).

Figure 6:
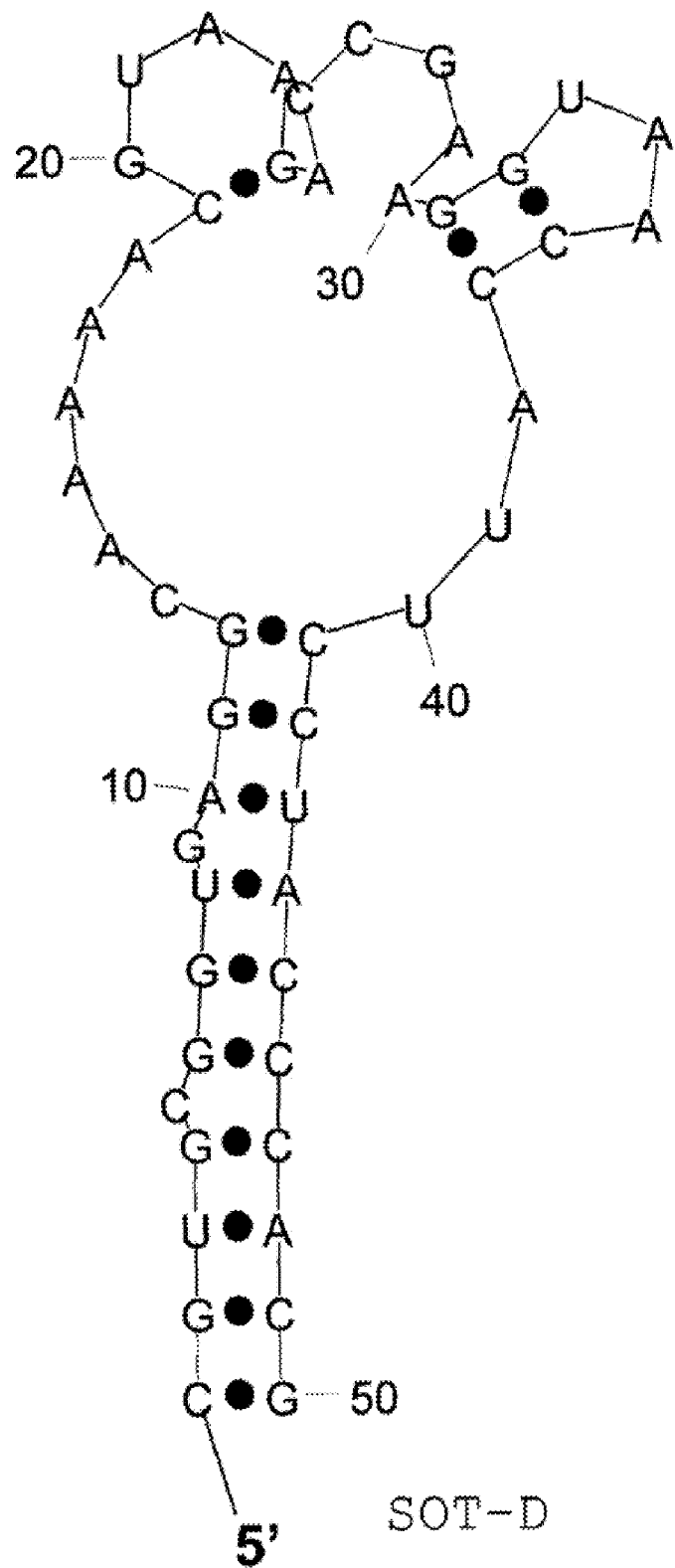

FIG. 6 shows calculated secondary structure of ghrelin binding RNA spiegelmer clone SOT-D (SEQ ID NO: 22), the secondary structure was calculated with the program "RNAfold" (Hofacker et al., 1994, Monatsh. Chem 125:167-188).

Figure 7:
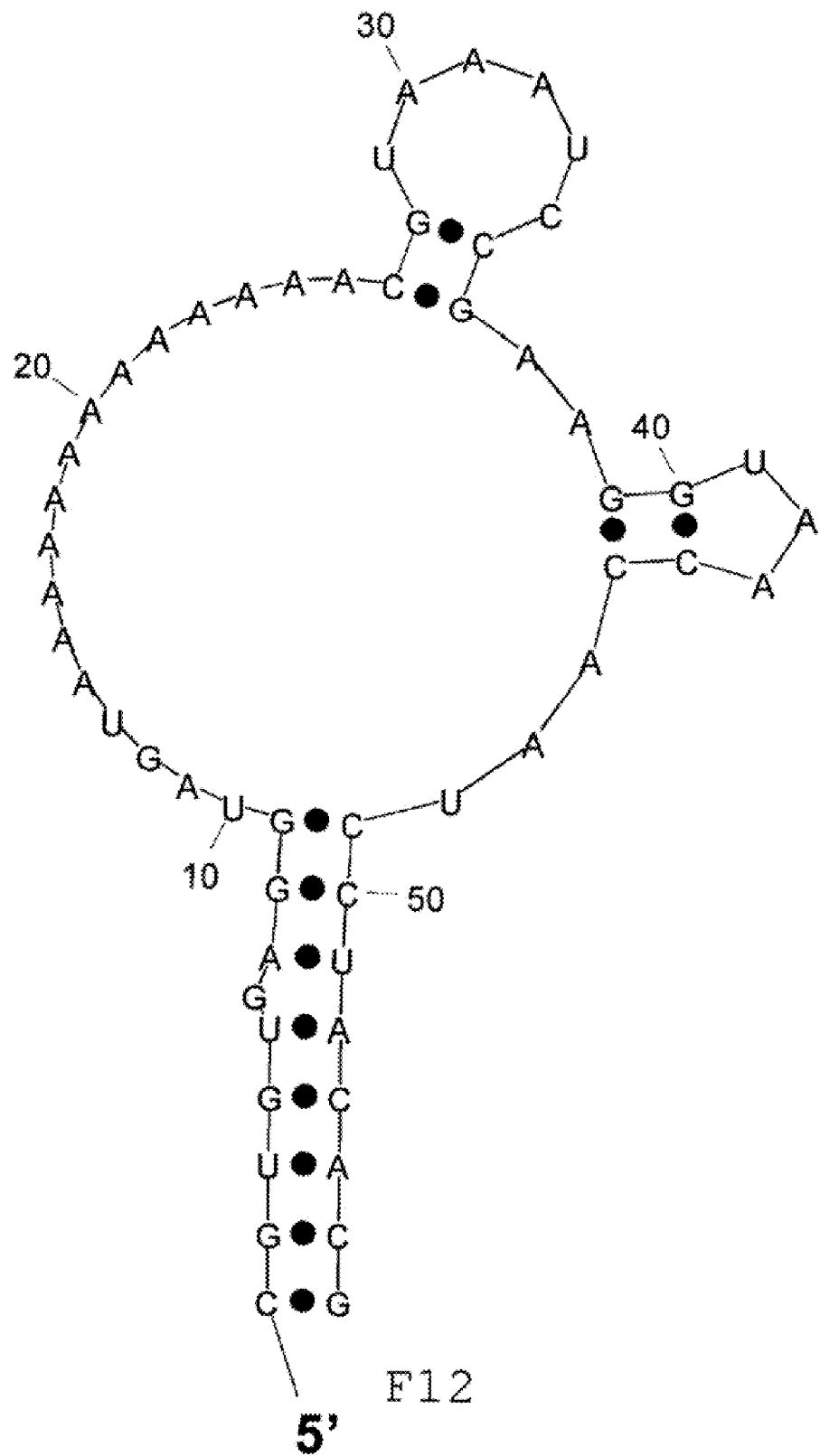

FIG. 7 shows calculated secondary structure of ghrelin binding RNA spiegelmer clone F-12 (SEQ ID NO: 21), the secondary structure was calculated with the program "RNAfold" (Hofacker et al., 1994, Monatsh. Chem 125:167-188).

FIG. 8 shows an alignment of SOT-D-000 derivates which are the result of truncation and relational design experiments. In FIG. 8 the sequences are shown in the Sequence Listing with the following sequence identifiers:

| SEQ ID NO: | Sequence |
| --- | --- |
| 23 | SOT-D-000 |
| 24 | SOT-D-100 |
| 25 | SOT-D-101 |

-continued

| SEQ ID NO: | Sequence |
|---|---|
| 26 | SOT-D-102 |
| 27 | SOT-D-104 |
| 28 | SOT-D-106 |
| 29 | SOT-D-108 |
| 30 | SOT-D-109 |
| 31 | SOT-D-110 |
| 32 | SOT-D-111 |

Figure 9:
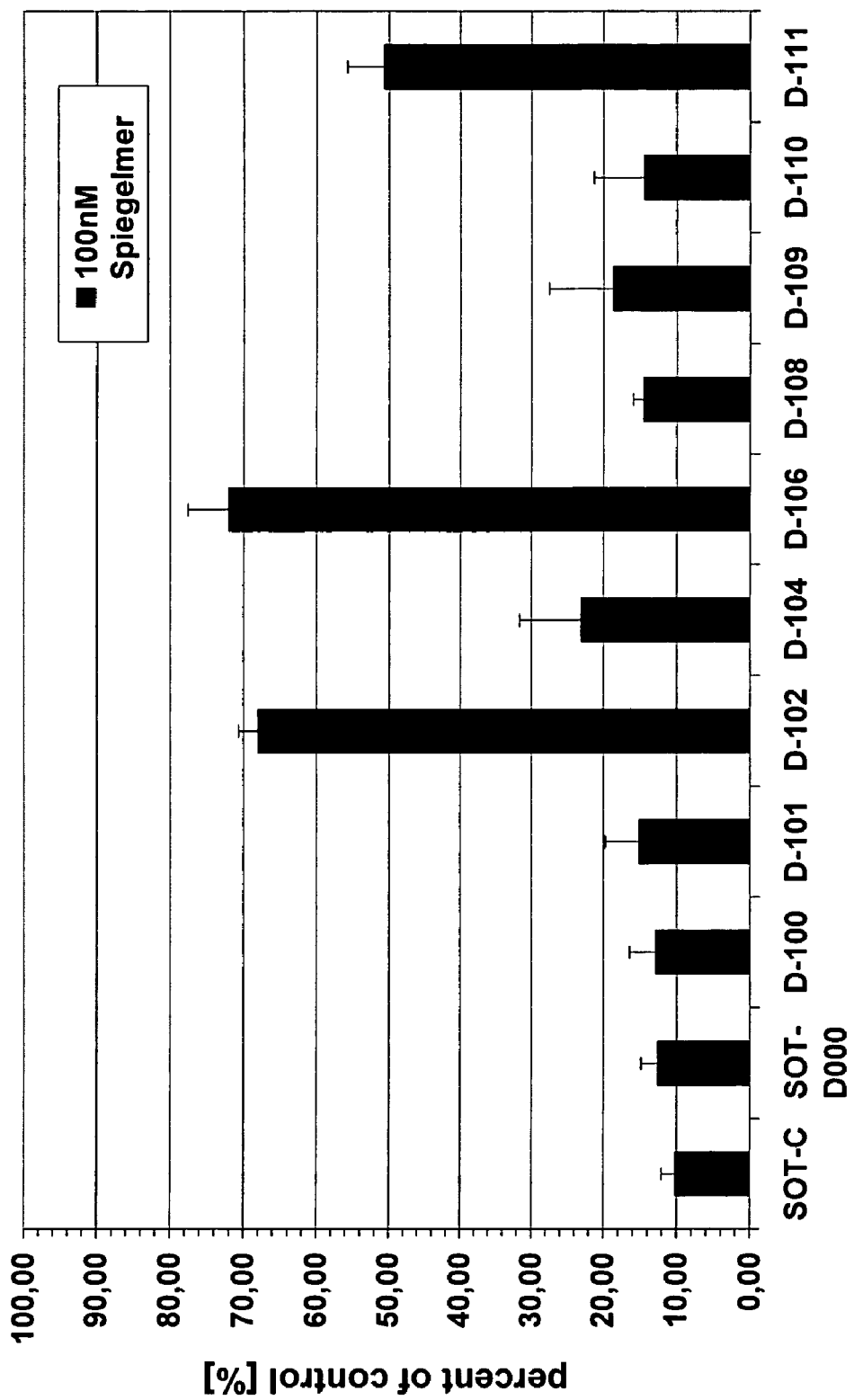

FIG. 9 shows a one-point measurement for the inhibition of ghrelin-induced $Ca^{++}$-release by Spiegelmers SOT-C, SOT-D-000 and variants thereof at room temperature; cells were stimulated with 5 nM ghrelin preincubated at room temperature with various amounts of Spiegelmer SOT-C, SOT-D000 or a variant of D-000 the results show the percentage of fluorescence signal normalized to the signal obtained with no Spiegelmer.

Figure 10:
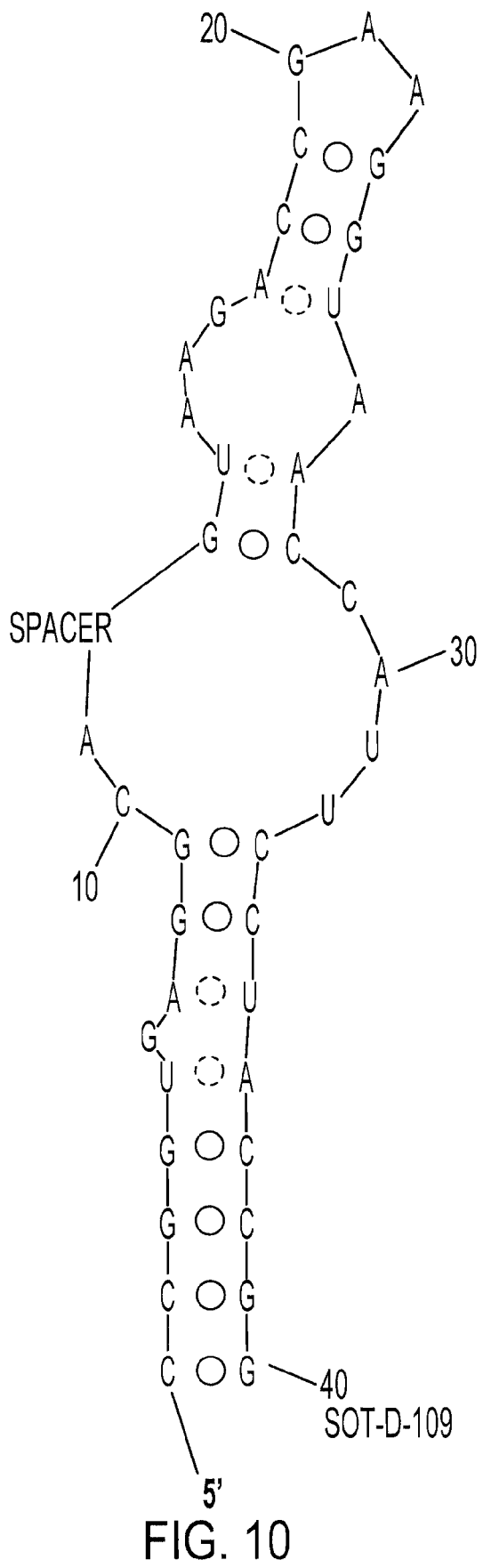

FIG. 10 shows a presumptive secondary structure of ghrelin binding RNA spiegelmer clone SOT-D-109 (SEQ ID NO: 30).

Figure 11:
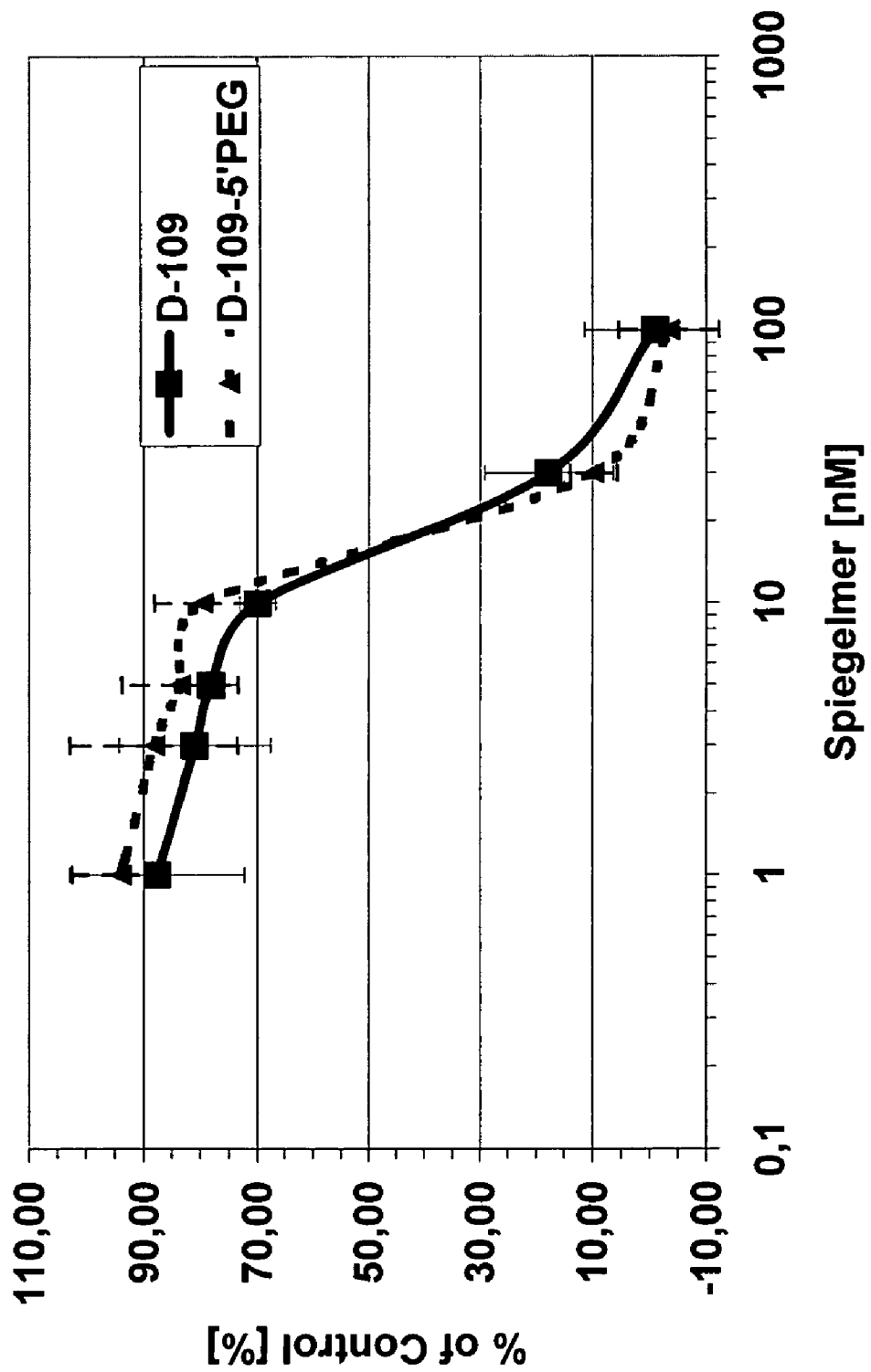

FIG. 11 shows a dose-response curve for the inhibition of ghrelin-induced $Ca^{++}$-release by Spiegelmers D-109 and 5'-PEGylated D-109 at room temperature; cells were stimulated with 5 nM ghrelin preincubated at room temperature with various amounts of Spiegelmer D-109 and 5'-PEGylated D-109; the results show the percentage of fluorescence signal normalized to the signal obtained with no Spiegelmer; Spiegelmer D-109 and its modified versions were found to inhibit ghrelin-induced $Ca^{++}$-release with same $IC_{50}$.

Figure 12:
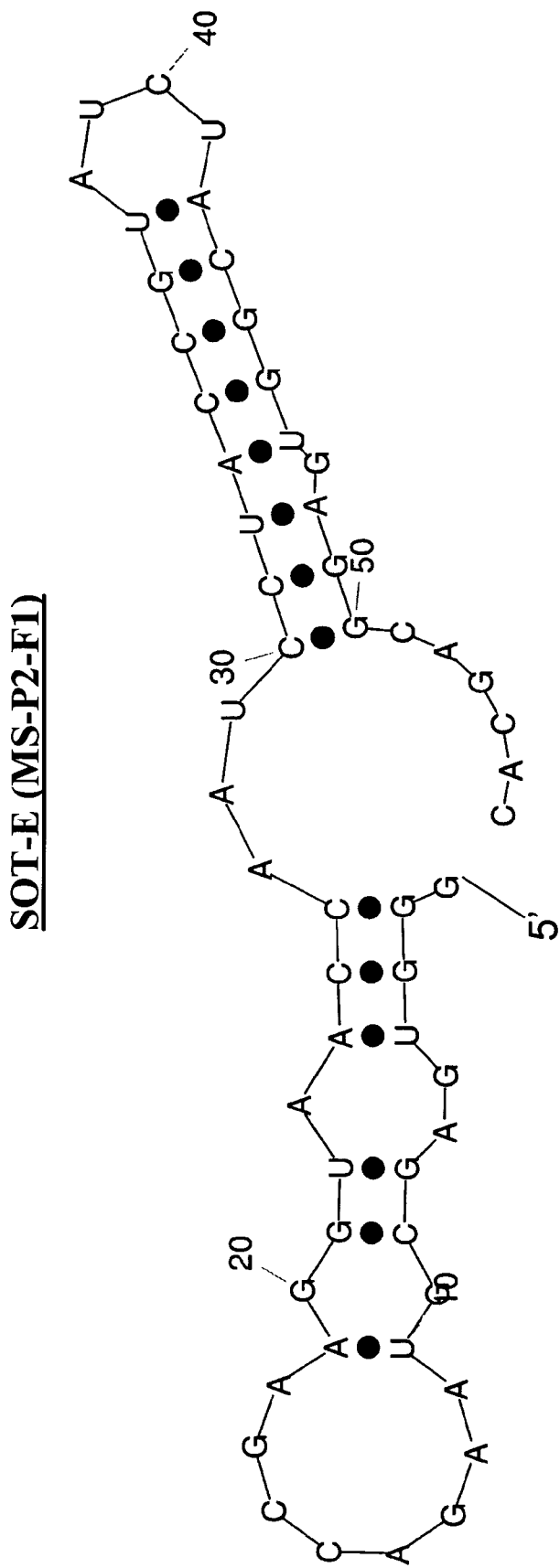

FIG. 12 shows calculated secondary structure of ghrelin binding RNA Spiegelmer clone SOT-E (SEQ ID NO: 33), the secondary structure was calculated with the program "RNAfold" (Hofacker et al., 1994, Monatsh. Chem 125:167-188).

FIG. 13 shows binding analysis of truncated variants of Spiegelmers SOT-E tested by cell culture experiments.

Figure 14:
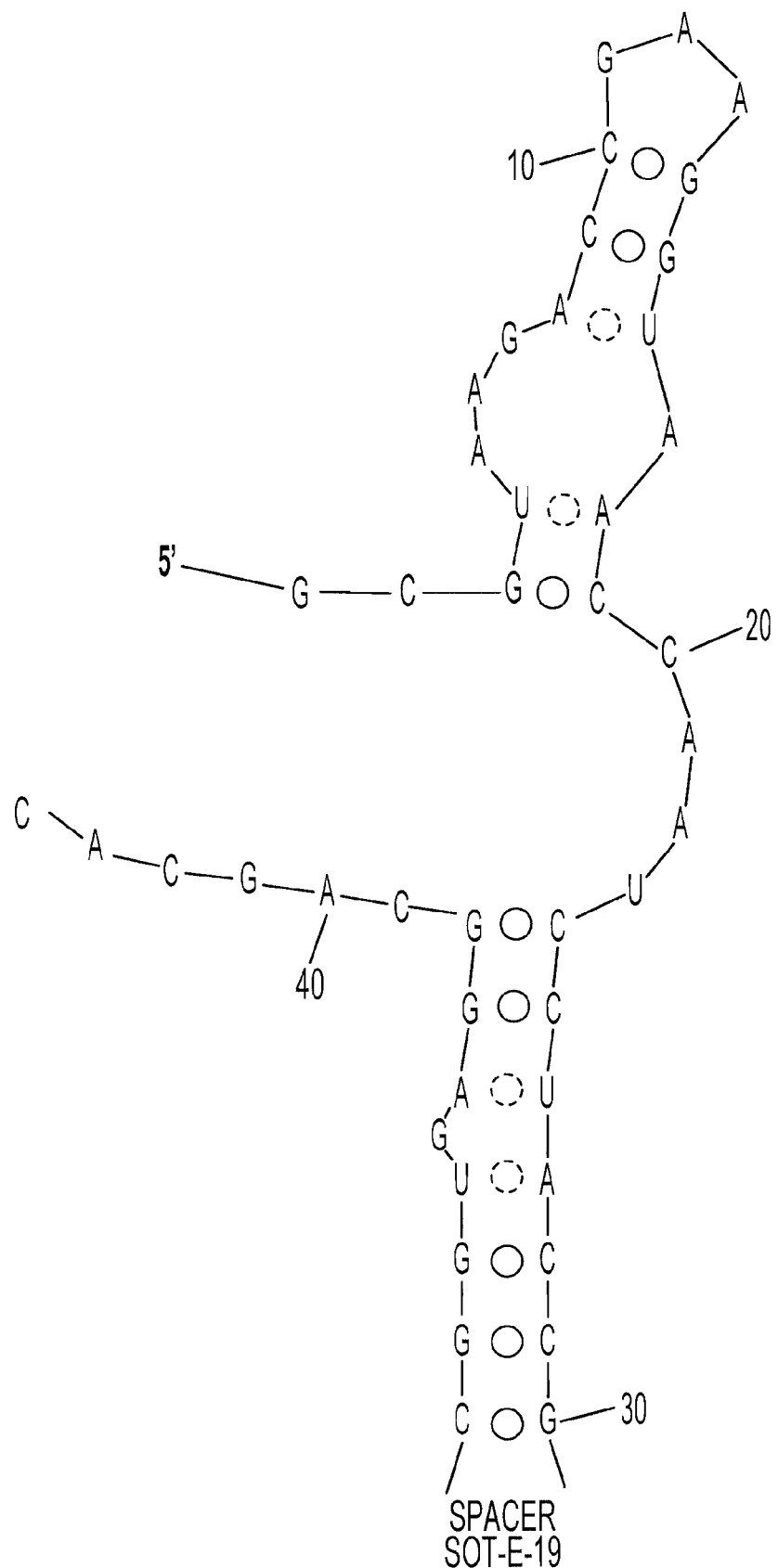

FIG. 14 shows a presumptive secondary structure of ghrelin binding RNA
Spiegelmer SOT-E-19 (SEQ ID NOS. 75 and 82).

Figure 15:
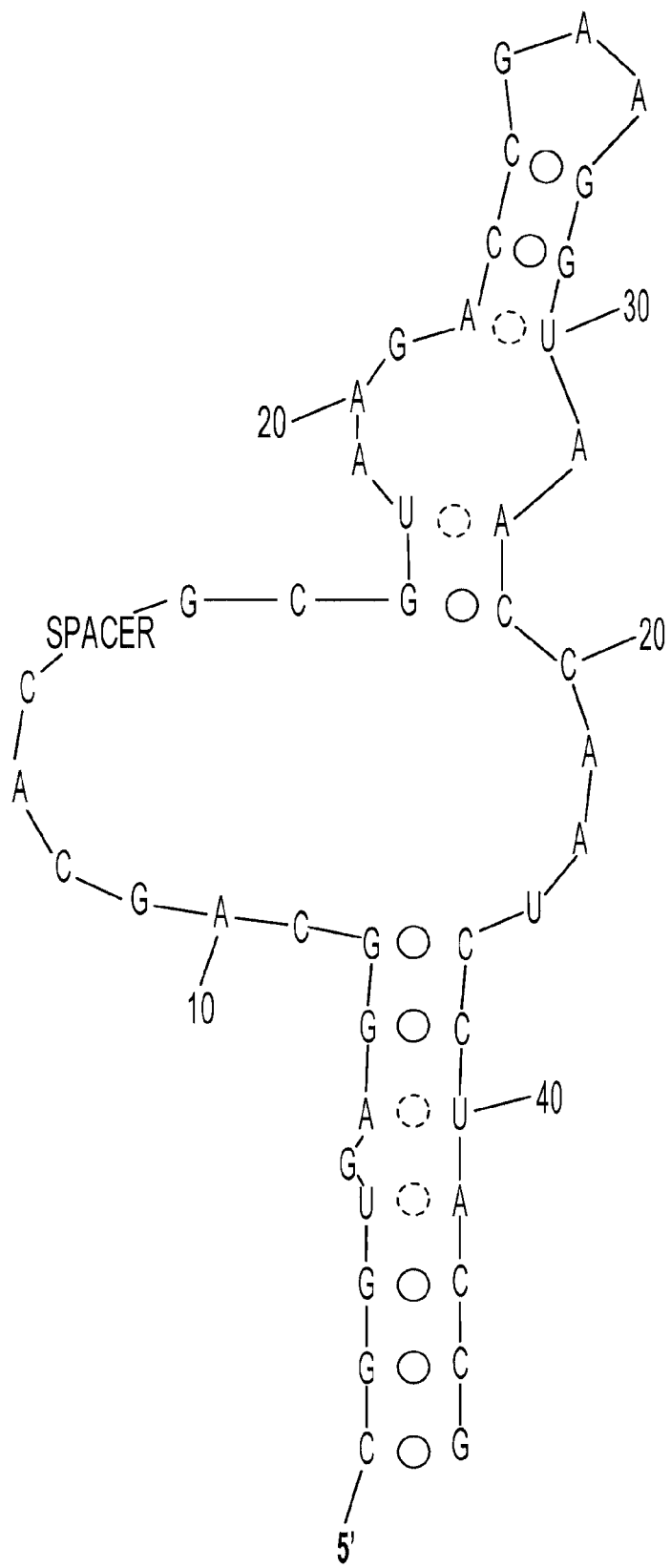

FIG. 15 shows a presumptive secondary structure of ghrelin binding RNA spiegelmer clone SOT-E-21 (SEQ ID NOS. 76 and 83).

Figure 16:
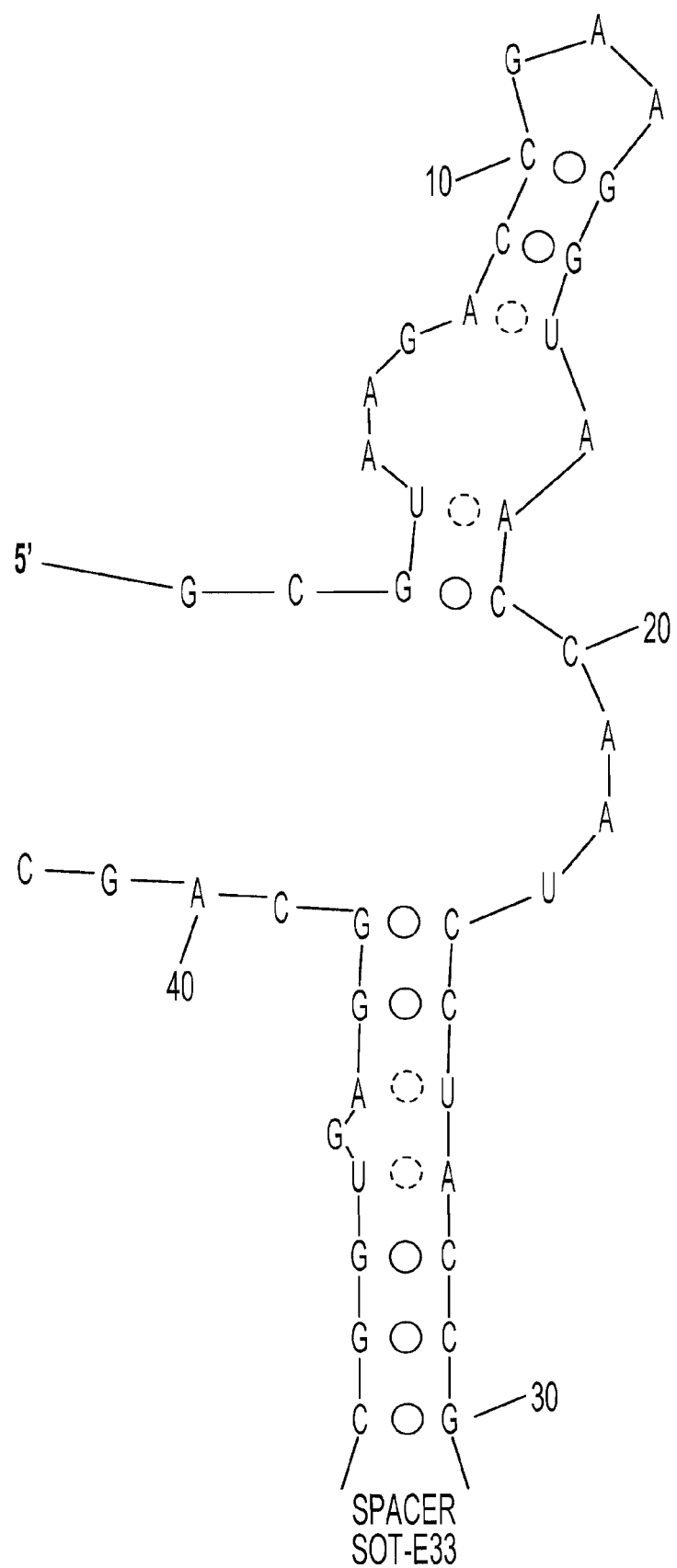

FIG. 16 shows a presumptive secondary structure of ghrelin binding RNA spiegelmer clone SOT-E-33 (SEQ ID NOS. 78 and 85).

Figure 17:
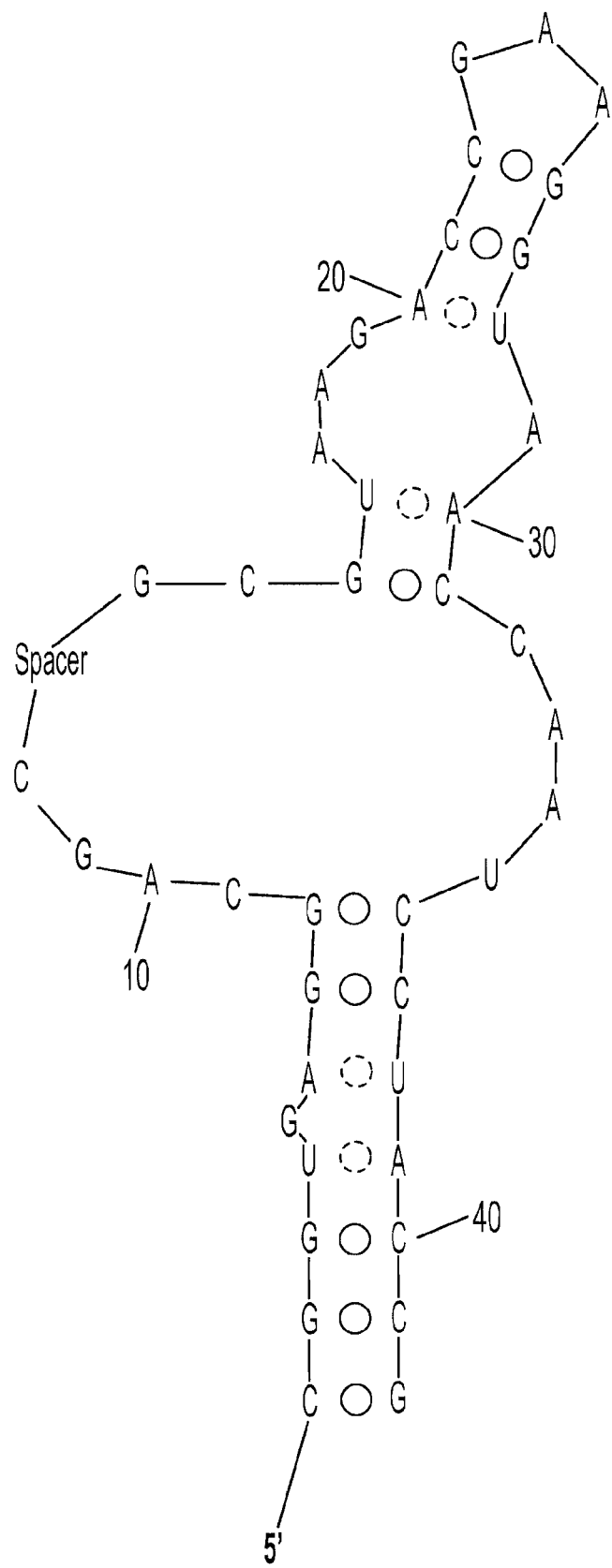

FIG. 17 shows a presumptive secondary structure of ghrelin binding RNA spiegelmer clone SOT-E-25 (SEQ ID NOS. 77 and 84).

Figure 18:
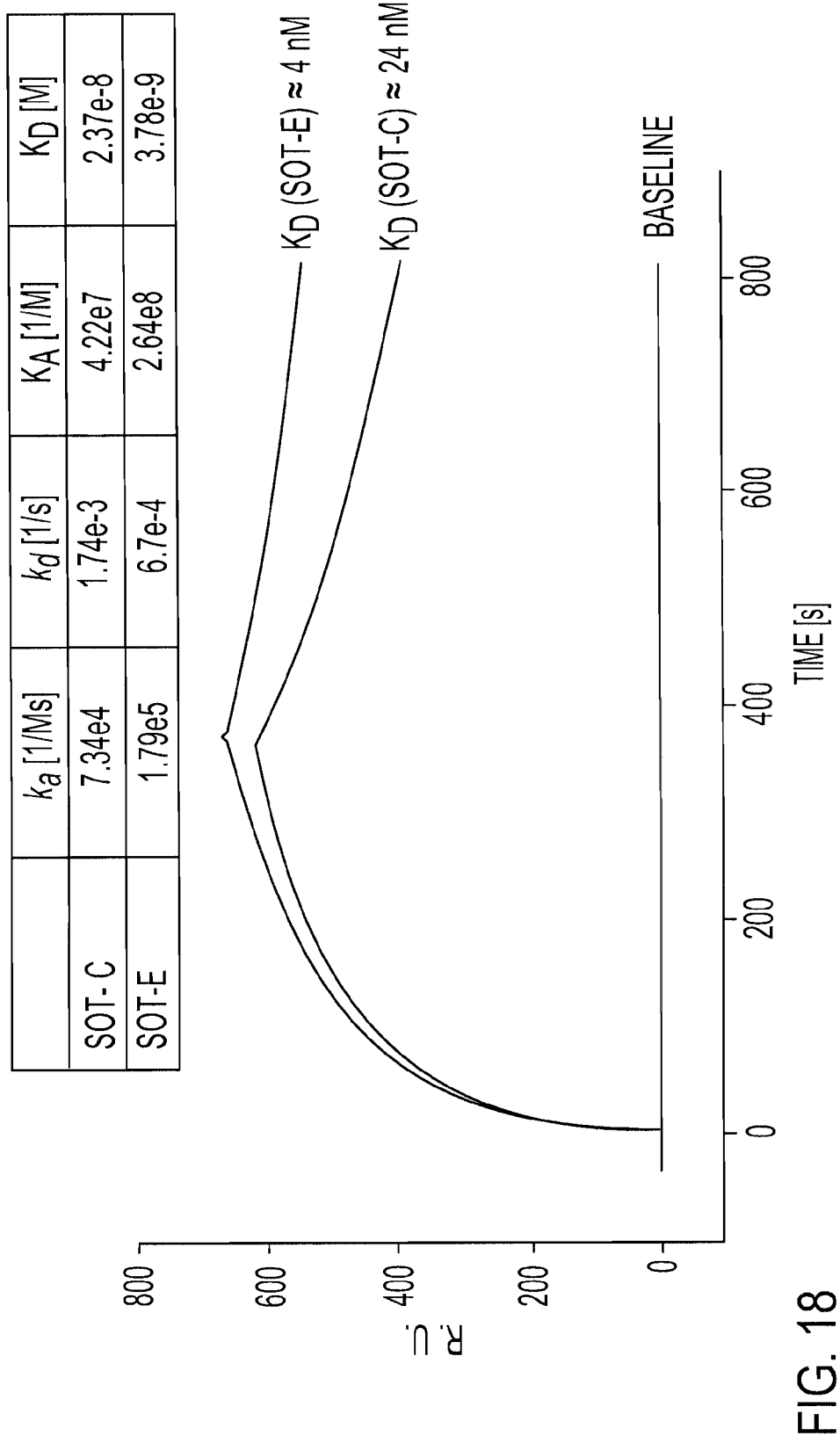
Figure 19:
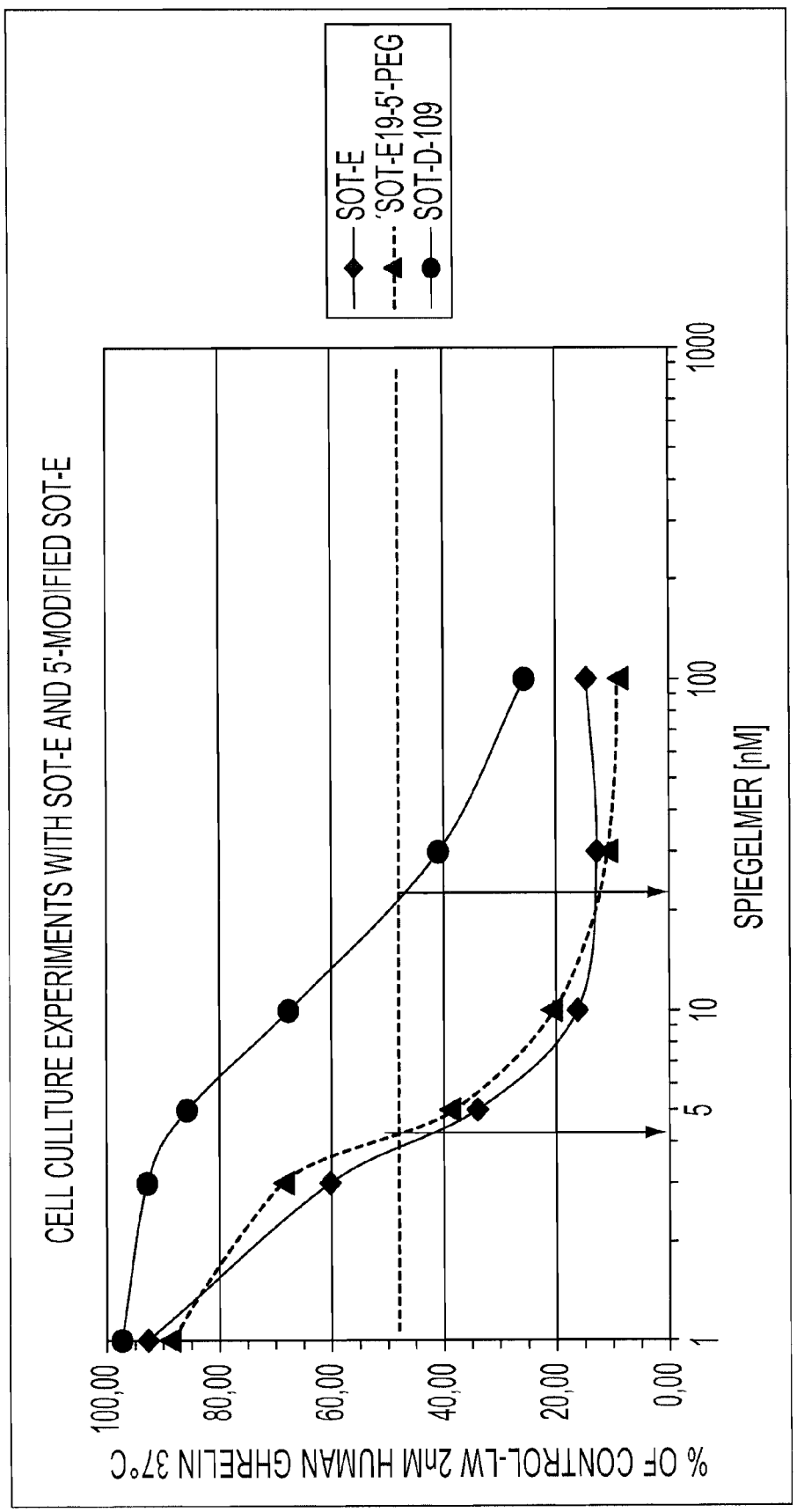
Figure 20:
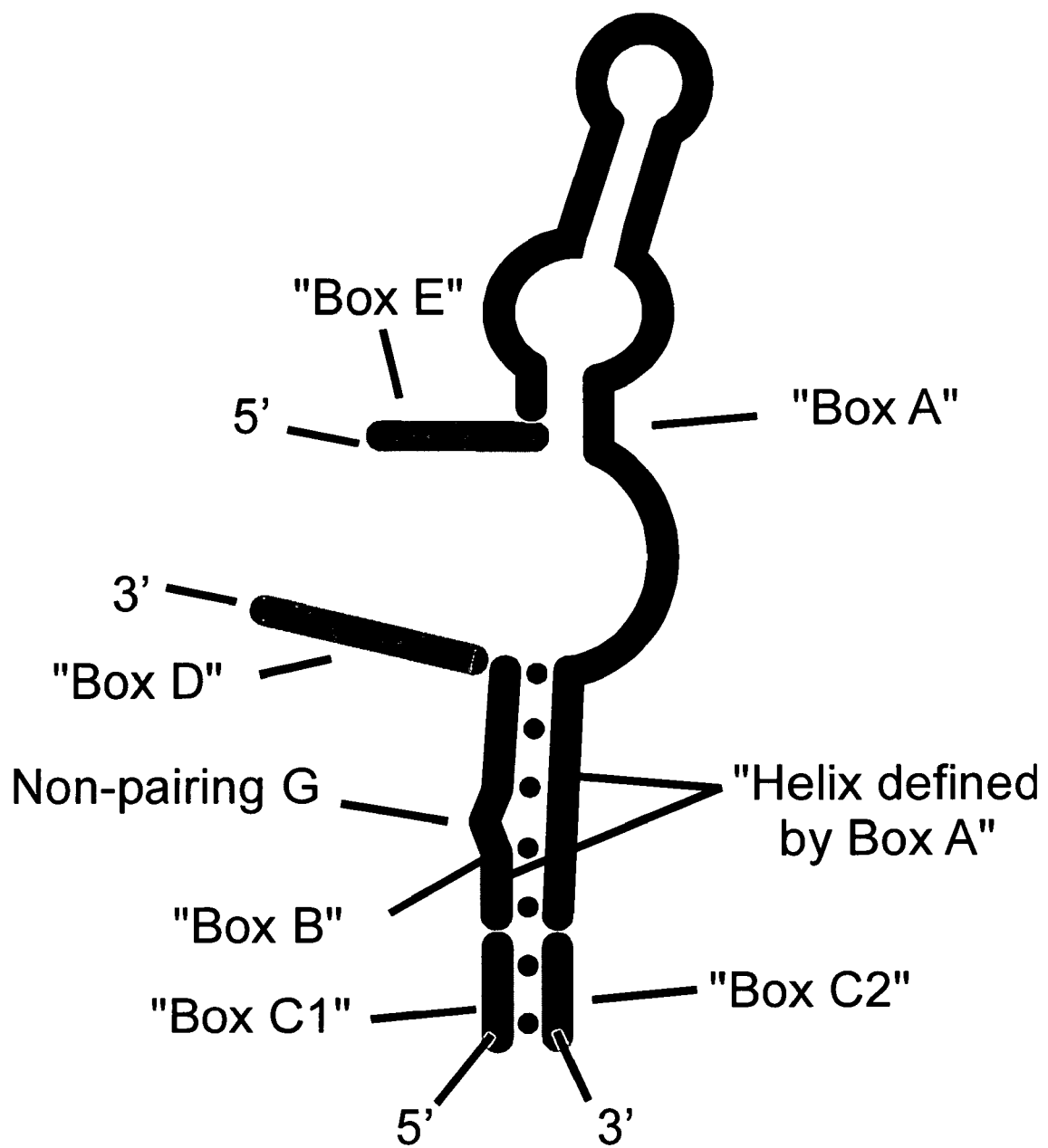
Figure 20:
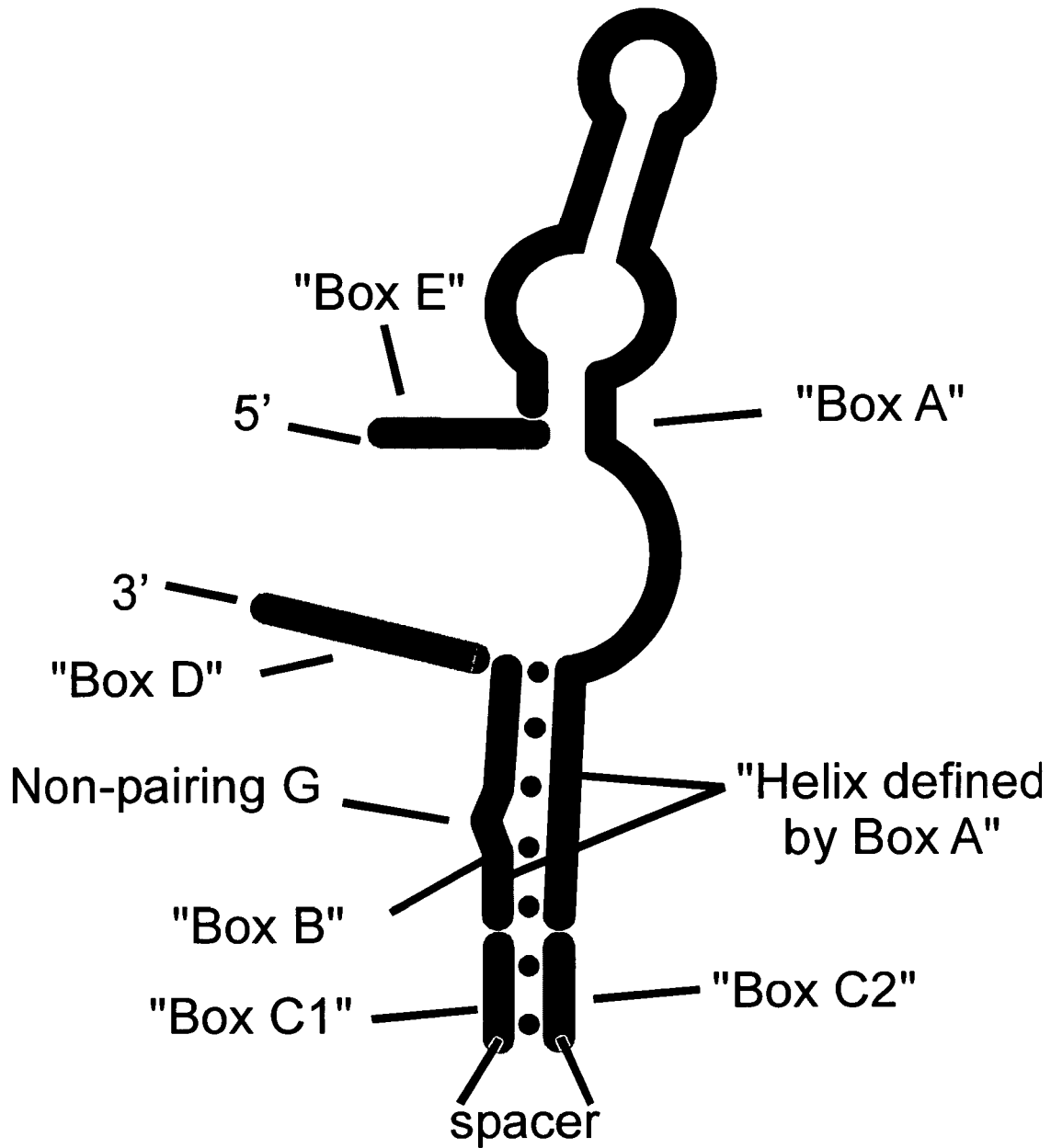
Figure 20:
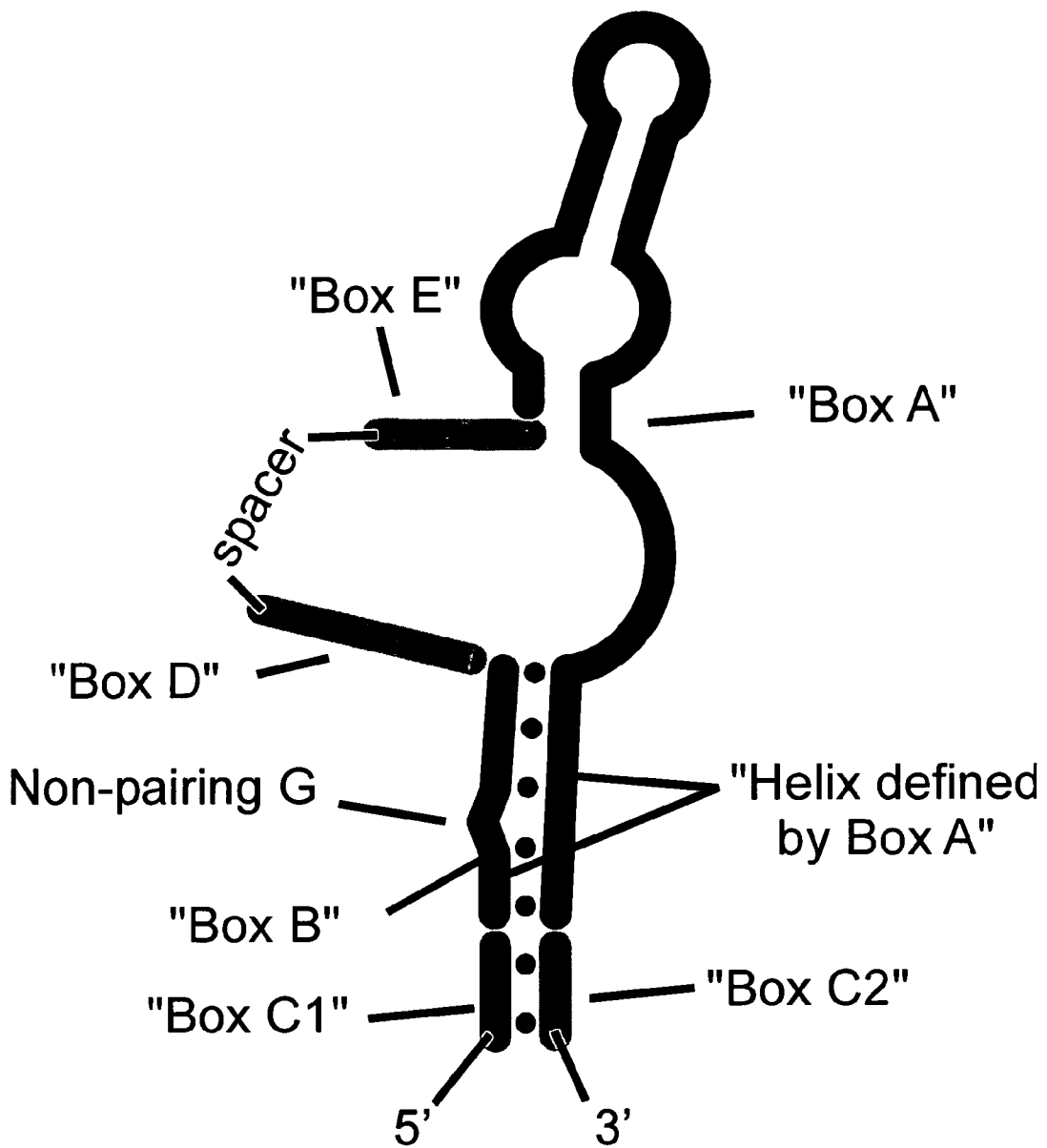
Figure 20:
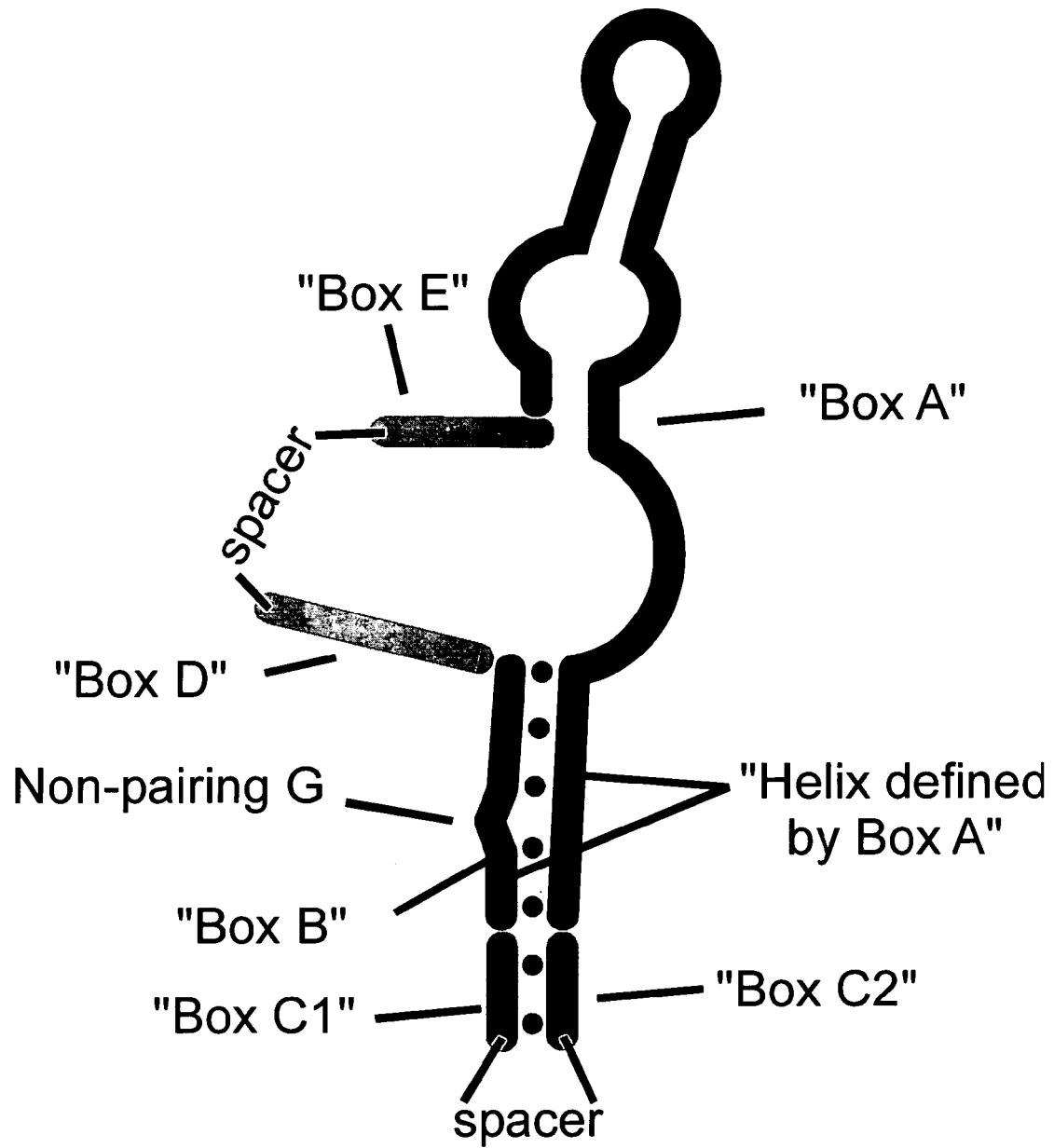

FIG. 18 shows the Biacore 2000 sensorgrams indicating the $K_D$ values of D-ghrelin binding RNA clones SOT-C and SOT-E;

FIG. 19 shows a dose-response curve for the inhibition of ghrelin-induced $Ca^{++}$-release by Spiegelmer SOT-E, SOT-E-19-5 '-Amino, SOT-E-19-5'-PEG or SOT-D-109 at 37° C.; cells were stimulated with 2 nM human ghrelin preincubated at 37° C. with various amounts of Spiegelmer SOT-E, SOT-E-19-5'-Amino, SOT-E-19-5 '-PEG or SOT-D-109; the results show the percentage of fluorescence signal normalized to the signal obtained with no Spiegelmer; Spiegelmer SOT-E-19 and its modified versions were found to inhibit ghrelin-induced $Ca^{++}$-release with an $IC_{50}$ of about 4 nM;

FIG. 20A shows the definition of the sequence boxes which are characteristic for ghrelin binding Spiegelmers;

FIG. 20B one variant of FIG. 20A;

FIG. 20C one variant of FIG. 20A;

FIG. 20D one variant of FIG. 20A;

FIG. 21 shows the sequences of SOT-D-109 (SEQ ID NO:30), SOT-E (SEQ ID NO:33), SOT-E-19 (SEQ ID NOS: 75 and 82), SOT-E-21 (SEQ ID NOS:76 and 83), SOT-E-33 (SEQ ID NOS:78 and 85) and SOT-E-25 (SEQ ID NOS:77 and 84), where "S"=Spacer.

Figure 22:
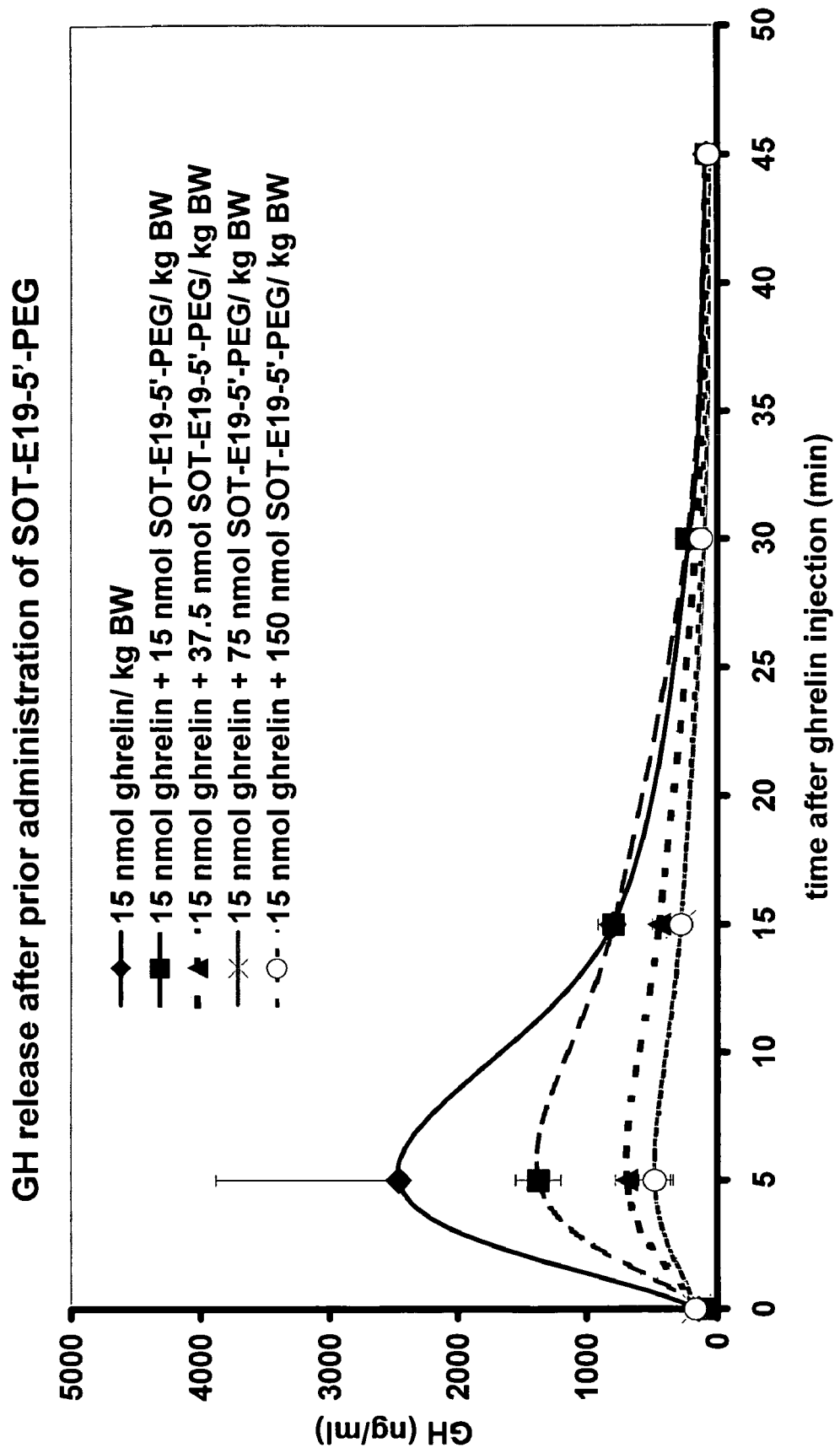

FIG. 22 shows the inhibition of growth hormone release after exogenous ghrelin administration by anti-ghrelin Spiegelmer SOT-E19-5'-PEG.

FIG. 23 shows an overview of different derivatives of SOT-E-19 which comprise additional nucleotides instead of the internal linker, and the observed $IC_{50}$ value expressed in nM. In FIG. 23 the sequences are shown in the Sequence Listing with the following sequence identifiers:

| SEQ ID NO: | Sequence |
|---|---|
| 33 | SOT-E |
| 75 and 82 | SOT-E-19 |
| 43 | SOT-E19-L |
| 44 | SOT-E19-L1 |
| 45 | SOT-E19-L2 |
| 46 | SOT-E19-L3 |
| 47 | SOT-E19-L4 |
| 48 | SOT-E19-L5 |
| 49 | SOT-E19-L6 |
| 50 | SOT-E19-L7 |

Figure 24:
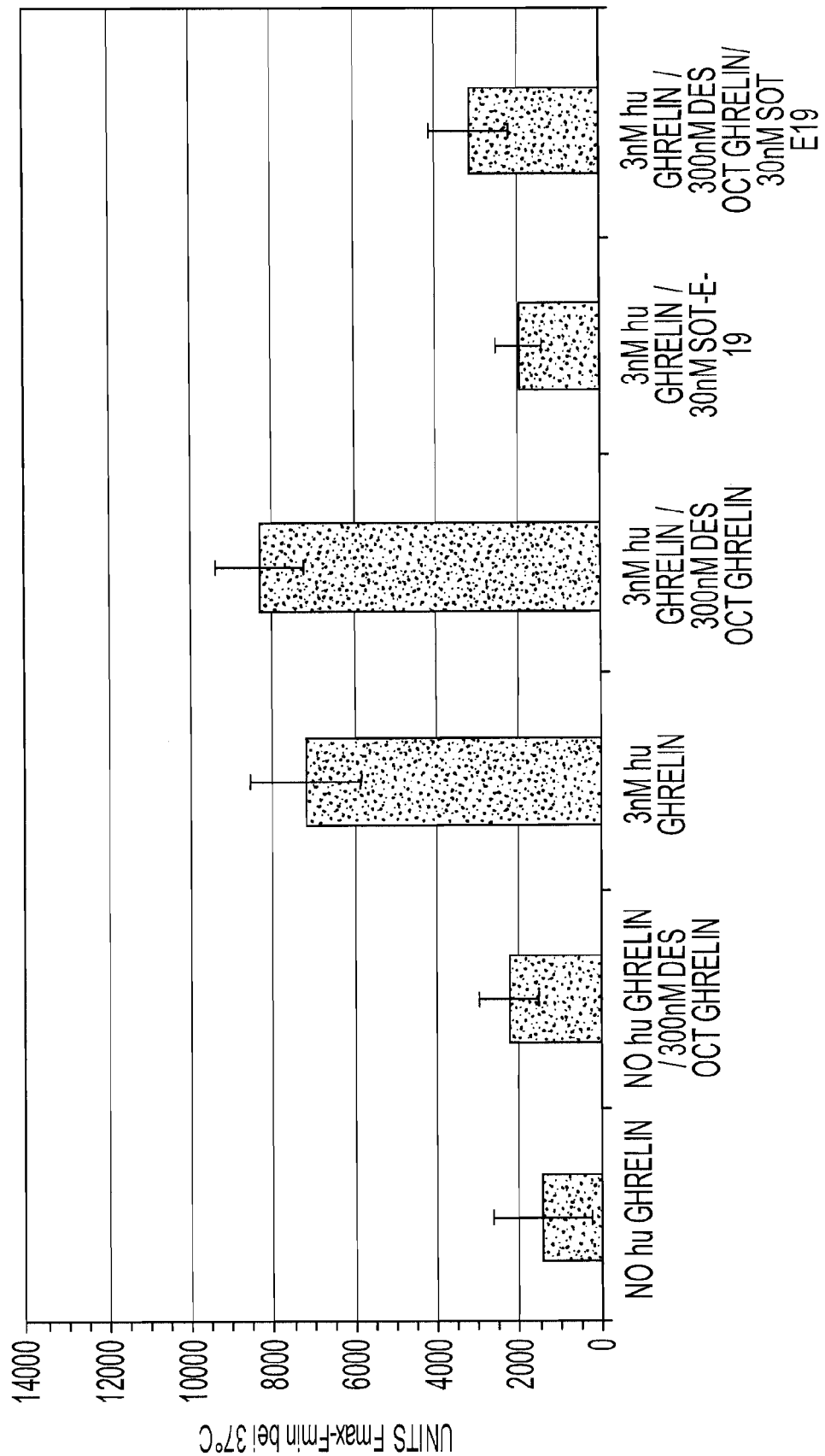

FIG. 24 shows the result of a cellular competition assay with octanoyl-ghrelin, des-octanoyl-ghrelin, and Spiegelmer SOT-E-19, with combinations and concentrations of the components summarized below the bars.

Figure 25:
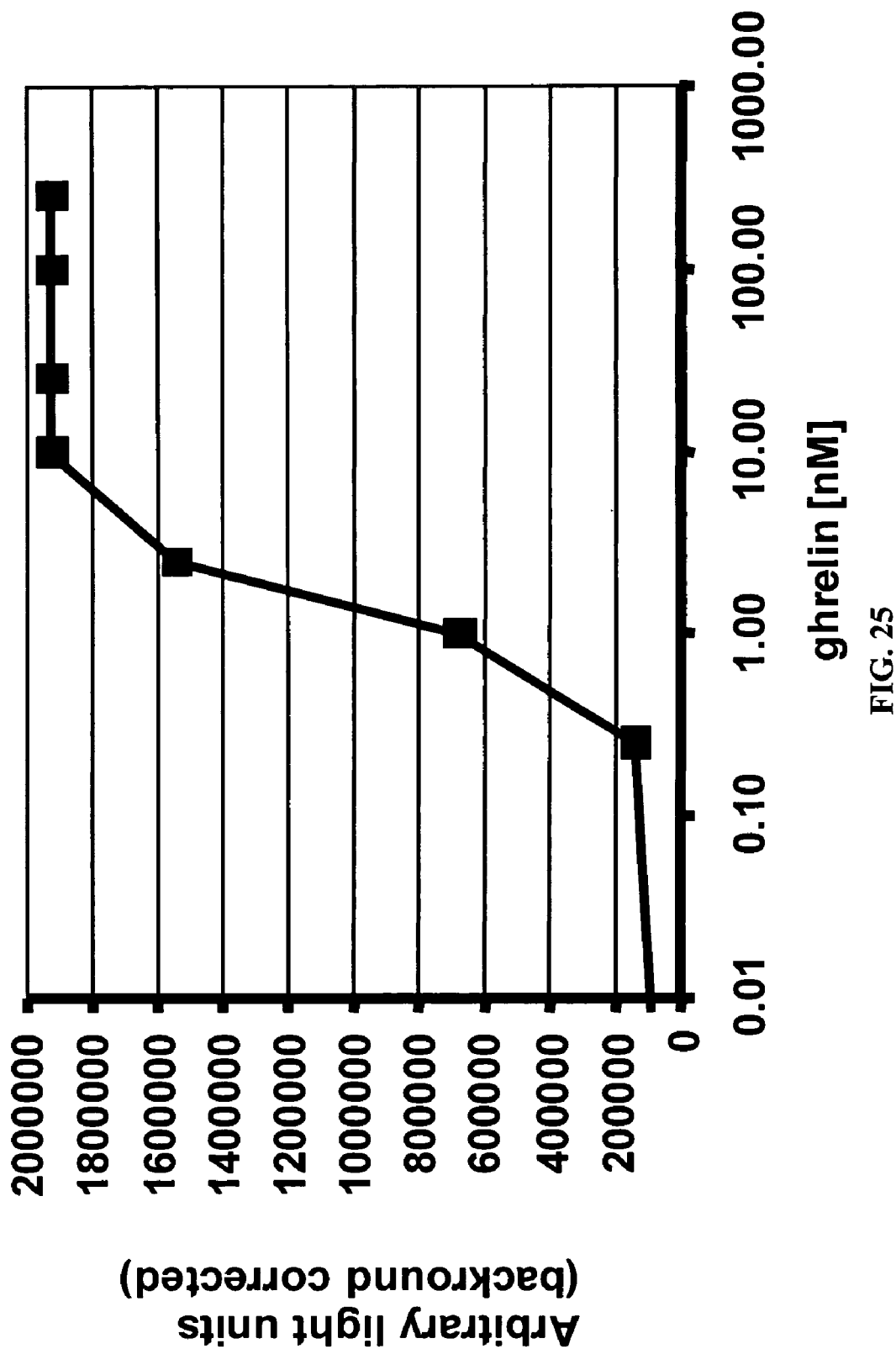

FIG. 25 shows a standard curve of absorbance versus human ghrelin (octanoylated) concentration recorded by an EIA type detection assay whereas the ghrelin-binding Spiegelmer NOX-B11 was used to immobilize human ghrelin (octanoylated) thus allowing the quantification of human ghrelin (octanoylated).

FIGS. 26A-D shows various steps of method for quantification of octanoyl-ghrelin using a ghrelin binding nucleic acid according to the present invention.

DETAILED DESCRIPTION OF THE INVENTION

The present invention is based on the surprising finding that it is possible to generate nucleic acids binding specifically and with high affinity to ghrelin. More specifically, the present inventors could surprisingly generate nucleic acids specifically binding to bioactive ghrelin, and more preferably octanoyl ghrelin and most preferably n-octanoyl ghrelin.

Ghrelin is a basic peptide having the amino acid sequence according to SEQ. ID. No. 1, and is preferably modified with a fatty acid side chain which is preferably an octanoyl side chain and more preferably a n-octanoyl side chain. The calculated pI of ghrelin is 11.07 for human ghrelin and 10.56 for rat ghrelin. In a preferred embodiment the ghrelin to which the nucleic acids according to the present invention bind, is a ghrelin which is modified with the fatty acid side chain. In an alternative embodiment the ghrelin is a ghrelin which does not have the fatty acid side chain. As used herein the term ghrelin refers to any ghrelin including, but not limited to, mammalian ghrelin. Preferably, the mammalian ghrelin is selected from the group comprising mice, rat, rabbit, hamster and human ghrelin. Most preferably the ghrelin is human ghrelin.

The finding that high affinity binding nucleic acids to ghrelin could be identified, is insofar surprising as Eaton et al.

(Eaton, B. E.; Gold, L.; Hicke, B. J.; Janjic, N.; Jucker, F. M.; Sebosta, D. P.; Tarasow, T. M.; Willis, M. C.; Zichi, D. A.; Bioorganic & Medicinal Chemistry, Vol 5, No. 6; pp 1087-1096, 1997) observed that the generation of aptamers, i.e. D-nucleic acids binding to a target molecule, directed to a basic protein is in general very difficult because this kind of target produces a high but non-specific signal-to-noise ratio. This high signal-to-noise ratio results from the high non-specific affinity shown by nucleic acids for basic targets such as ghrelin.

It is an even more surprising finding that despite of the very basic over-all pI of ghrelin and the receptor binding motif GSSFL [ghrelin (1-5)] (SEQ ID NO: 1, amino acids 1-5) of ghrelin being a rather acidic domain with a calculated pI of 5.5, the present inventors could identify a nucleic acid using the full-length ghrelin that specifically recognizes the acidic receptor binding domain, but not the basic central and carboxy-terminal domain of the peptide. This is surprising in regard of electrostatic effects of both the charges of target molecule, i. e. ghrelin, and the charges of the nucleic acid. The binding of negatively charged nucleic acids to a basic domain of a target molecule should be much more advantageous compared to the binding of a nucleic acid to an acidic domain of a target molecule. Thus it has to be pointed out that the one skilled in the art had no reasonable expectation of success to select a nucleic acid ligand that is not binding to the basic part of ghrelin but is binding to the acidic domain of the target molecule.

Besides having the amino-terminal receptor binding motif GSSFL (SEQ ID NO: 1, amino acids 1-5), a biologically active ghrelin which is also referred to herein as bioactive ghrelin, is preferably characterized by its acylation with a n-octanoly group at amino acid serine 3. The nucleic acid molecules according to the present invention which are preferably a ligand of the amino-terminal motif GSSFL disclosed herein preferably allow the discrimination of the biologically active from the bio-inactive or non-bioactive form of ghrelin. This is surprising, since binding is strictly dependent on the presence of two moieties, the octanoyl group and the peptide: binding of the nucleic acid to octanoyl-ghrelin is specific in the presence of a 1000-fold excess of desoctanoyl-ghrelin, more preferable in the presence in a 100-fold excess of desoctanoyl-ghrelin, and most preferable in the presence of a 10-fold excess of desoctanoyl-ghrelin.

As used in preferred embodiments herein, a bioactive ghrelin is a ghrelin which exhibits in a preferred embodiment essentially all of the characteristics of the naturally occurring ghrelin. Particularly, a bioactive ghrelin as used herein in preferred embodiments is any ghrelin and ghrelin derivative which is responsible for or can trigger the release of growth hormone, more preferably via an interaction with the GHS receptor. In contrast to this in preferred embodiments a non-bioactive ghrelin is a ghrelin which is different from bioactive ghrelin, more preferably does not trigger the release of growth hormone, more preferably via an interaction with the GHS receptor.

In a preferred embodiment the present inventors were surprisingly able to generate ghrelin binding nucleic acids, whereby the ghrelin is a bioactive ghrelin or biologically active ghrelin which discriminate between ghrelin having the octanoyl acid side chain at a third amino acid of its N terminus (serine 3) whilst they are not binding to ghrelin lacking such octanoyl acid side chain.

The features of the nucleic acid according to the present invention as described herein can be realised in any aspect of the present invention where the nucleic acid is used, either alone or in any combination.

Without wishing to be bound by any theory, the present inventors assume that the observed specificity of the ghrelin binding nucleic acids according to the present invention share some structural features which shall be discussed in the following, whereby reference is made to FIG. 20A. However, it is to be understood that FIG. 20A incorporates several of said structural features which do not have to be necessarily realized in each and any of the nucleic acids according to the present invention.

The basic structural feature is a first stretch of contiguous nucleotides which is also referred to herein as Box A or first stretch Box A herein, and a second stretch of contiguous nucleotides which is also referred to as Box B or second stretch Box B herein. The first stretch Box A comprises about 25 consecutive nucleotides, whereas the second stretch Box B comprises about six to eight consecutive nucleotides. The 3'terminal stretch of the first stretch Box A hybridises with the second stretch Box B, whereby upon hybridisation a first double-stranded structure is formed, whereby such first double-stranded structure comprises a bulge. The double-stranded structure is formed by the five 3'-terminal consecutive nucleotides of the first stretch Box A and some of the six to eight consecutive nucleotides of the second stretch Box B. The bulge is formed by as little as 1 and as many as 3 nucleotides which are not base-pairing with the five 3'-terminal consecutive nucleotides of the first stretch Box A. Therefore, the bulge may consist of 1, 2 or 3 non-base-pairing nucleotides, preferably provided by the second stretch Box B. In view of this bulge size, the second stretch Box B may comprise 6 to 8 consecutive nucleotides. More preferably, the bulge is created by a non-base pairing third nucleotide within the second stretch Box B seen from the 5' end of the second stretch Box B with the second stretch Box B preferably comprising six consecutive nucleotides.

In a preferred embodiment the nucleic acid according to the present invention is a single nucleic acid molecule. In a further embodiment, the single nucleic acid molecule is present as a multitude of the single nucleic acid molecule. Preferably, the terms nucleic acid and nucleic acid molecule are used in an interchangeable manner herein if not indicated to the contrary.

It will be acknowledged by the ones skilled in the art that the nucleic acid molecule in accordance with the invention preferably consists of nucleotides which are covalently linked to each other, preferably through phosphodiester links or linkages.

A further important feature is a second double-stranded structure. Such second double-stranded structure is formed by a third stretch of contiguous nucleotides which is also referred to as Box C1 or third stretch Box C1, and by a fourth stretch of contiguous nucleotides which is also referred to as Box C2 or fourth stretch Box C2. The third stretch Box C1 is attached with its 3'-end to the 5'-end of the second stretch Box B, and the fourth stretch Box C2 is attached with its 5'-end to the 3'-end of the first stretch Box A. This second double-stranded structure typically forms a helical structure which is also referred to herein as the second helical structure. Such second helical structure is preferably an extension of the helical structure typically formed by the first double-stranded structure. The length of said first double-stranded structure which is preferably a helical structure also referred to herein as first helical structure, is defined by the length of the first stretch Box A and second stretch Box B, more precisely by the stretch of said two Boxes hybridising to each other. The extension provided to said first helical structure by the second double-stranded structure is, according to the current understanding of the inventors, more of a stabilising kind, although the present inventors do not wish to be bound by this theory. The second helical structure consists of one to ten base pairs, preferably one to three base pairs and more preferably two or three base pairs. It will be acknowledged by the one skilled in the art that as little as one to three base pairs are not necessarily suitable to create a helix. This kind of structure is thus also referred to herein as a helix-like structure, whereby preferably such helix-like structure is a structure which, when extended by one or several base pairs, would result in a helical structure.

A further important feature is a fifth stretch of consecutive nucleotides which is also referred to herein as Box D or the fifth stretch Box D. This additional stretch provides for an improvement in the overall binding of the nucleic acid. Although the fifth stretch comprises at least only two nucleotides, its beneficial impact on the binding of ghrelin can be further improved by increasing the length of the fifth stretch preferably up to 6 consecutive nucleotides. Also, the fifth stretch has turned out to be particularly effective is if contained, preferably at its 5' end a CA dinucleotide and the fifth stretch having sequence of 5'CA(X)$_n$3' whereby X is any nucleotide, preferably selected from the group comprising A, G, T, C, U and I.

A further feature of the nucleic acids according to the present invention is the sixth stretch of contiguous nucleotides which is also referred to herein as Box E or the sixth stretch Box E. Preferably, the sixth stretch consists of at least one nucleotide.

The various stretches are attached to each other as may be taken from FIG. 20A. As depicted there, preferably, the third stretch Box C1 and fourth stretch Box C2 each comprise one or two nucleotides, more preferably two nucleotides, fifth stretch Box D comprises at least two nucleotides, preferably four nucleotides and most preferably six nucleotides.

In the embodiment where the length of the third stretch Box C1 and fourth stretch Box C2 is 0, first stretch Box A and second stretch Box B may optionally be linked through a linker or spacer, whereby such spacer may be any of the spacers disclosed herein. As used herein the terms "spacer" and "linker" are used in an interchangeable manner if not indicated otherwise.

In connection with the present invention it is preferred that the first stretch and the second stretch are linked to each other, preferably through a covalent link. In a preferred embodiment, the covalent link is a phosphodiester link. In a still further preferred embodiment, the 3' terminus of the first stretch is linked to the 5' terminus of the second stretch.

In another embodiment the sixth stretch Box E comprises 1 to 10 consecutive nucleotides, preferably 1 to 4 consecutive nucleotides and most preferably 3 consecutive nucleotides.

As may be taken from these various arrangements, it is possible that the fifth stretch and the sixth stretch are linked to each other or not, that the third and fourth stretch are linked to each other or not and that the first and the second stretch are linked to each other or not. It will be acknowledged that the linkage is preferably made through a covalent bond. More preferably the linkage is made through a hydrophilic spacer comprising at least one, preferably a multitude of ethylene glycol moieties. Various linkers and spacers, respectively, are known to the ones skilled in the art and can be selected using the following criteria as described, e. g., by Pils and Micura (Nucleic Acid Research (2000), 28 (9), 1859-1863). The linkers should do not interfere with the base pairs themselves. Linker types that contain aromatic carbocycles stack on the terminal base pair and therefore are not suitable (J. Am. Chem. Soc. (1999), 121, 9905-9906; J. Am. Chem. Soc. (1998), 120, 11004-11005). However, eythylene glycol based or ethylene glycol derived linkers meet these requirements as they have the advantage of good water solubility and high conformational flexibility (J. Am. Chem. Soc. (1993), 115, 8483-8484; Nucleic Acids Research (1993), 21, 5600-5603; Biochemistry (1993), 32, 1751-1758; Nucleic Acid Research (1990), 18, 6353-6359; J. Am. Chem. Soc. (1997), 119, 11591-11597). Preferably, the spacer comprises or consists of one or several ethylene glycol moieties, whereby the oxygen is replaced or substituted by a $CH_2$, a phosphate or sulfur.

Based on these linkage options, the following structures can be realized

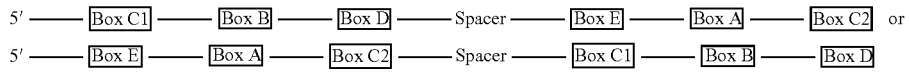

Finally it is also within the present invention that a fully closed, i.e. circular structure for the nucleic acids according to the present invention is realized as depicted in FIG. 20D.

The nucleic acids according to the present invention shall also comprise nucleic acids which are essentially homologous to the particular sequences disclosed herein. The term substantially homologous shall be understood such as the homology is at least 75%, preferably 85%, more preferably 90% and most preferably more that 95%, 96%, 97%, 98% or 99%.

The term inventive nucleic acid or nucleic acid according to the present invention shall also comprise those nucleic acids comprising the nucleic acids sequences disclosed herein or part thereof, preferably to the extent that the nucleic acids or said parts are involved in the binding to ghrelin, and more preferably discriminate bioactive ghrelin from non-bioactive ghrelin, i. e. in particular octanoyl-ghrelin from des-octanoyl-ghrelin. Such a nucleic acid may be derived from the ones disclosed herein, e.g., by truncation. Truncation may be related to either or both of the ends of the nucleic acids as disclosed herein. Also, truncation may be related to the inner sequence of nucleotides, i.e. it may be related to the nucleotide(s) between the 5' and the 3' terminal nucleotide, respectively. Moreover, truncation shall comprise the deletion of as little as a single nucleotide from the sequence of the nucleic acids disclosed herein. Truncation may also be related to more than one stretch of the inventive nucleic acid(s), whereby the stretch can be as little as one nucleotide long.

The nucleic acids according to the present invention may be either D-nucleic acids or L-nucleic acids. Preferably, the inventive nucleic acids are L-nucleic acids. In addition it is possible that one or several parts of the nucleic acid are present as D-nucleic acids or at least one or several parts of the nucleic acids are L-nucleic acids. The term "part" of the nucleic acids shall mean as little as one nucleotide. Such nucleic acids are generally referred to herein as D- and L-nucleic acids, respectively. Therefore, in a particularly preferred embodiment, the nucleic acids according to the present invention consist of L-nucleotides and comprise at least one D-nucleotide. Such D-nucleotide is preferably attached to a part different from the stretches defining the nucleic acids according to the present invention, preferably those parts thereof, where an interaction with other parts of the nucleic acid is involved. Preferably, such D-nucleotide is attached at a terminus of any of the stretches and of any nucleic acid according to the present invention, respectively. In a further preferred embodiment, such D-nucleotides may act as a spacer or a linker, preferably attaching modifications such as PEG and HES to the nucleic acids according to the present invention.

It is also within the present invention that the nucleic acids according to the present invention are part of a longer nucleic acid whereby this longer nucleic acid comprises several parts whereby at least one part is a nucleic acid, or a part thereof, according to the present invention. The other part of these longer nucleic acids can be either a D-nucleic acid or L-nucleic acid. Any combination may be used in connection with the present invention. These other part(s) of the longer nucleic acid can exhibit a function which is different from binding, preferably from binding to ghrelin. One possible function is to allow interaction with other molecules, whereby such other molecules preferably are different from ghrelin, such as, e.g., for immobilization, cross-linking, detection or amplification.

L-nucleic acids as used herein are nucleic acids consisting of L-nucleotides, preferably consisting completely of L-nucleotides.

D-nucleic acids as used herein are nucleic acids consisting of D-nucleotides, preferably consisting completely of D-nucleotides.

Irrespective of whether the inventive nucleic acid consists of D-nucleotides, L-nucleotides or a combination of both with the combination being e.g. a random combination or a defined sequence of stretches consisting of at least one L-nucleotide and at least one D-nucleic acid, the nucleic acid may consist of desoxyribonucleotide(s), ribonucleotide(s) or combinations thereof.

Designing the inventive nucleic acids as L-nucleic acid is advantageous for several reasons. L-nucleic acids are enantiomers of naturally occurring nucleic acids. D-nucleic acids, however, are not very stable in aqueous solutions and particularly in biological systems or biological samples due to the widespread presence of nucleases. Naturally occurring nucleases, particularly nucleases from animal cells are not capable of degrading L-nucleic acids. Because of this the biological half-life of the L-nucleic acid is significantly increased in such a system, including the animal and human body. Due to the lacking degradability of L-nucleic acid no nuclease degradation products are generated and thus no side effects arising therefrom observed. This aspect delimits the L-nucleic acid of factually all other compounds which are used in the therapy of diseases and/or disorders involving the presence of ghrelin. L-nucleic acids which specifically bind to a target molecule through a mechanism different from Watson Crick base pairing, or aptamers which consists partially or completely of L-nucleotides, particularly with those parts of the aptamer being involved in the binding of the aptamer to the target molecule, are also called spiegelmers.

It is also within the present invention that the inventive nucleic acids, regardless whether they are present as D-nucleic acids, L-nucleic acids or D,L-nucleic acids or whether they are DNA or RNA, may be present as single stranded or double stranded nucleic acids. Typically, the inventive nucleic acids are single stranded nucleic acids which exhibit defined secondary structures due to the primary sequence and may thus also form tertiary structures. The inventive nucleic acids, however, may also be double stranded in the meaning that two strands which are complementary or partially complementary to each other are hybridised to each other. This confers stability to the nucleic acid which, in particular, will be advantageous if the nucleic acid is present in the naturally occurring D-form rather than the L-form.

The inventive nucleic acids may be modified. Such modifications may be related to the single nucleotide of the nucleic acid and are well known in the art. Examples for such modification are described in, among others, Venkatesan N. et al. (2003) Curr Med Chem. October;10(19):1973-91; Kusser, W. (2000) J Biotechnol, 74: 27-38; Aurup, H. et al. (1994) *Nucleic Acids Res*, 22, 20-4; Cummins, L. L. et al, (1995) *Nucleic Acids Res*, 23, 2019-24; Eaton, B. E. et al. (1995) *Chem Biol*, 2, 633-8; Green, L. S. et al., (1995) *Chem Biol*, 2, 683-95; Kawasaki, A. M. et al., (1993) *J Med Chem*, 36, 831-41; Lesnik, E. A. et al., (1993) *Biochemistry*, 32, 7832-8; Miller, L. E. et al., (1993) *J Physiol*, 469, 213-43. Such modification can be a H atom, a F atom or O—CH3 group or NH2-group at the 2' position of the individual nucleotide of which the nucleic acid consists. Also, the nucleic acid according to the present invention can comprises at least one LNA nucleotide. In an embodiment the nucleic acid according to the present invention consists of LNA nucleotides.

In an embodiment, the nucleic acids according to the present invention may be a multipartite nucleic acid. A multipartite nucleic acid as used herein, is a nucleic acid which consists of at least two nucleic acid strands. These at least two nucleic acid strands form a functional unit whereby the functional unit is a ligand to a target molecule. The at least two nucleic acid strands may be derived from any of the inventive nucleic acids by either cleaving the nucleic acid to generate two strands or by synthesising one nucleic acid corresponding to a first part of the inventive, i.e. overall nucleic acid and another nucleic acid corresponding to the second part of the overall nucleic acid. It is to be acknowledged that both the cleavage and the synthesis may be applied to generate a multipartite nucleic acid where there are more than two strands as exemplified above. In other words, the at least two nucleic acid strands are typically different from two strands being complementary and hybridising to each other although a certain extent of complementarity between the various nucleic acid parts may exist.

The present inventors have discovered that the nucleic acids according to the present invention exhibit a very favourable Kd value range. More particularly, oligonucleotides comprising—besides complete Box A and Box B—Box C1 and C2 with minimal two nuclotides each, Box D with minimal six nucleotides and Box E with minimal three nucleotides (for example SOT-E) show sixfold better binding affinity to ghrelin (FIG. 18) than SOT-C.

A possibility to determine the binding constant is the use of the so called biacore device, which is also known to the one skilled in the art. Affinity as used herein was also measured by the use of "equilibrium assay" as described in the examples. An appropriate measure in order to express the intensity of the binding between the nucleic acid according to the target which is in the present case ghrelin, is the so-called Kd value which as such as well the method for its determination are known to the one skilled in the art.

The nucleic acids according to the present invention are characterized by a certain Kd value. Preferably, the Kd value shown by the nucleic acids according to the present invention is below 1 μM. A Kd value of about 1 μM is said to be characteristic for a non-specific binding of a nucleic acid to a target. As will be acknowledged by the ones in the art, the Kd value of a group of compounds such as the nucleic acids according to the present invention are within a certain range. The above-mentioned Kd of about 1 μM is a preferred upper limit for the Kd value. The preferred lower limit for the Kd of target binding nucleic acids can be about 10 picomolar or higher. It is within the present invention that the Kd values of individual nucleic acids binding to ghrelin is preferably within this range. Preferred ranges can be defined by choosing any first number within this range and any second number within this range. Preferred upper values are 0.25 μM, 0.1 μM and 0.01 μM, preferred lower values are 100 nM, 10 nM, 1 nM and 0.05 nM.

The nucleic acid molecules according to the present invention may have any length provided that they are still able to bind to the target molecule, and discriminate bioactive ghrelin from non-bioactive ghrelin, i. e. preferably octanoyl-ghrelin from desoctanoyl-ghrelin. It will be acknowledged in the art that there are preferred lengths of the nucleic acids according to the present inventions. Typically, the length is between 15 and 120 nucleotides. It will be acknowledged by the ones skilled in the art that any integer between 15 and 120 is a possible length for the nucleic acids according to the present invention. More preferred ranges for the length of the nucleic acids according to the present invention are lengths of about 20 to 100 nucleotides, about 20 to 80 nucleotides, about 20 to 60 nucleotides, about 20 to 50 nucleotides and about 30 to 50 nucleotides.

It is within the present invention that the nucleic acids disclosed herein comprise a moiety which preferably is a high molecular weight moiety and/or which preferably allows to modify the characteristics of the nucleic acid in terms of, among others, residence time in the animal body, preferably the human body. A particularly preferred embodiment of such modification is PEGylation and HESylation of the nucleic acids according to the present invention. As used herein PEG stands for poly(ethylene glycole) and HES for hydroxyethly starch. PEGylation as preferably used herein is the modification of a nucleic acid according to the present invention whereby such modification consists of a PEG moiety which is attached to a nucleic acid according to the present invention. HESylation as preferably used herein is the modification of a nucleic acid according to the present invention whereby such modification consists of a HES moiety which is attached to a nucleic acid according to the present invention. These modifications as well as the process of modifying a nucleic acid using such modifications, is described in European patent application EP 1 306 382, the disclosure of which is herewith incorporated in its entirety by reference.

Preferably, the molecular weight of a modification consisting of or comprising a high molecular weight moiety is about from 2,000 to 200,000 Da, preferably 40,000 to 120,000 Da, particularly in case of PEG being such high molecular weight moiety, and is preferably about from 3,000 to 100,000 Da, more preferably from 5,000 to 60,000 Da, particularly in case of HES being such high molecular weight moiety. The process of HES modification is, e.g., described in German patent application DE 1 2004 006 249.8 the disclosure of which is herewith incorporated in its entirety by reference.

Without wishing to be bound by any theory, it seems that by modifying the nucleic acids according to the present invention with high molecular weight moiety such as a polymer and more particularly the polymers disclosed herein, which are preferably physiologically acceptable, the excretion kinetic is changed. More particularly, it seems that due to the increased molecular weight of such modified inventive nucleic acids and due to the nucleic acids not being subject to metabolism particularly when in the L form, excretion from an animal body, preferably from a mammalian body and more preferably from a human body is decreased. As excretion typically occurs via the kidneys, the present inventors assume that the glomerular filtration rate of the thus modified nucleic acid is significantly reduced compared to the nucleic acids not having this kind of high molecular weight modification which results in an increase in the residence time in the body. In connection therewith it is particularly noteworthy that despite such high molecular weight modification the specificity of the nucleic acid according to the present invention is not affected in a detrimental manner. Insofar, the nucleic acids according to the present invention have surprising characteristics—which normally cannot be expected from pharmaceutically active compounds—such that a pharmaceutical formulation providing for a sustained release is not necessarily required to provide for a sustained release. Rather the nucleic acids according to the present invention in their modified form comprising a high molecular weight moiety, can as such already be used as a sustained release-formulation.

However, it is also within the present invention that the nucleic acids disclosed herein do not comprise any modification and particularly no high molecular weight modification such as PEGylation or HESylation. Such embodiment is particularly preferred when a fast clearance of the nucleic acids from the body after administration is desired. Such fast clearance might be desired in case of in vivo imaging or temporary appetite suppression using the nucleic acids or medicaments comprising the same, according to the present invention.

The inventive nucleic acids, which are also referred to herein as the nucleic acids according to the present invention, and/or the antagonists according to the present invention may be used for the generation or manufacture of a medicament. Such medicament contains at least one of the inventive nucleic acids, optionally together with further pharmaceutically active compounds, whereby the inventive nucleic acid preferably acts as pharmaceutically active compound itself. Such medicaments comprise in preferred embodiments at least a pharmaceutically acceptable carrier. Such carrier may be, e. g., water, buffer, PBS, glucose solution, preferably a 5% glucose salt balanced solution, starch, sugar, gelatine or any other acceptable carrier substance. Such carriers are generally known to the one skilled in the art.

In a further embodiment, the medicament comprises a further pharmaceutically active agent. Such further pharmaceutically active compounds can be those known to reduce appetite and are preferably selected from the group comprising PYY3-45, CCK, Leptin, and Insulin. Alternatively, or additionally, such further pharmaceutically active agent is a further nucleic acid according to the present invention. Alternatively, the medicament comprises at least one more nucleic acid which binds to a target molecule different from ghrelin or exhibits a function which is different from the one of the nucleic acids according to the present invention. In an embodiment, such nucleic acid is binding to a ghrelin lacking the octanoyl acid moiety.

Disease and/or disorders and/or diseased conditions for the treatment and/or prevention of which such medicament may be used include, but are not limited to obesity, the regulation of energy balance, appetite and body weight, eating disorders, gastrointestinal diseases, diabetes, glucose metabolism, tumour, blood pressure, cardiovascular diseases, acromegaly and other GH imbalances. As will be acknowledged by the ones of the art the inventive nucleic acids may factually be used in any disease where an antagonist to ghrelin can be administered to a patient in need of such antagonist and such antagonist is suitable to eliminate the cause of the disease or the disorder or at least to reduce the effects from the disease or the disorder. Such effect includes, but is not limited to obesity, the regulation of energy balance, appetite and body weight, eating disorders, gastrointestinal diseases, diabetes, glucose metabolism, tumour treatment, blood pressure, cardiovascular diseases, acromegaly and other GH imbalances. The applicability of the nucleic acids according to the present invention in connection with these and other diseases or disorders results, among others, from the involvement of ghrelin as outlined in the introductory part of the present specification. For the purpose of the present invention regulation of energy balance is regarded as a disease. More particularly, the use is for the treatment of any disease where the regulation of the energy balance is influenced by ghrelin, either directly or indirectly, and whereby reduction of the bioavailability of ghrelin is desired. The same applies to sugar metabolism, blood pressure and appetite and body weight. Further disease which may be treated using the nucleic acids according to the present invention, possibly upon systemic or local application are those which can be selected from the group comprising pituitary tumors, acromegaly, central Cushing's syndrome, adrenal Cushing's syndrome, paraneoplastic Cushing's syndrome, ectopic Cushing's syndrome, adrenal tumor, stress, hypercortisolism, cardiac insufficiency, cardiay infarction, stroke, adrenocortical insufficiency, hypotonia, aortic stenosis, pulmonal hypertonia, constrictive pericarditis, infectious diseases, infectious toxic hypotonia, hypovolemia, and hypronatriemia.

As used herein, the term gastrointestinal disease which can be treated using the nucleic acids according to the present invention, comprises stomach diseases and disorders, bowel diseases and disorders, colon disorders and diseases and modulation of gastric and colonic motility. In a preferred embodiment, the term bowel disorders and bowel diseases comprises inflammatory bowel diseases. More preferred inflammatory bowel diseases are ulcerative colitits and Crohn's disease. The suitability of the nucleic acids according to the present invention for the treatment of this kind of diseases arises from the involvement of ghrelin in such diseases as described in Karmiris K et al. (Karmiris K, Koutroubakis I E, Xidakis C, Polychronaki M, Voudouri T, Kouroumalis E A. Circulating levels of leptin, adiponectin, resistin, and ghrelin in inflammatory bowel disease. Inflamm Bowel Dis. February 2006;12(2):100-5), Tebbe J J et al. (Tebbe J J, Mronga S, Tebbe C G, Ortmann E, Arnold R, Schafer M K. Ghrelin-induced stimulation of colonic propulsion is dependent on hypothalamic neuropeptide Y1- and corticotrophin-releasing factor 1 receptor activation. J Neuroendocrinol. September 2005; 17(9):570-6) and Fukuda H. et al. (Fukuda H, Mizuta Y, Isomoto H, Takeshima F, Ohnita K, Ohba K, Omagari K, Taniyama K, Kohno S. Ghrelin enhances gastric motility through direct stimulation of intrinsic neural pathways and capsaicin-sensitive afferent neurones in rats. Scand J Gastroenterol. December 2004;39(12):1209-14).

The publication of Kobelt et al. (Kobelt P, Helmling S, Stengel A, Wlotzka B, Andresen V, Klapp B F, Wiedenmann B, Klussmann S, Monnikes H. Anti-ghrelin SPIEGELMER NOX-B11 inhibits neurostimulatory and orexigenic effects of peripheral ghrelin in rats. Gut. Jun. 30, 2005 Epub ahead of print) reports a dose-dependant reduction on short-term food intake induced by peripheral ghrelin upon administration of anti-ghrelin Spiegelmer NOX-B11. More specifically, in the positive control group treatment with PBS and 3 nmol ghrelin (vehicle/ghrelin group) significantly increased food intake within the first half hour following intraperitoneal injection (4.94±0.63 g/kg-BW) compared to the vehicle/vehicle group (1.13±0.59 g/kg-BW, $p<0.0002$) (FIG. 2A of Kobelt et al., supra). Pretreatment with 30 nmol of Spiegelmer NOX-B11 (=SOT-C=B11trc) blocked the stimulatory effect of ghrelin on food intake (0.58±0.58 g/kg-BW, $p<0.0001$) (FIG. 2A of Kobelt et al., supra). In contrast, administration of a control Spiegelmer consisting of a random sequence had no such inhibitory effect, leaving the ghrelin-induced stimulation on food intake intact (4.77±0.66 g/kg-BW; $p>0.864$) (FIG. 2A of Kobelt et al., supra).

The inhibitory effect of NOX-B11 (=SOT-C=B11trc) on food intake proved to be strictly dose-dependent. A dose of 1 nmol of Spiegelmer NOX-B11 (=SOT-C=B11trc) had no effect on ghrelin's stimulation of food intake (FIG. 2A of Kobelt et al., supra). An intermediate effect was observed for a dose of 10 nmol of NOX-B11(=SOT-C=B11trc): At this dose level the stimulatory effect of 3 nmol ghrelin during the first 30 minutes was moderated (3.51±0.66 g/kg-BW vs. 4.94±0.63 g/kg-BW $p>0.159$ vs ghrelin alone) (FIG. 2A of Kobelt et al., supra).

The publication of Shearman et al. (Shearman L P, Wang S P, Helmling S, Stribling D S, Mazur P, Ge L, Wang L, Klussmann S, Macintyre D E, Howard A D, Strack A M. Ghrelin Neutralisation by a Ribonucleic Acid-SPM Ameliorates Obesity in Diet-Induced Obese Mic.; Endocrinology. March 2006;147(3):1517-26. Epub Dec. 8, 2005) reports a reduction in body weight and decrease in food intake upon administration of anti-ghrelin Spiegelmer NOX-B11-2 (SOT-D-109) in Diet-induced Obese (DIO) mice. More specifically, NOX-B11-2 (SOT-D-109) infusion evoked weight loss compared to controls (see FIG. 4A of Shearman et al., supra). Significant body weight loss was observed with NOX-B11-2 (SOT-D-109) infusion on days 1 through 10 and on day 12 compared to vehicle treated mice; on days 1 through 13 compared to the control Spiegelmer (control SPM) infused group ($P<0.05$ vs. vehicle or Control SPM). By day 13, NOX-B11-2 infused mice gained an average of 0.32 g of body weight while those receiving control Spiegelmer gained an average of 1.85 g, and those receiving vehicle gained an average of 0.91 g. Also, NOX-B11-2 (SOT-D-109) infusion decreased food intake significantly (see FIG. 4B of Shearman et al., supra). Significant effects on cumulative food intake were observed on days 1-8 as compared to the vehicle group and on days 1-13 as compared to the control Spiegelmer group (39.33 g vs. 42.61 g on day 13; $p<0.05$) (FIG. 4C of Shearman et al., supra). Additionally, feed efficiency (weight gain per kcal ingested) which indicates how efficiently the food energy was used for accretion of body mass, was calculated from days 1-5 and 6-13 (see FIG. 4D of Shearman et al., supra). Feed efficiency was reduced by NOX-B11-2 (SOT-D-109) infusion on days 1-5 and this effect was not observed from days 6-13, suggesting that the transient reduction in weight gain was not simply due to reduction in food intake. Additionally, treatment with NOX-B11-2 (SOT-D-109) altered body composition of DIO mice (FIG. 4E of Shearman et al., supra). In contrast to no change in lean mass content, fat mass content of NOX-B11-2 (SOT-D-109) infused mice was decreased, even after correction for total body weight (FIG. 4F of Shearman et al., supra). White adipose tissue depot weights were not altered by NOX-B11-2 (SOT-D-109) infusion and control Spiegelmer infusion did not alter body composition or white adipose tissue weights.

In chronic infusion studies with NOX-B11-2 (SOT-D-109) using both DIO ghrelin-deficient and wild-type mice, a significant body weight loss was observed upon NOX-B11-2 (SOT-D-109) infusion in wild-type mice on days 1 to 6 (see FIG. 5A of Shearman et al., supra). In contrast thereto, NOX-B11-2 (SOT-D-109) did not alter body weight in Ghrl −/− mice (See FIG. 5B of Shearman et al., supra). Additionally, NOX-B11-2 (SOT-D-109) infusion reduced daily food intake on day 1 in wild-type mice (see FIG. 5C of Shearman et al., supra). NOX-B11-2 (SOT-D-109) infusion did not alter food intake of Ghrl−/− mice (see FIG. 5D of Shearman et al., supra).

It is within the present invention that the medicament is alternatively or additionally used, in principle, for the prevention of any of the diseases disclosed in connection with the use of the medicament for the treatment of said diseases. Respective markers therefor are selected from the group comprising cardiovascular risk factors, such as for example cholesterol and low aerobic activity and general factors that necessitate weight management.

The medicament according to the present invention can be administered, in principle, in any form known to the ones skilled in the art. A preferred route of administration is systemic administration, more preferably by injection. Alternatively, the medicament may be administered locally. Other routes of administration comprise intramuscular, intraperitoneal, and subcutaneous, per orum, or intranasal with preference given to the route of administration that is the least invasive, while ensuring efficacy.

In a further aspect the present invention is related to a pharmaceutical composition. Such pharmaceutical composition comprises at least one of the nucleic acids according to the present invention and preferably a pharmaceutically acceptable binder. Such binder can be any binder used and/or known in the art. More particularly such binder is any binder as discussed in connection with the manufacture of the medicament disclosed herein. In a further embodiment, the pharmaceutical composition comprises a further pharmaceutically active agent.

It is within the present invention that the medicament as described herein constitutes the pharmaceutical composition disclosed herein.

In a further aspect the present invention is related to a method for the treatment of a subject who is need of such treatment, whereby the method comprises the administration of a pharmaceutically active amount of at least one of the nucleic acids according to the present invention. In an embodiment, the subject suffers from a disease or is in risk to develop such disease, whereby the disease is any of those disclosed herein, particularly any of those diseases disclosed in connection with the use of any of the nucleic acids according to the present invention for the manufacture of a medicament.

It is to be understood that the nucleic acid as well as the antagonists according to the present invention can be used not only as a medicament or for the manufacture of a medicament, but also for cosmetic purposes, particularly with regard to the involvement of ghrelin in obesity. For the same purpose and/or for the same reasons the nucleic acid as well as the antagonists according to the present invention can be used as a food additive, a means for weight control, a means for appetite control and/or as diagnostic. A composition comprising the nucleic acid as well as the antagonists according to the present invention can be used for any of the aforementioned purposes.

As preferably used herein a diagnostic or diagostic agent or diagnostic means is suitable to detect, either directly or indirectly ghrelin, preferably ghrelin as described herein and more preferably ghrelin as described herein in connection with the various disorders and diseases described herein. The diagnostic is suitable for the detection and/or follow-up of any of the disorders and diseases, respectively, described herein. Such detection is possible through the binding of the nucleic acids according to the present invention to ghrelin. Such binding can be either directly or indirectly be detected. The respective methods and means are known to the ones skilled in the art. Among others, the nucleic acids according to the present invention may comprise a label which allows the detection of the nucleic acids according to the present invention, preferably the nucleic acid bound to ghrelin. Such a label is preferably selected from the group comprising radioactive, enzymatic and fluorescent labels. In principle, all known assays developed for antibodies can be adopted for the nucleic acids according to the present invention whereas the target-binding antibody is substituted to a target-binding nucleic acid. In antibody-assays using unlabeled target-binding antibodies the detection is preferably done by an secondary antibody which is modified with radioactive, enzymatic and fluorescent labels and bind to the target-binding antibody at its Fc-fragment. In the case of a nucleic acid, preferably a nucleic acid according to the present invention, the nucleic acid is modified with such a label, whereby preferably such a label is selected from the group comprising biotin, Cy-3 and Cy-5, and such label is detected by an antibody directed against such label, e.g. an anti-biotin antibody, an anti-Cy3 antibody or an anti-Cy5 antibody, or—in the case that the label is biotin—the label is detected by streptavidin or avidin which naturally bind to biotin. Such antibody, streptavidin or avidin in turn is preferably modified with a respective label, e.g. a radioactive, enzymatic or fluorescent label (like an secondary antibody).

In a further embodiment the nucleic acid molecules according to the invention are detected or analysed by a second detection means, wherein the said detection means is a molecular beacon. The methodology of molecular beacon is known to persons skilled in the art. In brief, nucleic acids probes which are also referred to as molecular beacons, are a reverse complement to the nucleic acids sample to be detected and hybridise because of this to a part of the nucleic acid sample to be detected. Upon binding to the nucleic acid sample the fluorophoric groups of the molecular beacon are separated which results in a change of the fluorescence signal, preferably a change in intensity. This change correlates with the amount of nucleic acids sample present.

The assays for discrimination of bioactive and non-bioactive ghrelin according to the present invention may be performed using standard techniques as known by persons skilled in the art. It is to be understood that such assays can also be used for the detection of ghrelin and preferably bioactive ghrelin as will be outlined in the following.

It will be acknowledged that the detection of ghrelin using the nucleic acids according to the present invention will particularly allow the detection of bioactive ghrelin as defined herein. Additionally, the bioactive ghrelin can be detected apart and thus be discriminated the des-octanoyl ghrelin by, among others, the following procedure, whereby other procedures will be obvious for the one skilled in the art.

In connection with the detection of the bioactive ghrelin a preferred method comprises the following steps:
 (a) providing a sample which is to be tested for the presence of bioactive ghrelin,
 (b) providing a nucleic acid according to the present invention,
 (c) reacting the sample with the nucleic acid, preferably in a reaction vessel
 whereby step (a) can be performed prior to step (b), or step (b) can be preformed prior to step (a).

In a preferred embodiment a further step d) is provided, which consists in the detection of the reaction of the sample with the nucleic acid. Preferably, the nucleic acid of step b) is immobilised to a surface. The surface may be the surface of a reaction vessel such as a reaction tube, a well of a plate, or the surface of a device contained in such reaction vessel such as, for example, a bead. The immobilisation of the nucleic acid to the surface can be made by any means known to the ones skilled in the art including, but not limited to, non-covalent or covalent linkages. Preferably, the linkage is established via a covalent chemical bond between the surface and the nucleic acid. However, it is also within the present invention that the nucleic acid is indirectly immobilised to a surface, whereby such indirect immobilisation involves the use of a further component or a pair of interaction partners. Such further component is preferably a compound which specifically interacts with the nucleic acid to be immobilised which is also referred to as interaction partner, and thus mediates the attachment of the nucleic acid to the surface. The interaction partner is preferably selected from the group comprising nucleic acids, polypeptides, proteins and antibodies. Preferably, the interaction partner is an antibody, more preferably a monoclonal antibody. Alternatively, the interaction partner is a nucleic acid, preferably a functional nucleic acid. More preferably such functional nucleic acid is selected from the group comprising aptamers, spiegelmers, and nucleic acids which are at least partially complementary to the nucleic acid. In a further alternative embodiment, the binding of the nucleic acid to the surface is mediated by a multi-partite interaction partner. Such multi-partite interaction partner is preferably a pair of interaction partners or an interaction partner consisting of a first member and a second member, whereby the first member is comprised by or attached to the nucleic acid and the second member is attached to or comprised by the surface. The multi-partite interaction partner is preferably selected from the group of pairs of interaction partners comprising biotin and avidin, biotin and streptavidin, and biotin and neutravidin. Preferably, the first member of the pair of interaction partners is biotin.

A preferred result of such method is the formation of an immobilised complex of bioactive ghrelin and the nucleic acid, whereby more preferably said complex is detected. It is within an embodiment that from the complex the bioactive ghrelin is detected. More preferably, the bioactive ghrelin is detected by a detection means which is specific for bioactive ghrelin. In a particularly preferred embodiment the bioactive ghrelin is detected by a detection means which detects both bioactive ghrelin and non-bioactive ghrelin.

A respective detection means which is in compliance with this requirement is, for example, any detection means which is specific for that/those part(s) of the ghrelin which is identical in both the bioactive ghrelin and the des-octanoyl ghrelin. Preferably, such detection means thus binds to the C-terminal end of the ghrelin, or at least is not binding to the domain formed by the N-terminus and the n-octanoyl side chain. A particularly preferred detection means is a detection means which is selected from the group comprising nucleic acids, polypeptides, proteins and antibodies, the generation of which is known to the ones skilled in the art.

The method for the detection of ghrelin also comprises that the sample is removed from the reaction vessel which has preferably been used to perform step c).

The method comprises in a further embodiment also the step of immobilising an interaction partner of bioactive and/or des-octanoyl ghrelin on a surface, preferably a surface as defined above, whereby the interaction partner is defined as herein and preferably as above in connection with the respective method and more preferably comprises nucleic acids, polypeptides, proteins and antibodies in their various embodiments. In this embodiment, a particularly preferred detection means is a nucleic acid according to the present invention, whereby such nucleic acid may preferably be labelled or non-labelled. In case such nucleic acid is labelled it can be directly or indirectly be detected. Such detection may also involve the use of a second detection means which is, preferably, also selected from the group comprising nucleic acids, polypeptides, proteins and embodiments in the various embodiments described herein. Such detection means are preferably specific for the nucleic acid according to the present invention. In a more preferred embodiment, the second detection means is a molecular beacon. Either the nucleic acid or the second detection means or both may comprise in a preferred embodiment a detection label. The detection label is preferably selected from the group comprising biotin, a bromo-desoxyuridine label, a digoxigenin label, a fluorescence label, a UV-label, a radio-label, and a chelator molecule. Alternatively, the second detection means interacts with the detection label which is preferably contained by, comprised by or attached to the nucleic acid. Particularly preferred combinations are as follows:

the detection label is biotin and the second detection means is an antibody directed against biotin, or wherein
the detection label is biotin and the second detection means is an avidin or an avidin carrrying molecule, or wherein
the detection label is biotin and the second detection means is a streptavidin or a stretavidin carrying molecule, or wherein
the detection label is biotin and the second detection means is a neutravidin or a neutravidin carrying molecule, or
wherein the detection label is a bromo-desoxyuridine and the second detection means is an antibody directed against bromo-desoxyuridine, or wherein
the detection label is a digoxigenin and the second detection means is an antibody directed against digoxigenin, or
wherein the detection label is a chelator and the second detection means is a radio-nuclide, whereby it is preferred that said detection label is attached to the nucleic acid. It is to be acknowledged that this kind of combination is also applicable to the embodiment where the nucleic acid is attached to the surface. In such embodiment it is preferred that the detection label is attached to the interaction partner.

Finally, it is also within the present invention that the second detection means is detected using a third detection means, preferably the third detection means is an enzyme, more preferably showing an enzymatic reaction upon detection of the second detection means, or the third detection means is a means for detecting radiation, more preferably radiation emitted by a radio-nuclide. Preferably, the third detection means is specifically detecting and/or interacting with the second detection means.

Also in the embodiment with an interaction partner of bioactive and/or des-octanoyl ghrelin being immobilised on a surface and the nucleic acid according to the present invention is preferably added to the complex formed between the interaction partner and the ghrelin, the sample can be removed from the reaction, more preferably from the reaction vessel where step c) and/or d) are preformed.

In an embodiment the nucleic acid according to the present invention comprises a fluorescence moiety and whereby the fluorescence of the fluorescence moiety is different upon complex formation between the nucleic acid and bioactive ghrelin and free bioactive ghrelin.

In a further embodiment the nucleic acid is a derivative of the nucleic acid according to the present invention, whereby the derivative of the nucleic acid comprises at least one fluorescent derivative of adenosine replacing adenosine. In a preferred embodiment the fluorescent derivative of adenosine is ethenoadenosine.

In a further embodiment the complex consisting of the derivative of the nucleic acid according to the present invention and the bioactive ghrelin is detected using fluorescence.

In an embodiment of the method a signal is created in step (c) or step (d) and preferably the signal is correlated with the concentration of bioreactive ghrelin in the sample.

In a preferred aspect, the assays may be performed in 96-well plates, where components are immobilized in the reaction vessels as described above and the wells acting as reaction vessels.

The above sequence of reaction steps and the various embodiments described in connection therewith are, in principle, suitable to detect both bioactive ghrelin, i.e. octanoyl ghrelin and more preferably n-octanoyl ghrelin, and des-octanoyl ghrelin. This is possible under the proviso that for the detection of bioactive ghrelin, at least one of the interaction partners and the nucleic acid according to the present invention is suitable to specifically detect the bioactive ghrelin. In principle, it is sufficient that the nucleic acid according to the present invention which is specific for bioactive ghrelin, is used. The readout of this kind of method specifying the amount of ghrelin contained in a sample can as such be used as the result of an analysis for bioactive ghrelin. However, the result may also be used in a method for determining the overall content of ghrelin, preferably both bioactive ghrelin and des-octanoyl ghrelin. For such purpose, a method preferably identical to the above is performed which uses either detection means or interaction partners specific for des-octanoyl ghrelin or suitable to detect both bioactive and des-octanoyl ghrelin, i. e. the overall ghrelin content or the amount thereof. If said interaction partner or means is suitable to detect any ghrelin, regardless whether it is bioactive ghrelin or des-octanoyl ghrelin, the overall amount of ghrelin contained in the sample can be calculated by the readout of such method allowing to determine the percentage of bioactive ghrelin in the sample by quotient formation of the value obtained for bioactive ghrelin and the overall ghrelin content. In a further embodiment, the method is used to specifically detect des-octanoyl ghrelin. Such des-octanoyl ghrelin can, for example, be detected by detection means or interaction partners which are specific for the des-octanoyl ghrelin, such as by being directed to the C-terminus or the N-terminus of ghrelin lacking the n-octanoyl moiety. The amount of ghrelin thus determined, i. e. the amount of des-octanoyl ghrelin can then be added to the amount of bioactive ghrelin giving the overall content of ghrelin in the sample.

The inventive nucleic acid may further be used as starting material for drug design. Basically there are two possible approaches. One approach is the screening of compound libraries whereas such compound libraries are preferably low molecular weight compound libraries. In an embodiment, the screening is a high throughput screening. Preferably, high throughput screening is the fast, efficient, trial-and-error evaluation of compounds in a target based assay. In best case the analysis are carried by a colormatic measurement. Libraries as used in connection therewith are known to the one skilled in the art.

Alternatively, the nucleic acid according to the present invention may be used for rational design of drugs. Preferably, rational drug design is the design of a pharmaceutical lead structure. Starting from the 3-dimensional structure of the target which is typically identified by methods such as X-ray crystallography or nuclear magnetic resonance spectroscopy, computer programs are used to search through databases containing structures of many different chemical compounds. The selection is done by a computer, the identified compounds can subsequently be tested in the laboratory.

The rational design of drugs may start from any of the nucleic acid according to the present invention and involves a structure, preferably a three dimensional structure, which is similar to the structure of the inventive nucleic acids or identical to the binding mediating parts of the structure of the inventive nucleic acids. In any case such structure still shows the same or a similar binding characteristic as the inventive nucleic acids. In either a further step or as an alternative step in the rational design of drugs the preferably three dimensional structure of those parts of the nucleic acids binding to the neurotransmitter are mimicked by chemical groups which are different from nucleotides and nucleic acids. By this mimicry a compound different from the nucleic acids can be designed. Such compound is preferably a small molecule or a peptide.

In case of screening of compound libraries, such as by using a competitive assay which are known to the one skilled in the arts, appropriate ghrelin analogues, ghrelin agonists or ghrelin antagonists may be found. Such competitive assays may be set up as follows. The inventive nucleic acid, preferably a spiegelmer which is a target binding L-nucleic acid, is coupled to a solid phase. In order to identify ghrelin analogues labelled ghrelin may be added to the assay. A potential analogue would compete with the ghrelin molecules binding to the spiegelmer which would go along with a decrease in the signal obtained by the respective label.

Screening for agonists or antagonists may involve the use of a cell culture assay as known to the ones skilled in the art.

The kit according to the present invention may comprise at least one or several of the inventive nucleic acids. Additionally, the kit may comprise at least one or several positive or negative controls. A positive control may, for example, be ghrelin, particularly the one against which the inventive nucleic acid is selected or to which it binds, preferably, in liquid form. A negative control may, e.g., be a peptide which is defined in terms of biophysical properties similar to ghrelin, but which is not recognized by the inventive nucleic acids. Furthermore, said kit may comprise one or several buffers. The various ingredients may be contained in the kit in dried or lyophilised form or solved in a liquid. The kit may comprise one or several containers which in turn may contain one or several ingredients of the kit. In a further embodiment, the kit comprises an instruction or instruction leaflet which provides to the user information on how to use the kit and its various ingredients.

As preferably used herein, the term treatment comprises in a preferred embodiment additionally or alternatively prevention and/or follow-up.

As preferably used herein, the terms disease and disorder shall be used in an interchangeable manner, if not indicated to the contrary.

As used herein, the term comprise is preferably not intended to limit the subject matter followed or described by such term. However, in an alternative embodiment the term comprises shall be understood in the meaning of containing and thus as limiting the subject matter followed or described by such term.

The various SEQ. ID. Nos., the chemical nature of the nucleic aicd molecules according to the present invention and the target molecules ghrelin as used herein, the actual sequence thereof and the internal reference number is summarized in the following table.

TABLE 1

| Seq.-ID | RNA/Peptide | Sequence | Internal Reference |
|---|---|---|---|
| 1 | L-peptide | GSSFLSPEHQRVQQRKESKKPPAKLQPR | human ghrelin |
| 2 | L-peptide | GSSFLSPEHQKAQQRKESKKPPAKLQPR | rat ghrelin |
| 3 | L-RNA | UAAX$_1$X$_2$CCGAAX$_3$GUAX$_4$CCAUUCCUX$_5$C | whereby X$_1$ = G or A; X$_2$ = A or U; X$_3$ = G or A; X$_4$ = A or C or U; and X$_5$ = G or A |
| 4 | L-RNA | UAAGACCGAAGGUACCCAAUCCUAC | preferable sequence of Seq. ID 3 |
| 5 | L-RNA | GGGUAAGCGUAAGACCGAAAGUAACCAAUCCUACCGUAUAUACGGUGAGGCAGCAC | MS-P2-E3 |
| 6 | L-RNA | GGCUAAGCGUAAGACCGAACGUAACCAAUCCUACCGUAUCUACAGUGACGCAGCAC | MS-P2-G2 |
| 7 | L-RNA | GGGUAACCGUAAGACCGAAGGUAACCAAUCCUACCGUAUCUACGGUGAGGCAGCAC | MS-P2-D2 |
| 8 | L-RNA | GGGUAAGCGUAAGACCGAAGGUAACCAAUCCUAUCGUAUCUAUGGUGAGGCAGCAC | MS-P2-A3 |
| 9 | L-RNA | GGGUAUGCAUAAGACCGAAGGUAACCAAUCCUACCGUAUCUACGGUGAGGCAGCAC | MS-P2-E1 |
| 10 | L-RNA | GGGUAUGCGUAAGACCGAAGGUAACCAAUCCUACCGUAUCUACGGUGAGGCAGCAC | MS-P2-B1 |
| 11 | L-RNA | GGGUGAGCGUAAGACCGAAGGUAACCAAUCCUACCGUAUCUACGGUGAGGCAGCAC | MS-P2-F1 |
| 12 | L-RNA | GGGUGUAUGUAAGACCGAAGGUAACCAAUCCUACCAUAUCUACGGUGAGGCAGCAC | MS-P2-C3 |
| 13 | L-RNA | CGGUGUGCGUAAGACCGAACGUAACCAAUCCUACCAUAUCUACGGUGAGGCAGCAC | MS-P2-C2 |
| 14 | L-RNA | GGGUGUGCGUAAGACCGAAGGUAACCAAUCCUACCGUAUCAUAUCUACGGUGAGGCAGCAC | MS-P2-H2 |
| 15 | L-RNA | GGGUGUGCGUAAGACCGAAGGUACCCAAUCCUACCUACUAACUGGUGAGGCAGCAC | MS-P2-A4 |
| 16 | L-RNA | GGGUGACGUAAGACCGAAGUACCCAAUCCUACCUUUCCUGAGGUGAGGCAGCAC | MS-P2-B2 |
| 17 | L-RNA | GGGUGCUGUGAGGCAAAAAAGUAAGUCCGAAGGUAACCAAUCCUACAGCAC | MS-P2-A2 |
| 18 | L-RNA | GGGUGCUGUGAGGGAAUGCGUAAGUCCGAAGGUAUCCAAUCCUGCAGCAC | MS-P3-H3 |
| 19 | L-RNA | GGGUGUUGUGAGGCAAUAAGUAAGUCCGAAGGUAACCAAUCCUGCAGCAC | MS-P2-D1 |
| 20 | L-RNA | CGUGUGAGGCAAUAAAACUUAAGUCCGAAGGUAACCAAUCCUACACG | SOT-C (B11trc = NOX-B11) |
| 21 | L-RNA | CGUGUGAGGUAGUAAAAAAAAAAAACGUAAAUCCGAAGGUAACCAAUCCUACACG | F12 |
| 22 | L-RNA | CGUGCGGUGAGGCAAAAACGUAAGACCGAAGGUAACCAUUCCUACCCACG | SOT-D (C12) |
| 23 | L-RNA | CGUGCGGUGAGGCAGACGUAAGACCGAAGGUAACCAUUCCUACCCACC | SOT-D-000 |
| 24 | L-RNA | CGGUGAGGCAGACGUAAGACCGAAGGUAACCAUUCCUACCG | SOT-D-100 |
| 25 | L-RNA | CGGUGAGGCAGAUAAGACCGAAGGUAACCAUUCCUACCG | SOT-D-101 |
| 26 | L-RNA | CGGUGAGGCAAUAAGACCGAAGGUAACCAUUCCUACCG | SOT-D-102 |
| 27 | L-RNA | GGUGAGGCAGACGUAAGACCGAAGGUAACCAUUCCUACC | SOT-D-104 |
| 28 | L-RNA | GGUAGGCAGACGUAAGACCGAAGGUAACCAUUCCUACC | SOT-D-106 |
| 29 | L-RNA | CCGGUGAGGCAGACGUAAGACCGAAGGUAACCAUUCCUACCGG | SOT-D-108 |

TABLE 1-continued

| Seq.-ID | RNA/Peptide | Sequence | Internal Reference |
|---|---|---|---|
| 30 | L-RNA | CCGGUGAGGCAGUAAGAC-CGAA GGUAACCAUUCCUACCGG | SOT-D-109 (NOX-B11-2) |
| 31 | L-RNA | CCGGUGAGGCAGUAAGAC-CGAA GGUAACCAUUCCUACCGG | SOT-D-110 |
| 32 | L-RNA | CCGGUGAGGCCGUAAGAC-CGAA GGUAACCAUUCCUACCGG | SOT-D-111 |
| 33 | L-RNA | GGGUGAGCGUAAGAC-CGAAGGU AACCAAUCCUACCGUAUC-UACG GUGAGGCAGCAC | SOT-E or MS-P2-F1 |
| 73 and 80 | L-RNA | GGGUGAGCGUAAGAC-CGAAGGU AACCAAUCCUACC---S----G GUGAGGCAGCAC | SOT-E-02 |
| 35 | L-RNA | CGUAAGACCGAAGGUAAC-CAAU CCUACCGUAUCUACG-GUGAGGC AGCAC | SOT-E-09 |
| 74 and 81 | L-RNA | GGGUGAGCGUAAGAC-CGAAGGU AACCAAUCCUACCG--S---CG GUGAGGCAGCAC | SOT-E-11 |
| 37 | L-RNA | GGGUGAGCGUAAGAC-CGAAGGU AACCAAUCCUACCGUAUC-UAGG GUGAGGCAGC | SOT-E-12 |
| 38 | L-RNA | GCGUAAGACCGAAGGUAAC-CAA UCCUACCGUAUCUACG-GUGAGG CAGCAC | SOT-E-14 |
| 75 and 82 | L-RNA | GCGUAAGACCGAAGGUAAC-CAA UCCUACCG--S----CG-GUGAGG CAGCAC | SOT-E-19 |
| 76 and 83 | L-RNA | CGGUGAGGCAGCAC---S-GCG UAAGACCGAAGGUAAC-CAAUCC UACCG | SOT-E-21 |
| 77 and 84 | L-RNA | CGGUGAGGCAGC---S-GCGUA AGACCGAAGGUAACCAAUC-CUA CCG | SOT-E-25 |
| 78 and 85 | L-RNA | GCGUAAGACCGAAGGUAAC-CAA UCCUACCG--S---CG-GUGAGG CAGC | SOT-E-33 |
| 43 | L-RNA | GCGUAAGACCGAAGGUAAC-CAA UCCUACCGUAUCUACG-GUGAGG CAGCAC | SOT-E-19-L |
| 44 | L-RNA | GCGUAAGACCGAAGGUAAC-CAA UCCUACCGAAACGGUGAG-GCAG CAC | SOT-E-19-L1 |
| 45 | L-RNA | GCGUAAGACCGAAGGUAAC-CAA UCCUACCGAUACGGUGAG-GCAG CAC | SOT-E-19-L2 |
| 46 | L-RNA | GCGUAAGACCGAAGGUAAC-CAA UCCUACCGACACGGUGAG-GCAG CAC | SOT-E-19-L3 |
| 47 | L-RNA | GCGUAAGACCGAAGGUAAC-CAA UCCUACCGCAACGGUGAG-GCAG CAC | SOT-E-19-L4 |
| 48 | L-RNA | GCGUAAGACCGAAGGUAAC-CAA UCCUACCGAUCUCGGUGAG-GCA GCAC | SOT-E-19-L5 |
| 49 | L-RNA | GCGUAAGACCGAAGGUAAC-CAA UCCUACCGUUUCGGUGAG-GCAG CAC | SOT-E-19-L6 |
| 50 | L-RNA | GCGUAAGACCGAAGGUAAC-CAA UCCUACCGUAUCGGUGAG-GCAG CAC | SOT-E-19-L7 |
| 79 and 86 | L-RNA | 5'-PEG-GCGUAAGAC-CGAAGG UAACCAAUCCUACCG--S---C GGUGAGGCAGCAC | SOT-E-19-5'-PEG |
| 52 | L-RNA | 5'-PEG-CCGGUGAG-GCAGUAA GACCGAAGGUAACCAUUC-CUAC CGG | SOT-D-109 (NOX-B11-2) |
| 53 | D-peptide | GSSFLSPE-HQRVQQRKESKKPP AKLQPR | biotin. human D-ghrelin |
| 54 | D-RNA | GGGUAAGCGUAAGAC-CGAAAGU AACCAAUCCUAC-CGUAUAUACG GUGAGGCAGCAC | MS-P2-E3 |
| 55 | D-RNA | GGGUAAGCGUAAGAC-CGAAGGU AACCAAUCCUACCGUAUC-UACA GUGAGGCAGCAC | MS-P2-G2 |
| 56 | D-RNA | GGGUAACCGUAAGAC-CGAAGGU AACCAAUCCUACCGUAUC-UACG GUGAGGCAGCAC | MS-P2-D2 |

TABLE 1 -continued

| Seq.-ID | RNA/Peptide | Sequence | Internal Reference |
|---|---|---|---|
| 57 | D-RNA | GGGUAAGCGUAAGAC-CGAAGGU AACCAAUCCUAUCGUAUC-UAUG GUGAGGCAGCAC | MS-P2-A3 |
| 58 | D-RNA | GGGUAUGCAUAAGAC-CGAAGGU AACCAAUCCUACCGUAUC-UACG GUGAGGCAGCAC | MS-P2-E1 |
| 59 | D-RNA | GGGUAUGCGUAAGAC-CGAAGGU AACCAAUCCUACCGUAUC-UACG GUGAGGCAGCAC | MS-P2-B1 |
| 60 | D-RNA | GGGUGAGCGUAAGAC-CGAAGGU AACCAAUCCUACCGUAUC-UACG GUGAGGCAGCAC | MS-P2-F1 |
| 61 | D-RNA | GGGUGUAUGUAAGAC-CGAAGGU AACCAAUCCUACCAUAUC-UACG GUGAGGCAGCAC | MS-P2-C3 |
| 62 | D-RNA | GGGUGUGCGUAAGAC-CGAAGGU AACCAAUCCUACCAUAUC-UACG GUGAGGCAGCAC | MS-P2-C2 |
| 63 | D-RNA | GGGUGUGCGUAAGAC-CGAAGGU AACCAAUCCUAUCAUAUC-UACG GUGAGGCAGCAC | MS-P2-H2 |
| 64 | D-RNA | GGGUGUGCGUAAGAC-CGAAGGU ACCCAAUCCUACCUAC-UAACUG GUGAGGCAGCAC | MS-P2-A4 |
| 65 | D-RNA | GGGUGACGUAAGACCGAAG-GUA CCCAAUCCUACCUUUC-CUGAGG UGAGGCAGCAC | MS-P2-B2 |
| 66 | D-RNA | GGGUGCUGUGAG-GCAAAAAAGU AAGUCCGAAGGUAAC-CAAUCCU ACAGCAC | MS-P2-A2 |
| 67 | D-RNA | GGGUGCUGUGAG-GCAAUGCGUA AGUCCGAAGGUAUCCAAUC-CUG CAGCAC | MS-P3-H3 |
| 68 | D-RNA | CGUGUGAGGCAAUAAAACU-UAA GUCCGAAGGUAACCAAUC-CUAC ACG | SOT-C (B11trc = NOX-B11) |
| 69 | D-RNA | CCGGUGAGGCAGUAAGAC-CGAA GGUAACCAUUCCUACCGG | SOT-D-109 (NOX-B11-2) |
| 70 | D-RNA | GGGUGAGCGUAAGAC-CGAAGGU AACCAAUCCUACCGUAUC-UACG GUGAGGCAGCAC | SOT-E or MS-P2-F1 |
| 71 | L-RNA | 5'-PEG-UAAGGAAACUCG-GUC UGAUGCGGUAGCGCUGUG-CAGA GCU | Control Spiegelmer |
| 72 | L-RNA | 5'-biotin-CGUGUGAG-GCAA UAAAACUUAAGUCCGAAG-GUAA CCAAUCCUACACG | biotinylated NOX-B11 |

EXAMPLE 1

Ghrelin Binding Sequences

If not explicitly indicated to the contrary, the ghrelin used throughout these examples was ghrelin in its octanoylated form.

Using a technology derived from the one described in DE 10349441.3 an RNA in vitro selection directed to biotinylated human D-ghrelin was carried out. An enriched population of dsDNA molecules was cloned and sequenced. The result of the sequence analysis can be seen in FIG. 1.

All sequences comprise the Ghrelin-binding motif A (25 nucleotides) of the known Ghrelin-binding sequence SOT-C (B11trc; see patent application WO2004/013274 A2). Only in four out of these 23 clones motiv A is rather located at the 3'-end of the sequence. Within 19 sequences motif A is located at the 5'-end of the clones. Additionally motif called motiv D is located at the 3'-end of motif A.

Binding Characteristics of the Sequences

The 15 clones (FIG. 1) showing variations at different positions were chosen for ranking experiments at 37° C. using the "competition assay" described in Example 2. As reference, the radiolabelled aptamer SOT-C (B11trc) was used. Several candidates were binding stronger to D-ghrelin than SOT-C (B11trc), showing either a lower $K_D$ or a higher amount of the active conformation which can not be differentiated within the "competition assay". The clones MS—P2-G2, MS—P2-D2, MS—P2-A2, MS—P2-H3 seemed to have a better binding than the control clone SOT-C (B11trc), the clones MS—P2-E1, MS—P2-B1, MS—P2-F1, MS—P2-C3, MS—P2-C2, MS—P2-A4 and MS—P2-B2 showed much better binding. Similar binding results in comparison to SOT-C (B11trc) could be determined for the clones MS—P2-E3, MS—P2-A3, MS—P2-H2, and MS—P2-D1 (FIG. 2; the evaluation see FIG. 1). Therefore the best clones were tested for their activity as aptamers in the equilibrium assay and as Spiegelmers in a cell culture assay at 37° C. (protocols see Example 2). The results are summarized in FIG. 1. The clones MS—P2-D2, MS—P2-F1, MS—P2-C2, MS—P2-A4 and MS—P2-B2 were measured at 37° C. in the equilibrium assay with an $K_D$ of 22-34 nM (appr. 60% active molecules) and $IC_{50}$ values of 3.0-8.0 nM could be detected in cell culture experiments at 37° C. In comparison, the $IC_{50}$ of SOT-C (B11trc) was detected with 20 nM at 37° C. and the $K_D$ was determined with 100 nM (47% active molecules) at 37° C.

(As described in patent application WO2004/013274 A2 the $IC_{50}$ of SOT-C at room temperature is approximatly 5 nM). The results indicates, that the biological activity of the Spiegelmers MS—P2-F1, MS—P2-C2 and MS—P2-D2 may even approximately five-fold be better than SOT-C (B11trc) at 37° C. For continuative truncation experiments clone MS—P2-F1 ($IC_{50}$ of 4.0 nM) was chosen (secondary structure prediction, see FIG. 12).

It is to be understood that any of the sequences shown in FIG. 1. are nucleic acids according to the present invention, including those truncated forms thereof which, however, are still capable of binding to the target.

EXAMPLE 2

Binding Characterization of the Sequences 2.1 Ranking of Radiolabeled Aptamers by Using the "Equilibrium Binding Assay"

Most of the clones that are disclosed herein and that are more particularly listed in FIG. 1 were ranked as radiolabeled aptamers (D-RNA) in respect of their binding behaviour towards biotinylated human D-ghrelin by using the "equilibrium binding assay".

A ranking of the binding behaviour of the molecules towards human D-ghrelin was done. For this purpose, using standard protocols as described herein the identified aptamers were synthesized as truncated aptamers (without primer binding sites) as depicted in FIG. 1.

In the following the aptamer sequences were radiolabeled at the 5'-end with $\gamma$-$P^{32}$-ATP using the following protocol.

| Component | [final] |
|---|---|
| Oligonucleotide | 5 μM |
| T4 Forward Reaction Buffer (Invitrogen) | 1x |
| T4 Polynucleotide Kinase (Invitrogen) | 10 U/10 μl$_{reaction\ volume}$ |
| [$\gamma$-$^{32}$P]-ATP | 1 μl/10 μl$_{reaction\ volume}$ |

The reaction was incubated for 1 h at 37° C. In the following the radiolabelled aptamers were gel-purified. 2-5 pmoles of the radiolabeled RNAs were denatured for 3 minutes at 95° C. in selection buffer (according to physiological conditions in human blood: 20 mM Tris, 150 mM NaCl, 5 mM KCl, pH 7.4 was adjusted at 37° C.) without $Ca^{++}$ and $Mg^{++}$, folded by addition of these ions to a final concentration of 1 mM at 37° C., and incubated for 1 hour at 37° C. with biotinylated human D-ghrelin in concentrations in the range of 0.4 to 3000 nM. Subsequently, a constant amount of NeutrAvidin agarose was added as matrix and the RNA:peptide complex was shaken at 37° C. for 30 more minutes. The matrix with bound peptide and tubes were then sedimented, the supernatant was removed, the matrix was washed with 100 μl selection buffer and the difference between bound and unbound RNA was determined by measuring the radioactivity by using a Beckman Coulter. From the calculated numbers, the control (0 nM biotinylated human D-ghrelin) was subtracted as background. The equilibrium constants were calculated by using the software program "GraFIT" (Version 4.0.10., Erithacus Software Ltd., Surrey, UK).

2.2 Ranking of Aptamers by Using Competition Assay

In order to compare the clones to the already known Ghrelin-binding sequence SOT-C (B11trc; see patent application WO2004/013274 A2), SOT-C was synthesized as aptamer (D-RNA) using standard protocols as described herein (Example 4). The aptamer sequence was radiolabelled at the 5'-end with $\gamma$-$P^{32}$-ATP using standard protocols as described herein.

Radiolabelled SOT-C and the identified clones (D-RNA) were prepared as described for the equilibrium assay. The assay was carried out at a peptide concentration (biotinylated human D-ghrelin) of 20 nM. Afterwards equimolar amounts of radiolabelled SOT-C and two different concentrations (40 nM and 200 nM) of the apatmers were tested (The results are depicted in FIG. 2). The assay was performed analogously to the equilibrium assay.

2.3 Inhibition of Ghrelin-induced Calcium Release by Ghrelin-binding Spiegelmers Functional characterization of ghrelin-binding Spiegelmers is performed in a cellular assay system monitoring the interaction of human (L-) ghrelin and the human growth hormone secretagogue receptor (GHS-R). The intracellular calcium release resulting from receptor-ligand interaction is visualized by means of a fluorescent calcium indicator.

Stable transfected CHO cells expressing the human ghrelin receptor (GHS-R1a) (obtained from Euroscreen, Gosselies, Belgium) are seeded with 5–7×$10^4$ cells per well in a black 96 well-plate with clear bottom (Greiner) and cultivated overnight at 37° C. and 5% $CO_2$ in UltraCHO medium (Cambrex) which contained in addition 100 units/ml penicillin, 100 μg/ml streptomycin, 400 μg/ml geneticin and 2.5 μg/ml fungizone.

Before loading with the calcium indicator dye fluo-4, cells are washed once with 200 μl CHO—U+. Then 50 μl of the indicator dye solution (10 μM fluo-4 (Molecular Probes), 0.08% pluronic 127 (Molecular Probes) in CHO—U+) are added and the cells are incubated for 60 min at 37° C. Thereafter cells are washed three times with 180 μl CHO—U+. Finally 90 μl CHO—U+ are added per well.

Variable amounts of Spiegelmers are incubated together with human (L-) ghrelin (purchased from Bachem) in Ultra-CHO medium, containing 5 mM probenecid and 20 mM HEPES (CHO—U+) for 15 to 60 min at room temperature or 37° C. in a 0.2 ml low profile 96-well plate. As a control, samples with peptide only (maximal calcium release) and samples without peptide (minimal calcium release) are analysed. In these stimulation solutions, the peptide and the Spiegelmer (if added) is 10-fold concentrated compared to the assay.

For detection of calcium release, the stimulation solution is added to the cells (10 μl/well), and the change of the fluorescence signal is monitored. Measurement of fluorescence signals is done at an excitation wavelength of 485 nm and an emission wavelength of 520 nm in a Fluostar Optima multidetection plate reader (BMG), equipped with injection pumps.

For parallel measurement of several samples, wells of one (perpendicular) row of a 96 well plate are recorded together. First three readings with a time lag of 4 sec are done for determination of the base line. Then the recording is interrupted and the plate is moved out of the instrument. Using a multi-channel pipette, 10 μl of the stimulation solution is added to the wells, then the plate is moved into the instrument again and the measurement is continued. In total 20 recordings with time intervals of 4 sec are performed.

For each well the difference between maximal fluorescence and base line value is determined and plotted against human (L-) ghrelin (octanoylated) concentration or, in the experiments on the inhibition of calcium release by Spiegelmers, against concentration of Spiegelmer allowing the determination of the half-maximal inhibition constant (IC50).

2.4 Surface Plasmon Resonance (SPR) Measurement

Aptamer characterisation binding to biotinylated human D-ghrelin were determined by SPR real time kinetic analysis using a BIAcore 2000 instrument (BIAcore AB, Uppsals Sweden) as described. 100RU (Flowcell 2) and 300RU (Flowcell 3) of the C-terminal biotinylated peptide were immobilized on a Streptavidin conjugated sensor chip (Biacore AB, Freiburg, Germany) and samples in a concentration range from 0.1 µM to 1 µM were injected using the Kinject command defining an association time of 360 (s) and a dissociation time of 360 (s). Flowcell 1 was used as buffer and dextran matrix control (Biacore SA-Chip surface) whereas on Flowcell 4 unspecific D-peptide was immobilized to determine unspecific binding of the aptamer. Reactions were at 37° C. For data analysis with the BIAevaluation 3.0 software (BIAcore AB, Uppsala, Sweden) we used the Langmuir 1:1 stochiometric fitting algorithm.

EXAMPLE 3

Definition of Ghrelin Binding Spiegelmer Motifs 3.1 Truncation of SOT-D-000
3.1.2 Terminal Truncation of Previously Selected Spiegelmer SOT-D-000

The ghrelin-binding Spiegelmers which are shown in FIG. 3 have been obtained previously, as already presented in patent application WO2004/013274 A2. In secondary structure predictions (minimum free energy conformations [Hofacker et al., 1994, Monatsh. Chem 125:167-188]), the possibility for canonical intramolecular base pairing between the 5'- and the 3'-terminus becomes obvious for all Spiegelmers (FIGS. 4-7; underlined bases in FIG. 3). The presence of such structural elements in a Spiegelmer may be vital for correct folding of the active three-dimensional structure, but for economical Spiegelmer synthesis, the molecules should be as short as possible. Spiegelmer SOT-D-000 (alias a truncated version of SOT-R04-DR14-F7 without primer binding sites) was chosen as basis for terminal truncation as it is the shortest selected Spiegelmer with the potential to form the longest terminal helix.

Truncated variants of SOT-D-000 with helical lengths of eight (SOT-D-108), seven (SOT-D-100), and six (SOT-D-104) base pairs instead of ten (FIG. 8) were synthesized and tested in cell culture as described in example 2 (FIG. 9). SOT-D-104 (39mer) significantly lost binding activity, whereas SOT-D-100 (41mer) and -108 (43mer) retained full ghrelin-antagonistic performance. Variant SOT-D-106, a further truncation of SOT-D-104 in which G4 had been removed, was virtually inactive. Surprisingly, this non-matched G—which is present in the helix of all selected ghrelin Spiegelmers—may not readily be removed. Rather, is appears to be essential for ghrelin binding.

3.1.2. Internal Deletion Mutants of SOT-D-100 and -108

When considering the alignment of selected ghrelin binders in FIG. 3, a highly variable region seems to exist in all aligned molecules directly adjacent to the terminal helix at the 5' end. In order to exploit this apparent variability for further truncation of ghrelin binders, the shortest fully active SOT-D variants SOT-D-100 and -108 were used as basis for further truncations. In the case of internal SOT-D-100 variants, the respective bases were simply omitted, whereas in the SOT-D-108 variants they were substituted by a flexible hydrophilic spacer during synthesis. SOT-D-100 and its derivatives SOT-D-101 and -102 as well as SOT-D-108 derivatives SOT-D-109, -110, and -111 were then tested in cell culture as described in example 2 (FIG. 9). As presented in FIG. 8, deletion of two, but not three internal nucleotides was possible without activity loss (SOT-D-101; -102). In contrast, when substituted by a spacer (SOT-D-109, -110, -111), three nucleotides coud be omitted. An optimal position of the spacer is realized in SOT-D-109 (FIG. 10).

Modifications of SOT-D-109 at the 5'-end with a 40 kDa moiety was possible without loss of ghrelin binding activity (FIG. 11).

3.2 Truncation of SOT-E

Following, the Ghrelin-Binding Sequence MS—P2-F1 (FIG. 1 and FIG. 12) which was Chosen as Lead Sequence is Referred as SOT-E.

In secondary structure predictions (minimum free energy conformations [Hofacker et al., 1994, Monatsh. Chem 125:167-188]), the possibility for canonical intramolecular base pairing between the C30 and G50 becomes obvious for Spiegelmer SOT-E (FIG. 12). In the following experiments which result in truncation of Spiegelmer SOT-E are described. All truncated versions of Spiegelmer SOT-E were tested with respect of their activity in cell culture (see Example 2).

3.2.1 Terminal Truncation of Spiegelmer SOT-E

The six nucleotides at the 3'end seem not to be hybridised to other parts of the molecule. In contrast, at the 5'-end the nucleotides may be partly paired. Surprisingly, the 3'-end can not be truncated without reduction of binding (Spiegelmer SOT-E-012) whereas Spiegelmer SOT-E-014 (truncation of six nucleotides at the 5'-end) retained full ghrelin-antagonistic activity (FIG. 13).

3.2.2 Internal Deletion Mutants of Spiegelmer SOT-E

When considering the alignment of the selected ghrelin binders MS—P2-E3, MS—P2-G2, MS—P2-D2, MS—P2-A3, MS—P2-E1, MS—P2-B1 MS—P2-C3, MS—P2-C2, MS—P2-H2, MS—P2-A4 and SOT-E (sequence family I) in FIG. 1 a variable region seems to exist in all aligned molecules at the end and directly adjacent to the helix (G36-C43 in SOT-E). The secondary structure prediction of Spiegelmer SOT-E shows a loop of four nucleotides (A38-U41; FIG. 12). In order to exploit this apparent variability for further truncation of ghrelin binders, at first the respective bases of Spiegelmer SOT-E were substituted by a flexible hydrophilic spacer during synthesis. Deletion of six (U37-A42; SOT-E-011) nucleotides, but not eight (G36-C43; SOT-E-008) nucleotides was possible without loss of activity. The combination of the results of truncation at the 5'-end (G1-A6) and the substitution of six nucleotides (U37-A42) by flexible hydrophilic spacer leads to the 44-nucleotide Spiegelmer SOT-E-019 (FIG. 14) which shows an identical $IC_{50}$ in cell culture as the 56-nucleotide Spiegelmer SOT-E (FIG. 12).

3.2.3 Rearrangement of Sequence Segments within SOT-E-019

The sequence family II represented by sequences MS—P2-A2, MS—P2-H3, MS—P2-D1 (FIG. 1) bear resemblance to sequence family I (including SOT-E). These sequence homology is highlighted as box A (UAAGAC-CGAAGGUAACCAAUCCUAC) (SEQ ID NO: 5, bases 10-34) in FIG. 1. In sequence family II box A is rather located at the 3'-end whereas in sequence family I box A is close to the 5'-end. Due to this result of the in vitro selection and the secondary structure prediction of Spiegelmer SOT-E, a variant of SOT-E-019 was designed in which box A is located at the 5'-end. For that purpose the original 5'-end and 3'-end of SOT-E-019 were linked with a flexible hydrophilic spacer and the loop was removed thus resulting in a new 5'- and 3'-end (variant SOT-E-021; FIGS. 15 and 21). Surprisingly, for SOT-E-21 no loss of activity could be observed. Further truncations on basis of SOT-E-019 and SOT-E-021 (SOT-E-33 (FIGS. 16 and 21) and SOT-E-25 (FIGS. 17 and 21) were not possible without reducing ghrelin-antagonistic functionality (FIG. 13). 3.3 Comparison of SOT-C, SOT-D-109 and SOT-E Spiegelmer SOT-E was measured by Surface Plasmon resonance (Example 2) in comparison to SOT-C and a sixfold better $K_D$ could be determined (FIG. 18). The same improved binding (fivefold better) could be detected in cell culture experiments (Example 2) with Spiegelmer SOT-E in comparison to D-109 (FIG. 19). In order to improve the residence time in the animal body, Spiegelmer SOT-E-19 was modified at its 5'-end by a 40 kDa-PEG moiety (SOT-E19-5'-PEG). Spiegelmer SOT-E19-5'-PEG showed similar results in comparison to SOT-E in cell culture experiments (FIG. 19) and additionally demonstrated in vivo activity (Example 5; FIG. 22).

3.4 Definition of Ghrelin Binding Spiegelmer Motifs

All molecules binding ghrelin, particularly ghrelin having an octanoyl acid side chain as defined herein, are primarily characterised by the presence of a motif of 25 nucleotides ("Box A") which is essential for ghrelin binding. Some of the 25 nucleotides within "Box A" seem to be interchangeable with other bases (FIG. 20A).

An essential necessity for functionality of "Box A" within a ghrelin binding Spiegelmer is the hybridisation of "Box A's" 3'-terminal five nucleotides (5'-CCUAC) with a complementary strand of the sequence 5'-GUGAGG forming a helical structure with a non-pairing central located guanosine (Box B). Deletion of this central guanosine in Box B leads to significant loss of binding ("Helix defined by Box A", Non-pairing G; FIG. 20A). 3'-adjacent to "Box A", the "Helix defined by Box A" should minimally be elongated by one, preferentially by two ore more additional, non-defined base pairs ("Box C1" and "Box C2", FIG. 20A).

At the 3'-end of "Box B" further nucleotides are essential for binding. At least two further nucleotides (preferentially 5'-CA) are necessary for binding. Significant improvement of binding can be achieved by adding further two, optimally four nucleotides at this position ("Box D", FIG. 20A) resulting in Box D comprising two, three, four, five or six nucleotides.

At the 5'-end of "Box A" further nucleotides are essential for binding. At least one further nucleotide (especially U or G) is necessary for binding. Significant improvement of binding can be achieved by adding further two nucleotides at this position ("Box E", FIG. 20A) resulting in Box E comprising one, two, three or four nucleotides.

If boxes D and E are linked via a flexible hydrophilic spacer, said spacer can also be inserted in various positions (see FIG. 8; SOT-D-109, SOT-D-110 and SOT-D-111).

Surprisingly, the defined sequence elements are functional when "Box C1" and "Box C2" instead of Box D and E linked with a flexible hydrophilic spacer.

The features of the present invention disclosed in the specification, the claims and/or the drawings may both separately and in any combination thereof be material for realizing the invention in various forms thereof.

EXAMPLE 4

Chemical Synthesis of Aptamers and Spiegelmers

Chemical Solid-phase Synthesis
Small Scale Synthesis

The aptamers were produced by solid-phase synthesis with an ABI 394 synthesizer (Applied Biosystems, Foster City, Calif., USA) using 2'TBDMS RNA phosphoramidite chemistry (M. J. Damha, K. K. Ogilvie, Methods in Molecular Biology, Vol. 20 Protocols for oligonucleotides and analogs, ed. S. Agrawal, p. 81-114, Humana Press Inc. 1993). D-rA(N—Bz)-, D-rC(Ac)—, D-rG(N-ibu)-, D-rU— and hexaethylene glycol phosphoramidites were purchased from ChemGenes, Wilmington, Mass. The aptamers were purified by gel electrophorese.

The unmodified (without PEGylation) Spiegelmers were produced by solid-phase synthesis with an ABI 394 synthesizer (Applied Biosystems, Foster City, Calif., USA) using 2'TBDMS RNA phosphoramidite chemistry (M. J. Damha, K. K. Ogilvie, Methods in Molecular Biology, Vol. 20 Protocols for oligonucleotides and analogs, ed. S. Agrawal, p. 81-114, Humana Press Inc. 1993). L-rA(N—Bz)-, L-rC(Ac)—, L-rG(N-ibu)-, L-rU— and hexaethylene glycol phosphoramidites were purchased from ChemGenes, Wilmington, Mass. The aptamers were purified by gel electrophorese.

Large Scale Synthesis Plus Modification

The modified Spiegelmer SOT-E-19 was produced by solid-phase synthesis with an ÄktaPilot100 synthesizer (Amersham Biosciences; General Electric Healthcare, Freiburg) using 2'TBDMS RNA phosphoramidite chemistry (M. J. Damha, K. K. Ogilvie, Methods in Molecular Biology, Vol. 20 Protocols for oligonucleotides and analogs, ed. S. Agrawal, p. 81-114, Humana Press Inc. 1993). L-rA(N—Bz)-, L-rC(Ac)—, L-rG(N-ibu)-, L-rU— and hexaethylene glycol phosphoramidites were purchased from ChemGenes, Wilmington, Mass. The synthesis was started on L-riboC modified CPG pore size 1000 Å (Link Technology, Glasgow, UK). For coupling (15 min per cycle), 0.3 M benzylthiotetrazole (CMS-Chemicals, Abingdon, UK) in acetonitrile, and 3.5 equivalents of the respective 0.1 M phosphoramidite solution in acetonitrile was used. The amino group at the 5'-end of the Spiegelmer was attached by coupling aminohexyl phosphoramidite (ChemGenes). An oxidation-capping cycle was used. Further standard solvents and reagents for oligonucleotide synthesis were purchased from Biosolve (Valkenswaard, NL). The Spiegelmer was synthesized DMT-ON; after deprotection, it was purified via preparative RP—HPLC (Wincott F et al 1995 *Nucleic Acids Res.* 23: 2677) using Source15RPC medium (Amersham). The 5'DMT-group was removed with 80% acetic acid (30 min at RT). Subsequently, aqueous 2 M NaOAc solution was added and the Spiegelmer Variant 1:

5'——— Box C1 ——— Box B ——— Box D ——— Spacer ——— Box E ——— Box A ——— Box C2

Variant 2:

5'——— Box E ——— Box A ——— Box C2 ——— Spacer ——— Box C1 ——— Box B ——— Box D was desalted by tangential-flow filtration using a 5 K regenerated cellulose membrane (Millipore, Bedford, Mass.).

PEGylation

In order to reduce renal clearance in vivo, the Spiegelmer SOT-E-19 was covalently coupled to a 40 kDa polyethylene glycol (PEG) moiety at the 5'-end. Using a Spiegelmer with such increased molecular mass, significantly prolonged retention in plasma and therefore longer efficiency can be achieved.

For PEGylation (see European patent application EP 1 306 382), the purified 5'-amino modified Spiegelmer was dissolved in a mixture of $H_2O$ (2.5 ml), DMF (5 ml), and buffer A (5 ml; prepared by mixing citric acid $.H_2O$ [7 g], boric acid [3.54 g], phosphoric acid [2.26 ml], and 1 M NaOH [343 ml] and adding H2O to a final volume of 1 l; pH=8.4 was adjusted with 1 M HCl)

The pH of the Spiegelmer solution was brought to 8.4 with 1 M NaOH. Then, 40 kDa PEG-NHS ester (Nektar Therapeutics, Huntsville, Ala.) was added at 37° C. every 30 min in four portions of 0.6 equivalents until a maximal yield of 75 to 85% was reached. The pH of the reaction mixture was kept at 8-8.5 with 1 M NaOH during addition of the PEG-NHS ester.

The reaction mixture was blended with 4 ml urea solution (8 M), 4 ml buffer A, and 4 ml buffer B (0.1 M triethylammonium acetate in $H_2O$) and heated to 95° C. for 15 min. The PEGylated Spiegelmer was then purified by RP—HPLC with Source 15RPC medium (Amersham), using an acetonitrile gradient (buffer B; buffer C: 0.1 M triethylammonium acetate in acetonitrile). Excess PEG eluted at 5% buffer C, PEGylated Spiegelmer at 10-15% buffer C. Product fractions with a purity of >95% (as assessed by HPLC) were combined and mixed with 40 ml 3 M NaOAC. The PEGylated Spiegelmer was desalted by tangential-flow filtration (5 K regenerated cellulose membrane, Millipore, Bedford Mass.).

EXAMPLE 5

Inhibition of the Growth Hormone Release After Exogeneous Ghrelin Administration by Anti-Ghrelin-Spiegelmer SOT-E19-5'-PEG The administration of exogenous ghrelin is known to trigger the release of growth hormone (GH) in rats. Prior administration of ghrelin-binding Spiegelmer suppresses the ghrelin-induced release of GH.

Sprague Dawley rats were adapted to their new environment for 7 days. The experimental set-up consisted of five groups with five animals each: one positive control group and 4 different doses of Spiegelmer SOT-E19-5'-PEG. All animals were anesthetized with Ketamine/Xylazine for the duration of the experiment and received two intravenous injections into the tail vein. The first injection was given 30 minutes before the second injection and consisted of PBS (positive control group) or the doses of Spiegelmer SOT-E19-5'-PEG indicated in FIG. 22. The second administration consisted of 3 nmol rat ghrelin for all animals and marked time 0 for the experiment. Prior to the second administration a first blood sample was withdrawn from the orbital sinus. Additional samples were taken at 5, 15, 30, and 45 minutes after rat ghrelin administration. The resulting plasma samples were analysed for growth hormone concentrations with a commercial enzymatic immunoassay system following the manufacturer's instructions (Growth hormone, Rat, Biotrak Assay Kit, RPN2561, Amersham Biosciences Europe GmbH, Freiburg).

As can be seen in FIG. 22, the release of GH is powerfully stimulated by the injection of rat ghrelin, but can be inhibited by the prior administration of SOT-E19-5'-PEG. Maximum inhibition is achieved at 75 nmol SOT-E19-5'-PEG/kg body weight. A further increase in the administrated dose to 150 nmol SOT-E19-5'-PEG/kg body weight suppresses GH release no further. The result demonstrates the in vivo activity of the anti-Ghrelin Spiegelmer SOT-E19-5'-PEG.

EXAMPLE 6

Derivatives of SOT-E-19 without an Internal Linker

As described in Example 3 anti-ghrelin Spiegelmer SOT-E-19 consists of L-nucleotides and an internal linker which was incorporated in the original molecule SOT-E in order to substitute 6 nucleotides. 4 out of 6 nucleotides form an loop in Spiegelmer SOT-E, the remained 2 nucleotides (out of the 6 nucleotides) may hybridize to each other (SOT-E, see FIG. 23, first row, hybridized nucleotides are underlined).

In order to realize as short as possible derivatives of SOT-E-19 without an internal linker, the linker was substituted by different building blocks of 3 nucleotides. All derivatives were synthesized as Spiegelmers (protocol see Example 4) and analyzed in cell culture experiments (protocol see Example 2). A substitution of the internal linker of SOT-E19 without loss of binding and inhibitory efficacy ($IC_{50}$) was successfully shown for the following building blocks: ACA (SOT-E-19-L3) and CAA (SOT-E-19-L4). The different derivatives of SOT-E-19 are shown in FIG. 23.

EXAMPLE 7

Discrimination of Octanoyl-ghrelin and Desoctanoyl-ghrelin by Ghrelin-binding Spiegelmers The characteristics of the binding of Spiegelmer SOT-E19 to ghrelin were further analysed in a competition assay, based on the method described in Example 2. In these assays, the Spiegelmer was incubated with different combinations of ghrelin peptides (octanoyl- and des-octanoyl ghrelin) in the stimulation solutions prior to stimulation of cells.

The scheme of peptide combinations and the results of the experiment with full-length octanoyl-ghrelin (human ghrelin=hu ghrelin) are summarized in FIG. 24 (bars numbered from left to right): without any octanoyl-ghrelin (human ghrelin=hu ghrelin), or with desoctanoyl-ghrelin in a final concentration of 300 nM, no stimulation of cells can be detected (bars 1 and 2), while already octanoyl-ghrelin (human ghrelin=hu ghrelin) in a concentration of 13 nM is sufficient for mediating calcium release (bar 3); further addition of 300 nM desoctanoyl-ghrelin (bar 4) does not interfere with cell stimulation, indicating that the biologically inactive desoctanoyl-ghrelin is not a receptor antagonist. The calcium release mediated by 3 nM octanoyl-ghrelin (human ghrelin=hu ghrelin) can be inhibited by a 10-fold excess of SOT-E19 (bar 5), and even the presence of desoctanoyl-ghrelin in a 100-fold excess (300 nM) over octanoyl-ghrelin (human ghrelin=hu ghrelin) does not compete for inhibition (bar 6). In contrast, an assay concentration of 300 nM octanoyl-ghrelin and 30 nM Spiegelmer shows increased calcium release (bar 7), giving evidence that under assay conditions a stimulation enhancement with octanoyl-ghrelin (human ghrelin=hu ghrelin) can be achieved. This experiment demonstrates, that SOT-E19 specifically discriminates between ghrelin in the octanoyl-form and the desoctanoyl-form.

Binding characteristics of Spiegelmer NOX-B11 to ghrelin (binding to octanoyl-ghrelin but not or weakly to des-octanoyl-ghrelin) are similar to SOT-E19 (The same experiment was previously done as described in WO2005/049828.

Because both molecules have a high structural correlation (see Example 3) which is mainly based on box A, the results support the assumption that motif A is essential for the high specificity of the nucleic acid molecules according to the present invention regarding to the octanoylated form of ghrelin, especially regarding the five amino acids at the N-terminus including the octanoyl group.

EXAMPLE 8

Quantification of Octanoyl-ghrelin Using Ghrelin-binding Spiegelmer

NOX-B11

The ghrelin-binding Spiegelmer NOX-B11 can be used in an assay format similar to that of an enzyme immune assay (EIA) for non-radioactive quantification of octanoylated human and rat ghrelin.

Principle

In this assay, standards, controls and unknown treated plasma are incubated in 96-well-microtiter-plates which have been coated with a ghrelin-binding Spiegelmer, e. g., Spiegelmer NOX-B11, which recognize octanoyl-ghrelin at its N-terminus. After incubation and washing, the wells are treated with an anti-ghrelin antibody (first antibody) or a nucleic acid which binds to ghrelin at the C-terminus of ghrelin. This antibody or nucleic acid can be labeled or not, whereby a nucleic acid would be preferably labeled. If the (first) antibody is not labeled, after incubation removing the (first) anti-ghrelin antibody and several washing steps a second antibody (the antibody is directed to the Fc-fragment of the first antibody and is labeled) is added. The label of the second antibody can be the enzyme horseradish peroxidase (HRP). After incubation the well with the second antibody and removal of the unbound fraction, the wells are incubated with the HRP substrate tetramethylbenzidine (TMB). An acidic stopping solution is then added and the degree of enzymatic turnover of the substrate is determined by absorbance measurement at 450 nm. The absorbance measured is directly proportional to the concentration of octanoyl-ghrelin present in the sample. A set of ghrelin standards is used to plot a standard curve of absorbance versus ghrelin concentration from which the ghrelin in unknowns can be calculated.

Protocol

Figure 26A:

Firstly, a streptavidin-coated 96-well plate (Reacti-Bind Streptavidin Coated High Bind Capacity Black 96-well Plates, Perbio Science, Bonn, Germany) was washed three times with PBS-Dulbecco (with $Mg^{2+}$ and $Ca^{2+}$, Biochrom AG, Berlin, Germany) including 0.1% Tween. Each well was incubated with 100 µl 50 µM biotinylated Spiegelmer NOX-B11 (dissolved in PBS; SEQ. ID. 72) for one hour at room temperature. After immobilisation of biotinylated Spiegelmer NOX-B11 unbound Spiegelmer was removed by one washing step (100 µl PBS). This is illustrated in FIG. 26A.

Figure 26B:

After removing the wash buffer, the stock solutions with defined concentration of octanoyl-ghrelin were added and incubated for one hour at room temperature. The supernatant was removed and the wells were washed once (100 µl PBS). This is illustrated in FIG. 26B.

Figure 26C:
Figure 26D:

The anti-ghrelin antibody (from Phoenix Peptides, Belmont, Calif., USA; 1° ab) was incubated in blocking solution (from Phoenix Peptides, Belmont, Calif., USA) for one hour, unbound antibodies were removed by five washing step (100 µl PBS each). This is illustrated in FIG. 26C In order to the detect the bound anti-ghrelin antibody, a second antibody (from Phoenix Peptides, Belmont, Calif., USA; 2° ab-HRP) was used which specifically recognize the Fc-fragment of the anti-ghrelin antibody (1° ab) and is modified with Horseradish peroxidase. The unbound fraction of the second antibody (2° ab-HRP) was removed by five washing steps (100 µl PBS). This is illustrated in FIG. 26D.

For quantification, 100 µl of TMB substrate (Amersham Biosciences, Little Chalfont, UK) was added, the plate was sealed and incubated in a dark room for 30 min. Then 50 µl of stopping solution was added. The degree of enzymatic turnover of the substrate was determined absorbance measurement at 450 nm and the difference of the absorbance units were recorded.

As shown in FIG. 25 a set of ghrelin standards was used to plot a standard curve of absorbance versus ghrelin concentration Results As a matter of principle the experimental data demonstrates that Spiegelmer NOX-B11 can be used to immobilize octanoyl-ghrelin in concentration-dependant manner and therefore has potential as reagent in an EIA type detection assay.

The features of the present invention disclosed in the specification, the claims and/or the drawings may both separately and in any combination thereof be material for realizing the invention in various forms thereof.

The invention claimed is:

1. An isolated nucleic acid having the nucleotide sequence set forth in SEQ ID NO: 39 wherein said isolated nucleic acid binds a ghrelin.

2. A kit for the detection of ghrelin, comprising the nucleic acid according to claim 1.

3. The nucleic acid of claim 1, wherein said nucleic acid further comprises a hydroxyethyl starch (HES) moiety, a polyethylene glycol (PEG) moiety or both.

4. The nucleic acid of claim 3, wherein the molecular weight of said PEG moiety is from 20 to 120 kD.

5. The nucleic acid of claim 3, wherein the molecular weight of said PEG moiety is from 30 to 80 kD.

6. The nucleic acid of claim 3, wherein the molecular weight of said PEG moiety is 40 kD.

7. The nucleic acid of claim 3, wherein the HES moiety has a molecular weight from 10 to 130 kD.

8. The nucleic acid of claim 3, wherein said HES moiety has a molecular weight from 30 to 80 kD.

9. The nucleic acid of claim 3, wherein said HES moiety has a molecular weight of 50 kD.

10. The nucleic acid of claim 1, wherein one or more nucleotides of said nucleic acid are L nucleotides.

11. The nucleic acid of claim 1, wherein all of the nucleotides of said nucleic acid are L nucleotides.

* * * * *

SEQUENCE LISTING

```
<160> NUMBER OF SEQ ID NOS: 86

<210> SEQ ID NO 1
<211> LENGTH: 28
<212> TYPE: PRT
<213> ORGANISM: Homo sapiens
<220> FEATURE:
<221> NAME/KEY: PEPTIDE
<222> LOCATION: (1)..(28)
<223> OTHER INFORMATION: GHRELIN

<400> SEQUENCE: 1

Gly Ser Ser Phe Leu Ser Pro Glu His Gln Arg Val Gln Gln Arg Lys
1               5                   10                  15
```

```
Glu Ser Lys Lys Pro Pro Ala Lys Leu Gln Pro Arg
            20                  25

<210> SEQ ID NO 2
<211> LENGTH: 28
<212> TYPE: PRT
<213> ORGANISM: Rattus norvegicus
<220> FEATURE:
<221> NAME/KEY: PEPTIDE
<222> LOCATION: (1)..(28)
<223> OTHER INFORMATION: GHRELIN

<400> SEQUENCE: 2

Gly Ser Ser Phe Leu Ser Pro Glu His Gln Lys Ala Gln Gln Arg Lys
1               5                   10                  15

Glu Ser Lys Lys Pro Pro Ala Lys Leu Gln Pro Arg
            20                  25

<210> SEQ ID NO 3
<211> LENGTH: 25
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 3
uaarwccgaa rguahccauu ccurc                                         25

<210> SEQ ID NO 4
<211> LENGTH: 25
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 4
uaagaccgaa gguacccaau ccuac                                         25

<210> SEQ ID NO 5
<211> LENGTH: 56
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 5
ggguaagcgu aagaccgaaa guaaccaauc cuaccguaua uacggugagg cagcac       56

<210> SEQ ID NO 6
<211> LENGTH: 56
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 6
ggguaagcgu aagaccgaag guaaccaauc cuaccguauc uacagugagg cagcac       56
```

<210> SEQ ID NO 7
<211> LENGTH: 56
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 7
ggguaagcgu aagaccgaag guaaccaauc cuaccguauc uacggugagg cagcac    56

<210> SEQ ID NO 8
<211> LENGTH: 56
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 8
ggguaagcgu aagaccgaag guaaccaauc cuaucguauc uauggugagg cagcac    56

<210> SEQ ID NO 9
<211> LENGTH: 56
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 9
ggguaugcau aagaccgaag guaaccaauc cuaccguauc uacggugagg cagcac    56

<210> SEQ ID NO 10
<211> LENGTH: 56
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 10
ggguaugcgu aagaccgaag guaaccaauc cuaccguauc uacggugagg cagcac    56

<210> SEQ ID NO 11
<211> LENGTH: 56
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 11
gggugagcgu aagaccgaag guaaccaauc cuaccguauc uacggugagg cagcac    56

<210> SEQ ID NO 12
<211> LENGTH: 56
<212> TYPE: RNA

```
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 12
ggguguaugu aagaccgaag guaaccaauc cuaccauauc uacggugagg cagcac          56

<210> SEQ ID NO 13
<211> LENGTH: 56
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 13 ggguguavgcgu aagaccgaag guaaccaauc cuaccauauc uacggugagg cagcac       56
```

```
ggguguvgcgu aagaccgaag guaaccaauc cuaccauauc uacggugagg cagcac        56

<210> SEQ ID NO 14
<211> LENGTH: 56
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 14 ggguguvgcgu aagaccgaag guaaccaauc cuaucauauc uacggugagg cagcac        56

<210> SEQ ID NO 15
<211> LENGTH: 56
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 15 ggguguvgcgu aagaccgaag guacccaauc cuaccuacua acuggugagg cagcac        56

<210> SEQ ID NO 16
<211> LENGTH: 55
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 16
gggugacgua agaccgaagg uacccaaucc uaccuuuccu gaggugaggc agcac          55

<210> SEQ ID NO 17
<211> LENGTH: 51
<212> TYPE: RNA
<213> ORGANISM: Artificial Sequence
<220> FEATURE:
<223> OTHER INFORMATION: Synthetic
<220> FEATURE:
<221> NAME/KEY: misc_feature
```

<223> OTHER INFORMATION: Synthetic

<400> SEQUENCE: 17
gggugcugug aggcaaaaaa guaaguccga agguaaccaa uccuacagca c            51

<210> SEQ ID NO 18
<211> LENGTH: 50
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 18
gggugcugug aggcaaugcg uaaguccgaa gguauccaau ccugcagcac              50

<210> SEQ ID NO 19
<211> LENGTH: 50
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 19
ggguguugug aggcaauaag uaaguccgaa gguaaccaau ccugcagcac              50

<210> SEQ ID NO 20
<211> LENGTH: 47
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 20
cgugugaggc aauaaaacuu aaguccgaag guaaccaauc cuacacg                 47

<210> SEQ ID NO 21
<211> LENGTH: 56
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 21
cgugugaggu aguaaaaaaa aaaaaacgua aauccgaagg uaaccaaucc uacacg       56

<210> SEQ ID NO 22
<211> LENGTH: 50
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 22
cgugcgguga ggcaaaaacg uaagaccgaa gguaaccauu ccuacccacg              50

<210> SEQ ID NO 23
<211> LENGTH: 48
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 23
cgugcgguga ggcagacgua agaccgaagg uaaccauucc uacccacg            48

<210> SEQ ID NO 24
<211> LENGTH: 41
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 24
cggugaggca gacguaagac cgaagguaac cauuccuacc g                   41

<210> SEQ ID NO 25
<211> LENGTH: 39
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 25
cggugaggca gauaagaccg aagguaacca uuccuaccg                      39

<210> SEQ ID NO 26
<211> LENGTH: 38
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 26
cggugaggca auaagaccga agguaaccau uccuaccg                       38

<210> SEQ ID NO 27
<211> LENGTH: 39
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 27
ggugaggcag acguaagacc gaagguaacc auuccuacc                      39

<210> SEQ ID NO 28
<211> LENGTH: 38
<212> TYPE: RNA

```
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 28
gguaggcaga cguaagaccg aagguaacca uuccuacc                               38

<210> SEQ ID NO 29
<211> LENGTH: 43
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 29
ccggugaggc agacguaaga ccgaagguaa ccauuccuac cgg                         43

<210> SEQ ID NO 30
<211> LENGTH: 40
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 30
ccggugaggc aguaagaccg aagguaacca uuccuaccgg                             40

<210> SEQ ID NO 31
<211> LENGTH: 40
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 31
ccggugaggc aguaagaccg aagguaacca uuccuaccgg                             40

<210> SEQ ID NO 32
<211> LENGTH: 40
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 32
ccggugaggc cguaagaccg aagguaacca uuccuaccgg                             40

<210> SEQ ID NO 33
<211> LENGTH: 56
<212> TYPE: RNA
<213> ORGANISM: Artificial Sequence
<220> FEATURE:
<223> OTHER INFORMATION: Synthetic
<220> FEATURE:
<221> NAME/KEY: misc_feature
```

```
<223> OTHER INFORMATION: Synthetic

<400> SEQUENCE: 33
gggugagcgu aagaccgaag guaaccaauc cuaccguauc uacggugagg cagcac        56

<210> SEQ ID NO 34
<211> LENGTH: 49
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (36)..(36)
<223> OTHER INFORMATION: N is Spacer

<400> SEQUENCE: 34
gggugagcgu aagaccgaag guaaccaauc cuaccnggug aggcagcac               49

<210> SEQ ID NO 35
<211> LENGTH: 49
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 35
cguaagaccg aagguaacca auccuaccgu aucuacggug aggcagcac               49

<210> SEQ ID NO 36
<211> LENGTH: 51
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (37)..(37)
<223> OTHER INFORMATION: N is Spacer

<400> SEQUENCE: 36
gggugagcgu aagaccgaag guaaccaauc cuaccgncgg ugaggcagca c            51

<210> SEQ ID NO 37
<211> LENGTH: 54
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 37
gggugagcgu aagaccgaag guaaccaauc cuaccguauc uacggugagg cagc         54

<210> SEQ ID NO 38
<211> LENGTH: 50
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 38
```
gcguaagacc gaagguaacc aauccuaccg uaucuacggu gaggcagcac    50

<210> SEQ ID NO 39
<211> LENGTH: 45
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (31)..(31)
<223> OTHER INFORMATION: N is Spacer

<400> SEQUENCE: 39
gcguaagacc gaagguaacc aauccuaccg ncggugaggc agcac    45

<210> SEQ ID NO 40
<211> LENGTH: 45
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (15)..(15)
<223> OTHER INFORMATION: N is Spacer

<400> SEQUENCE: 40
cggugaggca gcacngcgua agaccgaagg uaaccaaucc uaccg    45

<210> SEQ ID NO 41
<211> LENGTH: 43
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (13)..(13)
<223> OTHER INFORMATION: N is Spacer

<400> SEQUENCE: 41
cggugaggca gcngcguaag accgaaggua accaauccua ccg    43

<210> SEQ ID NO 42
<211> LENGTH: 43
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (31)..(31)
<223> OTHER INFORMATION: N is Spacer

<400> SEQUENCE: 42
gcguaagacc gaagguaacc aauccuaccg ncggugaggc agc    43

<210> SEQ ID NO 43
<211> LENGTH: 50
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 43
gcguaagacc gaagguaacc aauccuaccg uaucuacggu gaggcagcac        50

<210> SEQ ID NO 44
<211> LENGTH: 47
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 44
gcguaagacc gaagguaacc aauccuaccg aaacggugag gcagcac        47

<210> SEQ ID NO 45
<211> LENGTH: 47
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 45
gcguaagacc gaagguaacc aauccuaccg auacggugag gcagcac        47

<210> SEQ ID NO 46
<211> LENGTH: 47
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 46
gcguaagacc gaagguaacc aauccuaccg acacggugag gcagcac        47

<210> SEQ ID NO 47
<211> LENGTH: 47
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 47
gcguaagacc gaagguaacc aauccuaccg caacggugag gcagcac        47

<210> SEQ ID NO 48
<211> LENGTH: 48
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 48
gcguaagacc gaagguaacc aauccuaccg aucucgguga ggcagcac        48

<210> SEQ ID NO 49
<211> LENGTH: 47

```
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 49
gcguaagacc gaagguaacc aauccuaccg uuucggugag gcagcac                47

<210> SEQ ID NO 50
<211> LENGTH: 47
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 50
gcguaagacc gaagguaacc aauccuaccg uaucggugag gcagcac                 47

<210> SEQ ID NO 51
<211> LENGTH: 45
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: PEG moiety attached to 5' end
<220> FEATURE:
<221> NAME/KEY: misc_feature
<222> LOCATION: (31)..(31)
<223> OTHER INFORMATION: N is Spacer

<400> SEQUENCE: 51
gcguaagacc gaagguaacc aauccuaccg ncggugaggc agcac                   45

<210> SEQ ID NO 52
<211> LENGTH: 40
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic
<220> FEATURE:
<221> NAME/KEY: misc_feature
<222> LOCATION: (1)..(1)
<223> OTHER INFORMATION: PEG moiety attached to 5' end

<400> SEQUENCE: 52
ccggugaggc aguaagaccg aagguaacca uuccuaccgg                         40

<210> SEQ ID NO 53
<211> LENGTH: 28
<212> TYPE: PRT
<213> ORGANISM: Homo sapiens
<220> FEATURE:
<221> NAME/KEY: MISC_FEATURE
<223> OTHER INFORMATION: Biotinylated human D-ghrelin

<400> SEQUENCE: 53

Gly Ser Ser Phe Leu Ser Pro Glu His Gln Arg Val Gln Gln Arg Lys
1               5                   10                  15
```

```
Glu Ser Lys Lys Pro Pro Ala Lys Leu Gln Pro Arg
            20                  25
```

<210> SEQ ID NO 54
<211> LENGTH: 56
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 54
ggguaagcgu aagaccgaaa guaaccaauc cuaccguaua uacggugagg cagcac    56

<210> SEQ ID NO 55
<211> LENGTH: 56
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 55
ggguaagcgu aagaccgaag guaaccaauc cuaccguauc uacagugagg cagcac    56

<210> SEQ ID NO 56
<211> LENGTH: 56
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 56
ggguaagcgu aagaccgaag guaaccaauc cuaccguauc uacggugagg cagcac    56

<210> SEQ ID NO 57
<211> LENGTH: 56
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 57
ggguaagcgu aagaccgaag guaaccaauc cuaucguauc uauggugagg cagcac    56

<210> SEQ ID NO 58
<211> LENGTH: 56
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 58
ggguaugcau aagaccgaag guaaccaauc cuaccguauc uacggugagg cagcac    56

<210> SEQ ID NO 59

```
<211> LENGTH: 56
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 59
ggguaugcgu aagaccgaag guaaccaauc cuaccguauc uacggugagg cagcac          56

<210> SEQ ID NO 60
<211> LENGTH: 56
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 60
gggugagcgu aagaccgaag guaaccaauc cuaccguauc uacggugagg cagcac          56

<210> SEQ ID NO 61
<211> LENGTH: 56
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 61
ggguguaugu aagaccgaag guaaccaauc cuaccauauc uacggugagg cagcac          56

<210> SEQ ID NO 62
<211> LENGTH: 56
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 62
gggugugcgu aagaccgaag guaaccaauc cuaccauauc uacggugagg cagcac          56

<210> SEQ ID NO 63
<211> LENGTH: 56
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 63
gggugugcgu aagaccgaag guaaccaauc cuaucauauc uacggugagg cagcac          56

<210> SEQ ID NO 64
<211> LENGTH: 56
<212> TYPE: RNA
<213> ORGANISM: Artificial Sequence
<220> FEATURE:
<223> OTHER INFORMATION: Synthetic
```

```
<220> FEATURE:
<221> NAME/KEY: misc_feature
<223> OTHER INFORMATION: Synthetic

<400> SEQUENCE: 64
gggugugcgu aagaccgaag gucccaauc cuaccuacua acuggugagg cagcac         56

<210> SEQ ID NO 65
<211> LENGTH: 55
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 65
gggugacgua agaccgaagg ucccaauuc uaccuuuccu gaggugaggc agcac           55

<210> SEQ ID NO 66
<211> LENGTH: 51
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 66
gggugcugug aggcaaaaaa guaaguccga agguaaccaa uccuacagca c              51

<210> SEQ ID NO 67
<211> LENGTH: 50
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 67
gggugcugug aggcaaugcg uaaguccgaa gguauccaau ccugcagcac                50

<210> SEQ ID NO 68
<211> LENGTH: 47
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 68
cgugugaggc aauaaaacuu aaguccgaag guaaccaauc cuacacg                   47

<210> SEQ ID NO 69
<211> LENGTH: 40
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 69
```
ccggugaggc aguaagaccg aagguaacca uuccuaccgg                                40

<210> SEQ ID NO 70
<211> LENGTH: 56
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 70
gggugagcgu aagaccgaag guaaccaauc cuaccguauc uacggugagg cagcac          56

<210> SEQ ID NO 71
<211> LENGTH: 40
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 71
uaaggaaacu cggucugaug cgguagcgcu gugcagagcu                                40

<210> SEQ ID NO 72
<211> LENGTH: 47
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 72
cgugugaggc aauaaaacuu aaguccgaag guaaccaauc cuacacg                     47

<210> SEQ ID NO 73
<211> LENGTH: 35
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 73
gggugagcgu aagaccgaag guaaccaauc cuacc                                  35

<210> SEQ ID NO 74
<211> LENGTH: 36
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 74
gggugagcgu aagaccgaag guaaccaauc cuaccg                                 36

<210> SEQ ID NO 75

-continued

```
<211> LENGTH: 30
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 75
gcguaagacc gaagguaacc aauccuaccg                                          30

<210> SEQ ID NO 76
<211> LENGTH: 14
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 76
cggugaggca gcac                                                           14

<210> SEQ ID NO 77
<211> LENGTH: 12
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 77
cggugaggca gc                                                             12

<210> SEQ ID NO 78
<211> LENGTH: 30
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 78
gcguaagacc gaagguaacc aauccuaccg                                          30

<210> SEQ ID NO 79
<211> LENGTH: 30
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic
<220> FEATURE:
<221> NAME/KEY: misc_feature
<222> LOCATION: (1)..(1)
<223> OTHER INFORMATION: PEG moiety attached to 5' end

<400> SEQUENCE: 79
gcguaagacc gaagguaacc aauccuaccg                                          30

<210> SEQ ID NO 80
<211> LENGTH: 13
```

<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 80
ggugaggcag cac                                                    13

<210> SEQ ID NO 81
<211> LENGTH: 14
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 81
cggugaggca gcac                                                   14

<210> SEQ ID NO 82
<211> LENGTH: 14
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 82
cggugaggca gcac                                                   14

<210> SEQ ID NO 83
<211> LENGTH: 30
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 83
gcguaagacc gaagguaacc aauccuaccg                                  30

<210> SEQ ID NO 84
<211> LENGTH: 30
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 84
gcguaagacc gaagguaacc aauccuaccg                                  30

<210> SEQ ID NO 85
<211> LENGTH: 12
<212> TYPE: RNA
<213> ORGANISM: Artificial Sequence
<220> FEATURE:
<223> OTHER INFORMATION: Synthetic
<220> FEATURE:

```
<221> NAME/KEY: misc_feature
<223> OTHER INFORMATION: Synthetic

<400> SEQUENCE: 85
cggugaggca gc                                                         12

<210> SEQ ID NO 86
<211> LENGTH: 14
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 86
cggugaggca gcac                                                       14
```